(12) United States Patent
Grimmer et al.

(10) Patent No.: US 11,244,752 B2
(45) Date of Patent: Feb. 8, 2022

(54) SYSTEM AND METHOD FOR IMPLEMENTING MEAL SELECTION BASED ON VITALS, GENOTYPE AND PHENOTYPE

(71) Applicant: NEDERLANDSE ORGANISATIE VOOR TOEGEPAST—NATUURWETENSCHAPPELIJK ONDERZOEK TNO, Da 's-Gravenhage (NL)

(72) Inventors: Neil Grimmer, Emeryville, CA (US); Joshua Anthony, Princeton, NJ (US); Ryan Yockey, Emeryville, CA (US); Matt Van Horn, Emeryville, CA (US); Jon Allen, Emeryville, CA (US); Erin Barrett, Emeryville, CA (US); Barbara Winters, Emeryville, CA (US); Heather Cutter, Emeryville, CA (US); Angie Westbrock, Emeryville, CA (US); Matt Town, Emeryville, CA (US); Jennifer Carrico, San Francisco, CA (US)

(73) Assignee: NEDERLANDSE ORGANISATIE VOOR TOEGEPAST—NATUURWETENSCHAPPELIJK ONDERZOEK TNO, Da 's Gravenhag (NL)

( * ) Notice: Subject to any disclaimer, the term of this patent is extended or adjusted under 35 U.S.C. 154(b) by 0 days.

(21) Appl. No.: 15/896,987

(22) Filed: Feb. 14, 2018

(65) Prior Publication Data
US 2018/0240542 A1 Aug. 23, 2018

Related U.S. Application Data

(63) Continuation of application No. 15/792,673, filed on Oct. 24, 2017, now abandoned.
(Continued)

(51) Int. Cl.
*G16H 20/60* (2018.01)
*G06F 16/9535* (2019.01)

(52) U.S. Cl.
CPC ......... *G16H 20/60* (2018.01); *G06F 16/9535* (2019.01)

(58) Field of Classification Search
CPC .................................................. G16H 20/60
See application file for complete search history.

(56) References Cited

U.S. PATENT DOCUMENTS

| | | |
|---|---|---|
| 6,355,859 B1 | 3/2002 | Bosworth et al. |
| 6,358,546 B1 | 3/2002 | Bebiak et al. |

(Continued)

FOREIGN PATENT DOCUMENTS

| | | |
|---|---|---|
| WO | WO 2009/140601 A2 | 11/2009 |
| WO | WO 2010/111486 A3 | 9/2010 |

(Continued)

OTHER PUBLICATIONS

Blaak et al. "Fat Oxidation before and after a High Fat Load in the Obese Insulin-Resistant State" J. Clin. Endocrinol. Metab., vol. 91, No. 4, pp. 1462-1469 (2006).

(Continued)

*Primary Examiner* — Evangeline Barr
(74) *Attorney, Agent, or Firm* — Banner & Witcoff, Ltd.

(57) ABSTRACT

Systems and methods for recommending foods to a user based on health data, includes a database, a memory and a processor. The database stores user health data for each user within a plurality of users, including vitals, genotypic and phenotypic data, user food preference data and foods data that includes macronutrient and micronutrient data for foods that may be recommended to a user. The memory stores program instructions, including program instructions that are capable of (i) classifying user health data into predeter- (Continued)

mined diet types and micronutrient recommendations, (ii) filtering the food data to determine available foods for a user; (iii) a ranking available meals for the user based on the micronutrient recommendations and the food data, and (iv) translating micronutrient recommendations and/or food data for the available foods for the user into specific food recommendations for the user.

44 Claims, 45 Drawing Sheets

Related U.S. Application Data

(60) Provisional application No. 62/412,114, filed on Oct. 24, 2016.

(56) References Cited

U.S. PATENT DOCUMENTS

| | | |
|---|---|---|
| 6,493,641 B1 | 12/2002 | Singh et al. |
| 6,576,280 B2 | 6/2003 | Bebiak et al. |
| 6,669,975 B1 | 12/2003 | Abene et al. |
| 7,226,792 B2 | 6/2007 | Roberts et al. |
| 7,842,506 B2 | 11/2010 | Hall et al. |
| 7,873,482 B2 | 1/2011 | Stefanon et al. |
| 7,877,273 B2 | 1/2011 | Abramson |
| 7,892,763 B2 | 2/2011 | Dodds |
| 7,970,552 B1 | 6/2011 | Stefanon et al. |
| 8,000,982 B2 | 8/2011 | Kane et al. |
| 8,060,354 B2 | 11/2011 | Dodds |
| 8,065,324 B2 | 11/2011 | Kenedy et al. |
| 8,224,587 B1 | 7/2012 | Dodds |
| 8,234,099 B2 | 7/2012 | Dodds |
| 8,450,072 B2 | 5/2013 | Dodds |
| 8,450,074 B2 | 5/2013 | Dodds |
| 8,548,817 B2 | 10/2013 | Torney et al. |
| 8,612,454 B2 | 12/2013 | Charles et al. |
| 8,637,495 B2 | 1/2014 | Waldron et al. |
| 8,762,167 B2 | 6/2014 | Blander et al. |
| 2004/0131658 A1 | 7/2004 | Kaput |
| 2005/0158734 A1 | 7/2005 | Kaput |
| 2006/0045909 A1 | 3/2006 | Friesen et al. |
| 2007/0099302 A1* | 5/2007 | Horn ............... G01N 33/5091 436/68 |
| 2008/0275728 A1 | 11/2008 | Ordovas |
| 2008/0275912 A1 | 11/2008 | Roberts et al. |
| 2008/0317835 A1 | 12/2008 | Azimi et al. |
| 2009/0175980 A1 | 7/2009 | Willcocks et al. |
| 2009/0222282 A1 | 9/2009 | Ordovas et al. |
| 2010/0112570 A1 | 5/2010 | Aziz et al. |
| 2010/0113892 A1 | 5/2010 | Kaput et al. |
| 2010/0136561 A1 | 6/2010 | Draper et al. |
| 2010/0312582 A1 | 12/2010 | Sorensen |
| 2011/0137242 A1 | 6/2011 | Abramson |
| 2011/0189161 A1 | 8/2011 | Blum et al. |
| 2012/0041066 A1 | 2/2012 | Lombard |
| 2012/0083669 A1 | 4/2012 | Abujbara |
| 2012/0130732 A1 | 5/2012 | Blander et al. |
| 2012/0220488 A1 | 8/2012 | Li |
| 2012/0225047 A1 | 9/2012 | Salonen |
| 2012/0233002 A1 | 9/2012 | Abujbara |
| 2012/0258183 A1 | 10/2012 | Smith et al. |
| 2012/0295256 A1 | 11/2012 | Castellon et al. |
| 2013/0079612 A1* | 3/2013 | Hunt ................ A61B 5/14532 600/365 |
| 2013/0151270 A1 | 6/2013 | Nova et al. |
| 2013/0183692 A1 | 7/2013 | Dodds |
| 2013/0195827 A1 | 8/2013 | Blum et al. |
| 2013/0261183 A1 | 10/2013 | Bhagat |
| 2013/0280681 A1 | 10/2013 | Narayan et al. |
| 2014/0052722 A1 | 2/2014 | Bertsimas et al. |
| 2014/0065606 A1 | 3/2014 | Green et al. |
| 2014/0093478 A1 | 4/2014 | Turnbaugh et al. |
| 2014/0141983 A1 | 5/2014 | Singh et al. |
| 2014/0149143 A1 | 5/2014 | Kim et al. |
| 2014/0309137 A1 | 10/2014 | Pan et al. |
| 2014/0335482 A1 | 11/2014 | Aronis et al. |
| 2015/0010673 A1 | 1/2015 | Collino et al. |
| 2015/0011019 A1 | 1/2015 | Brahmbhatt et al. |
| 2015/0072363 A1 | 3/2015 | Collino et al. |
| 2015/0075262 A1 | 3/2015 | Martin et al. |
| 2015/0080264 A1 | 3/2015 | Martin et al. |
| 2015/0174080 A1 | 6/2015 | Schiffrin et al. |
| 2016/0292391 A1* | 10/2016 | Fink ................... G06F 19/3475 |
| 2016/0306931 A1 | 10/2016 | Lahteenmaki |
| 2017/0286625 A1* | 10/2017 | Blander ................. G16H 50/30 |
| 2018/0004914 A1 | 1/2018 | Abujbara |
| 2018/0137935 A1* | 5/2018 | Korst ................. G09B 19/0092 |

FOREIGN PATENT DOCUMENTS

| | | |
|---|---|---|
| WO | WO 2012/006669 A1 | 1/2012 |
| WO | WO 2014/086603 A1 | 6/2014 |
| WO | WO 2014/086604 A1 | 6/2014 |
| WO | WO 2014/086605 A1 | 6/2014 |
| WO | WO 2014/143080 A1 | 9/2014 |
| WO | WO 2014/154492 A1 | 10/2014 |
| WO | WO 2014/154493 A1 | 10/2014 |
| WO | WO 2016/036743 A1 | 3/2016 |

OTHER PUBLICATIONS

Kardinaal et al. "Quantifying phenotypic flexibility as the response to a high-fat challenge test in different states of metabolic health" The FASEB Journal, vol. 29, No. 11, pp. 4600-4613 (2015).

Stroeve et al. "Phenotypic flexibility as a measure of health: the optimal nutritional stress response test" Genes and Nutrition, vol. 10, No. 13 (2015).

Van Amelsvoort et al. "Effects of varying the carbohydrate: fat ratio in a hot lunch on postprandial variables in male volunteers" British Journal of Nutrition, vol. 61, pp. 267-283 (1989).

Van Ommen et al. "Phenotypic flexibility as key factor in the human nutrition and health relationship" Genes and Nutrition, vol. 9, No. 5 (2014).

Kawajiri et al. "Association of Gene Polymorphism of the Fat Mass and Obesity Associated Gene with Metabolic Syndrome: A Retrospective Cohort Study in Japanese Workers." Yonago Acta medica, vol. 55, No. 2, Jul. 2012, pp. 29-40).

Thurnham et al. "Micronutrients in Childhood and the Influence of Subclinical Inflammation." Proceedings of the Nutrition Society, vol. 64, Nov. 2005, pp. 502-509).

Van Ommen et al. Challenging homeostasis to define biomarkers for nutrition related health. Mol. Nutr. Food Res. 2009, 53.795-804. XP5 5681881.

Besser, et al. "Lessons From the Mixed-Meal Tolerance Test," Diabetes Care, vol. 36, Feb. 2013, pp. 195-201.

* cited by examiner

FIGURE 3

| # | Name | Used For |
|---|---|---|
| 1 | C-peptide fasting | Metabolic health, insulin sensitivity |
| 2 | C-peptide_t30 | |
| 3 | C-peptide_t120 | |
| 4 | Carotenoids plasma | Intake --> recommendations for carotenoid |
| 5 | Disposition index | Metabolic health, insulin sensitivity --> beta-cell diagnosis; how well you process the insulin |
| 6 | Glucose fasting | Metabolic health, insulin sensitivity, metabolic syndrome |
| 7 | Glucose_t30 | |
| 8 | Glucose_t120 | |
| 9 | Hepatic insulin index | Metabolic health, insulin sensitivity |
| 10 | HDL cholesterol | Heart health |
| 11 | High sensitivity C-reactive protein | Inflamation; how your body responds to proteins |
| 12 | LDL cholesterol | Heart health |
| 13 | Magnesium category | Blood pressure, inflamation, insulin sensitivity |
| 14 | Omega-3 index | Intake --> recommendation for omega 3; heart health |
| 15 | Potassium category | Blood pressure, heart health |
| 16 | Ratio ARA:EPA plasma | Omega 3 complex, inflamation (ratio of two amino acids) |
| 17 | Ratio total cholesterol : hdl cholesterol | |
| 18 | Sodium | Blood pressure, heart health |
| 19 | Total cholesterol | Heart health |
| 20 | Triglycerides fasting | Heart health, blood lipids, metabolic health, metabolic syndrom |
| 21 | Triglycerides_t30 | |
| 22 | Triglycerides_t120 | |
| 23 | Vitamin A plasma | Intake --> direct recommendation |
| 24 | Vitamin B6 category | Intake --> direct recommendation, blood pressure |
| 25 | Vitamin C category | Intake --> direct recommendation, blood pressure |
| 26 | Vitamin D plasma | Intake --> direct recommendation |
| 27 | Vitamin E plasma | Intake --> direct recommendation |
| 28 | Zinc category Close | |

FIGURE 4

| # | SNP | Used For |
|---|---|---|
| 1 | ACE rs1799752 | Endurance performance |
| 2 | ACE rs4646994 | Blood pressure, sodium recommendation |
| 3 | ADAMTS9 rs4607103 | Insulin sensitivity, fiber recommendation |
| 4 | ADRB3 rs4994 | Endurance performance |
| 5 | AGT rs5051 | Blood pressure, sodium recommendation |
| 6 | AGT rs699 | Blood pressure, sodium recommendation |
| 7 | APOA5-A4-C3-A1 rs964184 | Macro fat recommendation, diet type, blood pressure, insulin sensitivity (specifically fat consumption) |
| 8 | CETP rs1532624 | Heart health, LDL, total cholesterol diagnosis |
| 9 | CETP rs3764261 | Diet type (carbs), insulin sensitivity low carb tree |
| 10 | CYP1A2 rs762551 | Caffeine sensitivity |
| 11 | FADS1 rs174546 | Heart health, blood pressure for epa dha recommendation (omega 3), intake omega 3 |
| 12 | FADS1 rs174548 | Heart health, blood pressure for epa dha recommendation (omega 3), intake omega 3 |
| 13 | FTO rs1121980 | Diet type (carbs, fats), nsulin sensitivity for fat consumption, insulin sensitivity for low carb, weight maintenance for energy balance |
| 14 | FTO rs9939609 | Diet type (carbs, fats, protein), blood pressure for fat |
| 15 | GC rs2282679 | Vitamin D recommendation, inflamation |
| 16 | GC rs4588 | Vitamin D recommendation, inflamation |
| 17 | GC rs7041 | Vitamin D recommendation, inflamation |
| 18 | GCKR rs780094 | Insulin sensitivity for fasting glucose |
| 19 | HLA-DQ2.2 rs2395182 | Gluten sensitivity |
| 20 | HLA-DQ2.2 rs4713586 | Gluten sensitivity |
| 21 | HLA-DQ2.2 rs7775228 | Gluten sensitivityD28 |
| 22 | HLA-DQ2.5 rs2187668 | Gluten sensitivity |
| 23 | HLA-DQ7 rs4639334 | Gluten sensitivity |
| 24 | HLA-DQ8 rs7454108 | Gluten sensitivity |
| 25 | IGF2BP2 rs4402960 | Diet type (fats), insulin sensitivity for fat consumption |
| 26 | IL6 rs1800795 | Inflamation |
| 27 | MCM6 rs4988235 | Lactose sensitivity |
| 28 | MTHFR rs1801133 | Blood pressure in terms of riboflavin |
| 29 | NOS3 rs1799983 | Blood pressure for cocoa flavanols, resveratrol |
| 30 | PPARG rs1801282 | Diet type (fats), insulin sensitivity for fat consumption |
| 31 | R577X rs1815739 | Muscle performance |
| 32 | TCF7L2 rs7903146 | Diet type (carbs, fats), blood pressure for fat, insulin sensitivity for low carbs, weight maintenance for energy balance |
| 33 | TNF rs1800629 | Inflammation |
| 34 | VDR rs1544410 | Diagnosis for Vitamin D |

| Diet Type | Calories | % Carbs | % Fat | % Protein | Cal. Carb | Cal. Fat | Cal. Pro | Carb. in g | Fat in g | Prot. in g |
|---|---|---|---|---|---|---|---|---|---|---|
| 1 | 2000 | 45 - 65 | 20 - 40 | 10 - 22 | 1000 | 600 | 400 | 250 | 67 | 100 |
| 2 | 2000 | 45 - 65 | 20 - 40 | 18 - 35 | 900 | 500 | 600 | 225 | 56 | 150 |
| 3 | 2000 | 35 - 50 | 20 - 40 | 10 - 22 | 800 | 800 | 400 | 200 | 89 | 100 |
| 4 | 2000 | 35 - 50 | 20 - 40 | 18 - 35 | 700 | 600 | 700 | 175 | 67 | 175 |
| 5 | 2000 | 45 - 65 | 20 - 30 | 10 - 22 | 1200 | 400 | 400 | 400 | 44 | 100 |
| 6 | 2000 | 45 - 65 | 20 - 30 | 18 - 35 | 900 | 400 | 700 | 225 | 44 | 175 |
| 7 | 2000 | 35 - 50 | 20 - 30 | 18 - 35 | 800 | 500 | 700 | 200 | 46 | 175 |

605 spans % Carbs, % Fat, % Protein
610 spans Cal. Carb, Cal. Fat, Cal. Pro
615 spans Carb. in g, Fat in g, Prot. in g

| Food Group | Serving Size | Diet Type 1 | Diet Type 2 | Diet Type 3 | Diet Type 4 | Diet Type 5 | Diet Type 6 | Diet Type 7 |
|---|---|---|---|---|---|---|---|---|
| Starch | ½ cup cooked | 6 | 4 | 4 | 2 | 6 | 4 | 3 |
| Legumes | ½ cup cooked | 2 | 4 | 3 | 2 | 4 | 5 | 3 |
| Fruit | ½ cup fresh | 4 | 4 | 3 | 2 | 5 | 3 | 2 |
| Non Starchy Vegetable | 1 cup raw, ½ cup cooked | 10 | 8 | 8 | 8 | 10 | 8 | 8 |
| Fat | 1 tsp oil, 1 TB nuts | 10 | 5 | 12 | 5 | 7 | 6 | 6 |
| Full Fat Dairy | 8 ounces | 0 | 0 | 0 | 0 | 0 | 0 | 0 |
| Low Fat Dairy | 8 ounces | 0 | 0 | 1 | 0 | 0 | 0 | 0 |
| Non Fat Dairy | 8 ounces | 1 | 1 | 0 | 4 | 2 | 1 | 3 |
| HI Fat Meat | 1 ounce | 0 | 0 | 0 | 0 | 0 | 0 | 0 |
| Medium Fat Meat | 1 ounce | 0 | 4 | 3 | 5 | 0 | 3 | 0 |
| Lean Meat | 1 ounce | 6 | 4 | 3 | 5 | 3 | 0 | 8 |
| Very Lean Meat | 1 ounce | 0 | 4 | 0 | 5 | 0 | 10 | 7 |

FIGURE 8

| Alpha-linolenic acid | Biotin | Calcium |
|---|---|---|
| Carotenoids | Chloride | Choline |
| Chromium | Cinnamon | Cocoa flavanol |
| Copper | Energy balance | Energy expenditure |
| EPA and/or DHA | Fiber | Flaxseed |
| Fluoride | Folate | Fruit |
| Garlic extract | Hydroxytyrosol | Iodine |
| Iron | Lutein | Lycopene |
| Magnesium | Manganese | Molybdenum |
| Monacolin K | Niacin | Oat beta glucan (soluble fiber) |
| Omega-3s | Pantothenic acid | Pectin |
| Phosphorus | Plantstanols | Plantsterols |
| Plantsterols and stanol esters | Potassium | Riboflavin |
| Selenium | Sodium | Soy isoflavones |
| Synthetic zeaxanthin | Thiamin | Trans-resveratrol |
| Vegetables | Vitamin A | Vitamin B12 |
| Vitamin B6 | Vitamin C | Vitamin D |
| Vitamin E | Vitamin K | Walnut |
| Whey protein | Zinc | |

FIGURE 11A

| Order of Decision | | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| Diabetes Category | Normal | x | x | | | | | | | | | | | | | | | | | | | |
| | IGT | | | x | x | x | x | x | x | | | | | | | | | x | x | x | x | x |
| | IFG | | | | | | | | | | | | | x | x | x | x | | | | | |
| | IFG/ITG | | | | | | | | | | | | | | | | | | | | | |
| FTO rs9939609 | T, T | x | | | | | | | | | | | | x | | | | | | x | x | x |
| | A, T | | | x | | | | | | x | | x | x | | x | | | | | | | |
| | A, A | | | | | | | | | | | | x | | | | x | | | | | |
| Waist Circumference | High | x | | | | | | | | | | | | | | | | | | | | |
| | Normal | | | x | x | x | x | x | x | x | x | x | x | | | x | x | x | x | x | x | x |
| FTO rs1121980 | T, T | | | | | | | | | | | | | | | | | | | x | | |
| | C, T | | | | x | | x | x | x | | | | | | | | | x | x | | | x |
| | C, C | | | | | x | | | | | | | | | | | | | | | | |
| CETP rs3764261 | G, G | | | | | x | | | | | | | | | | | | | | | | |
| | G, T | | | | | | x | x | x | | | | | | | | | | | | | |
| | T, T | | | | | | | x | | | | | | | | | | | | | | x |
| TCF7L2 rs7903146 | T, T | | | | | | | x | | | | | | | | | | | | | | x |
| | C, T | | | | | | | | x | | | | | | | | | x | x | | x | |
| | C, C | | | | | | | | | | | | | | | | | | | | | |
| Diabetes subtype beta-cell category | Yes | | | | | | | | | x | x | x | x | x | x | | x | | x | | | |
| | No | | | | | | | | | | | | | | | | | | | | | |
| RESULTS | | C | C | C | C | C | C | C | C | C | C | C | C | C | C | C | C | C | C | C | C | C |

FIGURE 11B

| Order of Decision | | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|
| Diabetes Category | Normal | | | | | | | | | | | | | | | | | | | | | |
| | IGT | x | x | x | x | x | | | | | | | | | | | | | | | | |
| | IFG | | | x | | | | | | | | | | | | | | | | | | |
| | IFG / ITG | | | | | | | | | | | | | | | | | | | | x | |
| FTO rs9939609 | T,T | x | | x | x | | x | x | x | x | x | x | x | x | x | x | x | x | x | x | x | x |
| | A,T | | x | | | | x | x | x | x | x | x | x | x | | | | | | | | |
| | A,A | | | | | x | | | | | | | | | | | | | | | | |
| Waist Circumference | High | x | | x | x | x | | | | | | | | | | | | | | | | |
| | Normal | | | | | | x | | | | | | | x | x | x | x | x | x | x | x | x |
| FTO rs1121980 | T,T | x | x | | | | | | | | | | | | | | | | | | | |
| | C,T | | | x | | | | x | | | | | | | x | x | x | | | | | |
| | C,C | x | | | x | x | | | x | | | | | | | | | x | | | | |
| | G,G | | | | | | | | x | | | | | | | | x | | | | | |
| CETP rs3764261 | G,T | x | | | | | | | | x | | | | | | | | | | | | |
| | T,T | | x | x | x | x | | | | | x | x | x | x | | | | | x | x | x | x |
| TCF7L2 rs7903146 | T,T | | | | | | | | | | | x | | | | | | | | x | | |
| | C,T | | | x | | | | | | | | | x | | | | | | | | | |
| | C,C | | | | | | | | | | | | | | | | | | | | x | |
| Diabetes subtype beta-cell category | Yes | | | | x | | | | | | | | | | | | | | | | x | |
| | No | | | | | x | | | | | | | | x | | | | | | | | x |
| RESULTS | | c | c | c | c | c | c | c | c | c | c | c | c | c | c | c | c | c | c | c | c | c |

FIGURE 12A

| Order of Decision | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| Total Triglyceride Category | >= Elevated | x | | | | | | | | | | | | | | | | | | | | | | |
| | <= Slightly Elevated | | x | | | | | | | | | | x | | x | x | x | x | x | x | x | x | x | |
| FTO rs9939609 | T, T | | | x | | | | | | | | | | | | | | | | | | | | |
| | A, T | | | | x | | | | | | | | | | | | | | | | | | | |
| | A, A | x | | | | | | | | | | | | | | | | | | | | | | |
| | High | x | x | x | x | | | | | | | | | | | | | | | | | | | |
| Waist Circumference | Normal | | | | | x | x | x | x | x | x | x | x | x | x | x | x | x | x | x | x | x | x | x |
| APOA5-A4-C3-A1 rs964184 | C, C | | | | | | | | | | | | | | | | | | | | | | | |
| | C, G | | | | | | | x | x | | | x | x | | | | | | | | | | | |
| | G, G | | | | | x | x | | | | | | | | | | | | | | | | | |
| Blood Pressure Category | High | | | | | x | x | x | x | | | | | | | | | | | | | | | |
| | Normal | | | | | | | | | x | x | x | x | x | x | x | x | x | x | x | x | x | x | x |
| Diabetes subtype beta-cell category | Yes | | | | | | | | | x | | | | | | | | | | | | | | |
| | No | | | | | | | | | | x | | | | | | | | | | | | | |
| FTO rs1121980 | T, T | | | | | | | | | | | | | | | | | x | x | | | | | |
| | C, T | | | | | | | | | | | | | | | x | | | | | | | | |
| | C, C | | | | | | | | | | | | | | | | x | | | | | | | |
| PPARG rs1801282 | C, C | | | | | | | | | | | | | | | | | | | x | x | x | x | x |
| | C, G | | | | | | | | | | | | | | | | | | | | | | | |
| | G, G | | | | | | | | | | | | | | | | | | | | | | | |
| IGF2BP2 rs4402960 | T, T | | | | | | | | | | | | | | | | | | | | x | | | |
| | G, T | | | | | | | | | | | | | | | | | | | | | x | x | |
| | G, G | | | | | | | | | | | | | | | | | | | | | | | |
| TCF7L2 rs7903146 | T, T | | | | | | | | | | | | | | | | | | | | | | | |
| | C, T | | | | | | | | | | | | | | | | | | | | | | | x |
| | C, C | | | | | | | | | | | | | | | | | | | | | | | |
| RESULTS | | f | f | f | f | f | f | f | f | f | F | f | f | f | f | f | f | f | f | f | f | f | f | F |

| Order of Decision | | 1 | 2 | 3 | 4 | 5 | 6 | 7 | 8 |
|---|---|---|---|---|---|---|---|---|---|
| FTO rs9939609 | T,T | x | | | | | | | |
| | A,T | | x | | | | | | |
| | A,A | | | | | | | | |
| Waist Circumference | High | x | x | | x | | x | | x |
| | Normal | | | x | | x | | x | |
| Diabetes subtype beta-cell category | Yes | | | x | x | | | | |
| | No | | | | | x | x | x | x |
| Blood Pressure Category | Normal | | | | | x | x | | |
| | High | | | | | | | x | x |
| RESULTS | | P++ | P++ | P++ | P++ | p | p | P+ | P+ |

FIGURE 14A

| # | Name | Food Group | Description |
|---|---|---|---|
| 1 | Adzuki Beans | Legumes | Adzuki beans offer lots of protein with not much fat, plus potassium, iron, magnesium, zinc, and fiber. These small, reddish brown beans can appear in savory dishes or sweet desserts. |
| 2 | Almonds | Fat | Almonds have fiber and magnesium, and lend crunch to all kinds of recipes, but they're also great by the handful, whether you keep some in your hiking bag or a drawer at your office. |
| 3 | Amaranth | Starch | Amaranth boasts fiber, iron and magnesium. Its tiny, nutty kernels can work as a gluten-free swap for pasta or rice, and can lend thickness to sauces and soups. |
| 4 | Asparagus | Non starchy vegetable | Asparagus can add vitamin C and folate. The tender vegetable sprouts several inches up from the earth in spring, and is great sautéed, grilled or tossed into salad. |
| 5 | Avocado | Fat | The fats in avocados are mostly monounsaturated, which are among the better kinds to get, and these giant berries also throw in some potassium. Avocado is great in a salad or dip, and nicely complements all kinds of savory dishes. |
| 6 | Beef | Lean meat | Beef comes in many forms, some fattier than others, but generally with ample protein and vitamins B6 and B12. We use it in recipes like beef chili, a Thai bowl, or steak and rice salads. |
| 7 | Black Beans | Legumes | Black beans can provide protein without much fat, and also include potassium, iron, fiber, and magnesium. We like them in recipes from chili to Thai noodle bowls. |
| 8 | Black-Eyed Peas | Legumes | Black-eyed peas have iron, fiber and magnesium. Traditionally served next to greens, cornbread or rice, they represent a species known as "field peas" or "cowpeas." |
| 9 | Blueberries | Fruit | Blueberries are a sweet way to get vitamin C and fiber. Besides pairing nicely with other fruit as well as nuts, blueberries can be delectable on cereals or in baked treats. |
| 10 | Bok Choy | Non starchy vegetable | Leafy green bok choy has nutrients like vitamin C, and a flavor that plays nicely in salads, stir-fry or soup. This Chinese cabbage is sometimes also known as pak choi. |
| 11 | Broccoli | Non starchy vegetable | Broccoli provides vitamin C, folate and fiber with little in the way of calories. While there are lots of ways to work it into a meal, if you're trying to fit more vegetables in throughout your day, broccoli can be particularly handy and filling as a snack. |
| 12 | Brown Rice | Starch | Magnesium and fiber both appear in brown rice, which keeps most the original plant kernel, minus an inedible hull. We use it as a salad base and serve it alongside all kinds of protein. |
| 13 | Buckwheat | Starch | Buckwheat has magnesium and fiber, and despite the name, it's not a kind of wheat – meaning it's gluten-free. We like it as a salad base, and also in our soba noodles. Buckwheat's small, nutty-tasting seeds are known as groats. |
| 14 | Buttermilk | Low fat dairy | Buttermilk includes calcium and potassium, and is especially handy when baking, say, buttermilk biscuits. It's worth noting that there are a few kinds – one being the leftovers from churning butter – but we mean low-fat milk cultured into creaminess. |
| 15 | Butternut | Starch | Butternut squash features fiber and vitamins A and C. It's great baked, on salads, and in soups, |

FIGURE 14B

| | | | |
|---|---|---|---|
| 16 | Squash | Non starchy vegetable | pastas and risotto dishes. While summer squash is picked when the skin is still soft and edible, winter squash has time to form a hard rind outside. |
| 17 | Carrots | Non starchy vegetable | Carrots have potassium, vitamin A and fiber. Their orange hue owes to a nifty kind of plant nutrient called carotenoids, with cool upsides like turning into vitamin A in your body. While carrots are tasty on salads and in a variety of dishes, they're handy for snacking too. |
| 18 | Cauliflower | Non starchy vegetable | Cauliflower has vitamin C, as well as potassium and folate. The breadth of its culinary applications may surprise you: It can stand in for potatoes in hash or fritters or even couscous, or find its way into all manner of tasty baked treats. |
| 19 | Chia Seeds | Fat | Chia seeds add omega-3 fats, as well as magnesium, fiber, iron, and calcium. We like them as a subtle addition to foods like berry compote and salad dressing. |
| 20 | Chicken | Very lean meat | Chicken breasts are handy when you want lots of protein without too much fat, and they provide some B6 as well. Because chicken is so deliciously versatile, we use it in dishes from frittata to noodles to salad. |
| 21 | Chickpeas | Legumes | Chickpeas balance protein and carbs, and include some fiber. They're the heart of foods like hummus and falafel. Garbanzo beans, as they're also known, are also great roasted and served on a salad. |
| 22 | Collards | Non starchy vegetable | Collard greens can help you get calcium, fiber and vitamins A and C. They can be stewed slowly or swiftly sautéed, and swap elegantly for lettuce. |
| 23 | Eggs | Medium fat meat | Sometimes called a "perfect protein," a single large egg delivers quality amino acids, as well as some vitamin D, all while clocking in at a relatively paltry 78 calories. We put eggs to work especially at breakfast, but they're also good alongside soba noodles or a fresh herb salad. |
| 24 | Feta Cheese | Medium fat fat | It doesn't take much feta cheese to get some protein, fat and calcium. It's often great on salads, but we also like it with pasta dishes, sweet potatoes or ancient grains. |
| 25 | Figs | Fruit | Figs boast fiber, chewy flesh and a crunchy seed, and are good in all kinds of recipes, from ambitious entrees to decadent desserts. |
| 26 | Flaxseed | Fat | Flaxseed has magnesium, fiber and key omega-3 fats. We like its nutty flavor sprinkled on top of vegetables or cereal, or as a throw-in bonus in muffins and smoothies. |
| 27 | Garlic | Non starchy vegetable | Because of garlic's strong reputation in areas like immune function and heart health, many nutritional products seek to capture its key benefits. One thing's for sure: It only takes a smidge to lend outsize flavor to a variety of dishes. |
| 28 | Goat Cheese | Full fat dairy | Goat cheese can be a fine way to get protein, along with fat and calcium. We like it on salads and snacks, as well as atop toast and in dips. |
| 29 | Grapefruit | Fruit | Grapefruit has fiber and vitamin C, and is tasty sliced, or on salad or even grilled. Grapefruit gets its name for the way it hangs in clusters. |
| 30 | Green Chillies | Non starchy vegetable | Green chillies add a smidge of vitamins C and B6, and can spice up dishes from enchiladas and sandwiches to many dips and, yeah, chili. |

FIGURE 14C

| | | | |
|---|---|---|---|
| 30 | Guava | Fruit | Guava brings potassium, fiber and vitamin C. This tropical green fruit is soft or even creamy when it's ripe, and tastes sweet and tart. Slice it with other fruit or serve it with yogurt. |
| 31 | Hazelnuts | Fat | The fats that hazelnuts contain are mostly unsaturated – often called the "good" kind of fat. Filberts, as they're sometimes known, also have magnesium, and can be enjoyed raw or in sweet dishes, as well as in tasty treats like hazelnut butter. |
| 32 | Kale | Non starchy vegetable | Potassium, fiber, and folate are all in kale, along with vitamins B6, A and C. Among other uses, kale works nicely in salad or a soup, sautéed, or in a green smoothie. |
| 33 | Kidney Beans | Legumes | Kidney beans deliver on protein and fiber. These uh, kidney-shaped beans are reddish brown, and work well with other beans, and are good in everything from chili to tacos. |
| 34 | Lentils | Legumes | Besides being a good source of fiber and iron, a cup of cooked lentils is outstanding for potassium, zinc, magnesium and B6. We like lentils with rice, or on salad or even a frittata. |
| 35 | Medjool Dates | Fruit | Medjool dates bring fiber, magnesium, iron and B6. Replacing the pit of a date with a nut makes for nifty snacking. Sliced dates can also be good with hot or cold cereal, or on salad. |
| 36 | Mozzarella | Lean meat | This cheese is a handy way to get protein and calcium. Part-skim variations can also provide a nice snack if you're avoiding fat. Mozzarella is great on many kinds of salads, as well as sandwiches, baked delights and breakfast recipes like frittatas and burrito bowls. |
| 37 | Mustard Greens | Non starchy vegetable | Mustard greens adds calcium, fiber, vitamin C and some nice peppery pop to salads as well as pasta dishes. Some people prefer to "de-rib" them, taking out the tough bits, but you don't have to, especially if you're sautéing them. |
| 38 | Oats | Starch | Oats offer fiber and zinc. When fortified, they can also provide iron, thiamin, niacin and folate. A frequent inclusion in breakfast cereals, oats are also tasty in many baked goods. |
| 39 | Oranges | Fruit | Oranges deliver on vitamin C and fiber, and are handy on the go since the rind doubles as a built-in wrapper. Oranges also add a citric pop to foods from oatmeal to salad. |
| 40 | Pepitas | Fat | Zinc and fiber are both in pumpkin seeds, otherwise known as pepitas. They're good on soups, salads, baked treats or on their own. |
| 41 | Pinto Beans | Legumes | Iron and fiber are among pinto beans' selling points. They're good in soup or chili, as well as many dishes involving rice or tortillas. |
| 42 | Pistachios | Fat | Pistachios offer fiber, as well as vitamin B6. The green, meaty kernels make for a nice snack, or can lend some crunch mixed in with fruit or a salad. |
| 43 | Portabella Mushrooms | Non starchy vegetable | Portabellas can add riboflavin and niacin, and can also provide vitamin D if they're exposed to ultraviolet light. Portabella caps run to the size of hamburger patties and can be deliciously grilled and served on a bun. |
| 44 | Prunes | Fruit | Prunes come with fiber, potassium and vitamin B6, and can be eaten on their own or atop foods from oatmeal to pancakes to salad. |
| 45 | Quark | Very lean fat | Quark is a simple, creamy cheese; how much fat it brings with its protein can vary. It can also be made at home with just a couple ingredients, and is delicious whether you're fixing a sandwich or |

FIGURE 14D

| | | | |
|---|---|---|---|
| 46 | Queso Fresco | Medium fat fat | Queso fresco is a fine way to get protein and calcium. It doesn't so much melt as crumble, and can be used alongside tortillas or on sandwiches. We particularly like it on a salad with some mixed rice and grains. baking a tart.... We even sometimes use it as a dressing. |
| 47 | Quinoa | Starch | Quinoa has fiber, magnesium and iron. Quinoa's nutty flavor makes it versatile in the kitchen, working as a whole-grain substitute for foods like rice and couscous. |
| 48 | Raspberries | Fruit | Raspberries boast fiber and vitamin C, and besides being great to bake, they're a handy complement to other fruits and nuts. |
| 49 | Red Cabbage | Non starchy vegetable | Red cabbage offers vitamins A, B6 and C. Besides its role in many salads, red cabbage is also quite tasty pickled or in a hash. |
| 50 | Ricotta Cheese | Lean meat | Besides having protein, calcium and vitamins like B12 and A, this soft Italian cheese is tasty – whether you're stirring it into pasta or savoring it in a dessert recipe. |
| 51 | Salmon | Medium fat meat | Besides vitamins D, B6 and B12, salmon contains important omega-3 fats. There are many ways to enjoy this pink, flaky fish – from smoked or grilled to steamed. We especially like salmon caught wild, because it tends to have fewer calories. |
| 52 | Seaweed | Non starchy vegetable | There are many varieties of seaweed with different benefits, from easily sprinkled flakes to the flat, crispy nori that sushi is wrapped in to wakame – seaweed salad. |
| 53 | Sorghum Flour | Starch | Sorghum flour has magnesium, and it swaps nicely for wheat flour in many recipes. This sweet staple of the Old South is poised to make a comeback, partly because it's gluten-free. |
| 54 | Soybeans | Legumes | Soybeans boast an array of nutrients: potassium, iron, calcium, folate, magnesium AND vitamin C. Depending how they're prepared, soybeans can also deliver impressive amounts of protein, suiting them as a meat substitute in tofu. When boiled in the pod and served as an appetizer, they're also known as edamame. |
| 55 | Spinach | Non starchy vegetable | Spinach boasts potassium, iron, calcium, folate, magnesium, B6 and vitamin C. Besides salad, it's good in scrambles, pasta dishes, soup, chili, or green smoothies. |
| 56 | Strawberries | Fruit | A cup of strawberries has vitamin C and fiber, and delivers mouth-watering sweetness for relatively few calories. Strawberries are a treat on their own, or on yogurt, cereal or salad. |
| 57 | Sunflower Seeds | Fat | Sunflower seeds are notable for vitamin E, as well as fiber, zinc and vitamin B6. Besides being a great snack, sunflower seeds can add texture to salads and sautéed veggies. |
| 58 | Sweet Potato | Starch | Sweet potatoes are a delicious way to get potassium, fiber and vitamins B6 and C. They're versatile, too, whether you prefer them baked, grilled, mashed or in a hash. It's worth noting that while they're often called yams, they're not the same thing, as yams have rough skin and are rarely found in produce sections in the U.S. |
| 59 | Swiss Chard | Non starchy vegetable | Swiss chard has potassium and vitamins A and C, plus some magnesium. It can be quickly sautéed or braised, or enjoyed raw. It's sometimes just known as chard, and isn't actually from Switzerland, but further south, along the Mediterranean. |

FIGURE 14E

| | | | |
|---|---|---|---|
| 60 | Turkey | Very lean meat | Besides providing protein without too much fat, turkey breast comes with B6 – and lots of culinary options. Our recipes for it range from chili to breakfast bowls. |
| 61 | Walnuts | Fat | Walnuts include key omega-3 fats, plus magnesium. There are almost as many different walnut types as there are good ways to eat them: They're a delight atop salads or yogurt, or stirred in with vegetables or fruit. |
| 62 | White Beans | Legumes | Beans usually come with iron, potassium, magnesium, decent amounts of protein and not a lot of fat. White beans come in a few different types we're fond of – There's the large Cannellini from Italy, the midsize Great Northern and the compact Navy bean. |
| 63 | White Mushrooms | Non starchy vegetable | These common mushrooms can add riboflavin and niacin without much fat or carbs. They're a nice complement to salads, pizza and pasta, and are also known as button mushrooms. |
| 64 | Yogurt | Low fat dairy | There are many varieties of yogurt with different amounts of protein, fat, calcium and vitamin D, depending what you're after. Yogurt is a fine breakfast food with berries and nuts; we also like it with pancakes or a breakfast stir-fry. |
| 65 | Zucchini Squash | Non starchy vegetable | Zucchini offers vitamin C, as well as some potassium. Zucchini is picked in summertime, when the squash's skin is edible and the white flesh inside is creamy. |

| Biomarkers | Source | |
|---|---|---|
| | MUFA | Fiber |
| Elevated BP | x | x |
| Increased WC/FTO rs9939609 (A;A or A;T)* | | x |
| Low subtype disposition index and elevated/high fasting glucose ** | x | x |
| Low subtype disposition index and impaired glucose tolerance (elevated/high 2h glucose) ** † | x | x |
| Low subtype disposition index and impaired glucose tolerance (elevated/high 2h glucose) & elevated/high fasting glucose** † | x | x |
| Impaired glucose tolerance (elevated/high 2h glucose) & elevated/high-fasting glucose (IFG/IGT) | | x |
| Impaired glucose tolerance (elevated/high 2h glucose) (IGT) | | x |
| Elevated/high fasting glucose (IFG) | | |
| Elevated/strongly elevated fasting TG | x | |
| Abnormal post-prandial TG (30 mins and/or 2 h and/or AUC) | x | |
| Slightly elevated LDL-C | | x |
| Elevated/strongly elevated fasting LDL-C | x | x |
| Increased WC | | x |

Figure 16

| Biomarkers | Protein Need | | |
|---|---|---|---|
| | Normal Protein Need (p) | Increased Protein Need (P+) | High Protein Need (P++) |
| Elevated BP | | Energy - 18-30% | |
| Increased WC/FTO rs9939609 (A;A or A;T)* | | | Energy - 18-35% |
| Low subtype disposition index and elevated/high fasting glucose ** | | | Energy - 18-35% |
| Low subtype disposition index and impaired glucose tolerance (elevated/high 2h glucose) ** † | | | Energy - 18-35% |
| Low subtype disposition index and impaired glucose tolerance (elevated/high 2h glucose) & elevated/high fasting glucose** † | | | Energy - 18-35% |
| Impaired glucose tolerance (elevated/high 2h glucose) & elevated/high-fasting glucose (IFG/IGT) | | | |
| Impaired glucose tolerance (elevated/high 2h glucose) (IGT) | | | |
| Elevated/high fasting glucose (IFG) | | | |
| Elevated/strongly elevated fasting TG | | | |
| Abnormal post-prandial TG (30 mins and/or 2 h and/or AUC) | | | |
| Slightly elevated LDL-C | | | |
| Elevated/strongly elevated fasting LDL-C | | | |
| Increased WC | | | |
| SNP (ADAMTS9 rs4607103) | | | |
| SNP (GCKR rs780094) | | | |
| SNP (FTO rs9939609) | | | |
| SNP (FTO rs1121980) | | | |
| SNP (FADS1 rs174546) | | | |
| SNP (FADS1 rs174548) | | | |
| SNP (TCF7L2 rs7903146) | | | |
| SNP (IGF2BP2 rs4402960) | | | |
| SNP (PPARG rs1801282) | | | |

Figure 17

|  |  | Deficiency | Glucose | | | | | |
|---|---|---|---|---|---|---|---|---|
|  |  |  | IFG | | IGT | | IFG/IGT |
|  | DRI |  | Elevated (100-126 mg/dL) | High (>126 mg/dL) | Elevated (140-200 mg/dL) | High (>200 mg/dL) | Elevated IGF - 126 mg/dL Elevated IGT - 140-200 mg/dL |
| Wholegrain | - | Female 19-50 yrs - 25 g<br>Male 19-50 yrs - 38 g<br>Female > 50 yrs - 21 g<br>Male > 50 yrs - 30 g | 90 g | - | 90 g | 90 g |  |
| Fiber |  |  |  | - | 5 g/100 g Carbs | 5 g/100 g Carbs | 5 g/100 g Carbs |
|  |  |  |  | - | 8 g/100 g Carbs | 8 g/100 g Carbs | 8 g/100 g Carbs |
| Beta-glucans |  |  |  | - | 3.5 g/100 g Carbs | 3.5 g/100 g Carbs | 13.5 g/100 g Carbs |
| Carbs |  |  |  | - | 14 g/100 g Carbs | 14 g/100 g Carbs | 14 g/100 g Carbs |

```
2802 Obtain feature data about a user

2804 Feature data includes a plurality of genotypic markers X = {x₁ ..., xₘ}

2806 Feature data includes a plurality of phenotypes Y = {y₁ ..., yₙ}

2808 The plurality of phenotypes includes one or more metabolic adaptability
    characteristics, optionally identified using a multi-nutrient challenge beverage 2810 Feature data includes a user food preference 2812 Feature data includes an anthropometric characteristic 2814 Feature data includes a user goals 2816 Feature data includes a user dietary pattern 2818 Feature data includes a user activity pattern
```

(A) (B) (C) (D) (E) (F)

2820 Assign a respective diet type $D_j$ in a plurality of diet types $D = \{D_1 ..., D_q\}$ to the user by inputting user features, including a first sub-plurality $X_1$ of the plurality of first features X and a first sub-plurality $Y_1$ of the plurality of second features Y, into a diet type classification model 2822 Assigning a respective diet type includes:
Assigning a macronutrient fat intake recommendation $F_j$ to the user by inputting a third sub-plurality $X_3$ of the plurality of first features X and a third sub-plurality $Y_3$ of the plurality of second features Y into a fat recommendation classification model;
Assigning a macronutrient carbohydrate intake recommendation $C_j$ to the user by inputting a fourth sub-plurality $X_4$ of the plurality of first features X and a fourth sub-plurality $Y_4$ of the plurality of second features Y into a carbohydrate recommendation classification model; and
Assigning a macronutrient protein intake recommendation $P_j$ to the user by inputting a fifth sub-plurality $X_5$ of the plurality of first features X and a fifth sub-plurality $Y_5$ of the plurality of second features Y into a protein recommendation classification model (F) (G) (H)

Figure 28A

2842 Rank one or more foods in a plurality of foods $L = \{N_1 ..., N_t\}$, wherein each respective food $N_i$ in the plurality of foods has a corresponding nutrition profile $PN_i = \{D_{ki}, P(z_{ki})\}$ comprising an assigned diet type $D_k$ in the plurality of diet types D and an assigned micronutrient profile $P(z_k) = \{v(z_1) ..., v(z_s)\}$, wherein the micronutrient profile $P(z_k)$ includes a respective value $v(z_i)$ for each micronutrient $z_i$ in the plurality of micronutrients Z

2844 Deprioritizing a food $N_i$ that does not conform to a user preference

2846 Deprioritizing includes assigning the food a lower rank in the ranking of the one or more foods in the plurality of foods L

2848 Deprioritizing includes removing the food from a list of eligible foods for the user, e.g., the plurality of foods

2850 Prioritizing foods N by comparing the diet type $D_j$ assigned to the user with the diet types $D_k$ assigned to each food $N_i$

2852 Prioritizing includes assigning a food $N_1$ having a same diet type $D_{k1}$ as the diet type $D_j$ assigned to the user a higher rank in the ranking of the one or more foods than a food $N_2$ having a different diet type $D_{k2}$ as the diet type $D_j$ assigned to the user

2854 Prioritizing includes removing a food $N_3$ having a different diet type $D_{k3}$ as the diet type $D_j$ assigned to the user from a list of eligible foods for the user, e.g., the plurality of foods

2856 Deprioritizing a food $N_i$ that does not conform to a user allergy and/or sensitivity

2858 Deprioritizing includes assigning the food a lower rank in the ranking of the one or more foods than a food that does conform to the user allergy and/or sensitivity

2860 Deprioritizing includes removing the food from a list of eligible foods for the user

2862 Deprioritizing foods N by comparing the source recommendation $S_j$ assigned to the user with the nutrition profile $P_N$ of each food $N_i$

2864 Deprioritizing includes assigning a food $N_1$ that does not conform to a user source recommendation a lower rank in the ranking of the one or more foods than a food $N_2$ that does conform to a user source recommendation

2866 Deprioritizing includes removing a food $N_1$ that does not conform to a user source recommendation from a list of eligible foods for the user

2868 Prioritizing foods N by comparing the micronutrient recommendation profile $R_j$ assigned to the user with the micronutrient profile $P(z_{ki})$ assigned to each food $N_i$

2870 Prioritizing includes assigning, within a diet type $D_k$, a food $N_1$, having a micronutrient profile $P(z_{k1})$ that more closely matches the user's micronutrient recommendation profile $R_j$ than the micronutrient profile $P(z_{k1})$ of a food $N_2$ having the same diet type as food $N_1$, a higher ranking than food $N_2$

2872 Deprioritizing (e.g., further lowering a ranking of) a food $N_1$ having a lower ranking than a food $N_2$ when food $N_1$ and food $N_2$ belong to a same food family

2874 Deprioritizing a food $N_i$ by comparing a supplement recommended to the user to the nutrition profile $P_N$ of each food N

2876 Deprioritizing includes lowering the ranking of food $N_1$ that is rich in a nutrient present in the supplement recommended to the user

2878 Deprioritizing includes removing a food $N_1$ that is rich in a nutrient present in the supplement recommended to the user from a list of eligible foods for the user (J)

Figure 28E

2912 Providing the user with a food recommendation

2914 The food recommendation is based on a diet type $D_j$ assigned to the user

2914 The food recommendation is based on a micronutrient recommendation profile $R_j$ assigned to the user 2916 The food recommendation is based on a source recommendation $S_j$ assigned to the user 2918 The food recommendation is based on a hero food recommendation $H_j$ assigned to the user 2920 The food recommendation is based on a supplement recommendation $V_j$ assigned to the user 2922 The food recommendation is based on a caloric recommendation $C_j$ assigned to the user

Figure 28H

SYSTEM AND METHOD FOR IMPLEMENTING MEAL SELECTION BASED ON VITALS, GENOTYPE AND PHENOTYPE

CROSS REFERENCE TO RELATED APPLICATIONS

This application is a Continuation of U.S. patent application Ser. No. 15/792,673, filed Oct. 24, 2017, which claims priority to U.S. Provisional Patent Application No. 62/412,114, filed Oct. 24, 2016, the disclosures of which are hereby incorporated by reference, in their entireties, for all purposes.

FIELD OF THE INVENTION

The disclosed embodiments relate generally to health diagnostic systems and methods, and in particular, to recommending meals, recipes, foods and/or supplements based on a person's vitals, genotypic and phenotypic data.

BACKGROUND OF THE INVENTION

Diet is a major factor in the health of individuals. Advice on what to eat is prevalent today. The advice tends to be general in nature and focuses on which foods to avoid, such as processed foods or saturated and trans fats, or which foods to eat more of, such as fruits, vegetables and whole grains. Certain health conditions or diseases have also led to recommendations to avoid or to eat certain foods. However, within other subgroups of people, such as people with diabetes, there have not been individualized nutritional recommendations. Moreover, even where nutrition recommendations have been identified for individual disease states, genotypes, or phenotypes, comprehensive dietary recommendations have not been developed that consider the interplay between multiple features of an individual.

U.S. Patent Application Publication No. 2012/0130732, for example, describes methods and systems for providing personalized nutrition and exercise advice to a subject. However, the methods consider subject features individually, rather than together. For example, as illustrated in FIG. 3, identification of low serum ferritin levels in an individual result in a monotonous static recommendation to eat red meat and liver, take iron supplements, swim, and exercise less often. This advice does not consider, however, how the interplay of other features of the subject affect the recommendations provided. This publication also does not comprehensively evaluate a user's genetics, phenotypical and other information about a user to produce diet types for macronutrient recommendations or combine macronutrient and micronutrient needs of a user into daily, weekly, or other frequent meal, food, or supplement recommendations that exhibit variety and that are ranked for a user and that also may output recipes, or supplement regimens.

U.S. Patent Application Publication No. 2012/0295256, for example, describes methods and systems for providing weight management advice by considering features associated with weight management. However, the methods only consider recommendations related to weight management, without considering other health considerations.

U.S. Patent Application Publication No. 2013/0280681, for example, describes methods and systems for providing food selection recommendations based on a user's dietary history. However, the methods do not consider the biological differences between individuals that inform healthy eating.

Recent studies suggest that healthy individuals have greater metabolic adaptability which facilitates phenotypic flexibility to changing environmental conditions, including stressors (e.g., physical activity). van Ommen B. et al., Genes Nutr., 9(5):423 (2014). For example, impaired phenotypic flexibility has been reported in overweight participants who may have reduced ability to metabolize stored lipids for energy synthesis and in response, slowly adapt to excess dietary fat intake, compared with lean participants. Blaak E. et al., J Clin Endocrinol Metab, 91:1462-69 (2006). Further, the lack, or excess, of consumption of certain dietary components, are known to impair phenotypic flexibility and may ultimately affect optimal health. van Ommen B. et al., Supra. The assessment of phenotypic flexibility involves the perturbation of homeostasis and subsequent evaluation of specific nutrition-related biomarkers. Challenge tests with various combinations of macronutrients have been used to temporarily disturb homeostasis (Stroeve 2015; Kardinaaal 2015; van Amelsvort 1989). However, these tests are inconvenient, typically requiring an individual to visit a testing center to perform a lengthy test.

Comprehensive analyses of an individual's genotypic and phenotypic characteristics are not performed for the purpose of recommending personalized meals or foods. As such, there remains a need for specific techniques to analyze information for individuals and help individuals to determine what they should eat. There remains a further need for the nutritional recommendations to reflect comprehensively a person's individuality and goals.

SUMMARY OF THE INVENTION

Various embodiments of systems and methods within the scope of the appended claims each have several aspects, no single one of which is solely responsible for the attributes described herein. Without limiting the scope of the appended claims, after considering this disclosure, and particularly after considering the section entitled "Detailed Description," one will understand how the aspects of various embodiments are used to enable specific personalized nutrition systems and methods.

The disclosed systems and methods use data from individual users, including their vitals data, such as waist circumference, blood pressure and age; genotypical data including data on a user's DNA and genetic variations such as particular single nucleotide polymorphisms (SNPs), and phenotypical data relating to markers obtained from blood samples from the individual. By focusing on these and other types of data associated with a person's body, rules and logic may be applied to classify individuals into specific diet types that specify at the macronutrient and micronutrient level a personalized diet and also what foods should be eaten by the person. Moreover, with the addition of personal goals as well as food preferences, a list of available meals, recipes, hero foods, snacks or supplements can be selected, customized, prioritized, and delivered for each user within a community of users that is tailored to the well-being of each user and that delivers a variety of healthy, different, and interesting food recommendations on a daily, weekly, monthly, or other frequent basis and that introduces healthy meal variation for each user over time. In this manner, a user or each user in a population of users is provided a variety of different prepared meals that may be delivered to the user, recipes that may be prepared by the user, food recommendations or supplement recommendations, all in order to help the user on a daily, weekly, monthly, or other frequent basis achieve a desired state of wellbeing or one or more health goals through healthy and personalized consumption.

According to some embodiments, a system for recommending foods to a user based on health data, comprises a database, a memory and a processor. The database stores user health data for each user within a community of users, including vitals, genotypical and phenotypical data, user food preference data and foods data that includes macronutrient and micronutrient data for foods that may be recommended to a user. The memory stores program instructions, including program instructions that are capable of implementing (i) decision tree logic that classifies user health data into predetermined diet types and micronutrient recommendations, (ii) a filtering engine to filter the food data to determine available foods for a user based on the user's diet type and the user's food preference data; and (iii) a ranking engine that ranks available meals for the user based on the micronutrient recommendations and the food data. The processor is coupled to the database and the memory and, when executing the program instructions, causes the decision tree logic to classify the user by diet type and nutrient recommendations, causes the filtering engine to determine available foods for the user and causes the ranking engine to rank and translate the micronutrient recommendations and the food data for the available foods for the user into specific food recommendations for the user.

According to some embodiments, the recommended foods are prepared meals. According to some embodiments, the recommended foods may be one or more of the following: prepared meals, recipes, snacks, hero foods, which are foods high in certain nutrients of value to users, or nutritional supplements. The health data in some embodiments may include activity levels for at least some users. The health data may further include in some embodiments user goals such as weight loss or endurance that are used by the filtering engine or the ranking engine to select foods for the user. The food data may also include calorie information used by the filtering engine or the ranking engine to select foods for the user. The system may also makes lifestyle recommendations to the user to improve the user's wellbeing based on the health data.

The vitals used by the system in some embodiments include waist circumference and blood pressure and may further include age, gender, height, weight, activity level and other information about a user.

The genotypical data in some embodiments includes genetic variants including single nucleotide polymorphisms that are correlated with one or more of the following: body fat, blood pressure, heart health and inflammation among other data. The phenotypical data in some embodiments includes information on some or all of the following: the user's insulin sensitivity, cholesterol, triglycerides, and nutrient and mineral levels, among other data. The user's food preference data in some embodiments includes information on foods that the user will not eat or the user's food religion, such as vegan or kosher.

In some embodiments, a method for recommending foods to a user based on health data, includes maintaining a database of users that stores (i) for at least some users, a diet type vector for each user comprising macronutrient and micronutrient ranges determined based on decision logic from the user's health data, including vitals, genotypical and phenotypical data, (ii) user food preference data, and (iii) food data including macronutrient and micronutrient data corresponding to foods that may be recommended to a user. At the request of a requesting user, the method includes filtering the food data based on the user's diet type vector and the user food preference data to determine a set of available foods for the user. A food is excluded from the list of available foods for the requesting user if the food does not match the requesting user's preference data. In some embodiments, the method includes presenting to the requesting user the list of available foods matching the user's diet type. The list of matching foods may also be ranked based on the micronutrients in the user's diet type vector and the food data corresponding to the matching foods. Many other factors may also be used to influence the ranking.

In one aspect, the disclosure provides a multi-nutrient challenge beverage for measuring the metabolic adaptability of a user, including: a) from 44 to 57 grams total fats; b) 75±15 grams total carbohydrates; and c) 20±3 grams total protein.

In some embodiments of the multi-nutrient challenge beverage described above, the fat content of the beverage comprises from 10% to 20% of the total weight of the beverage.

In some embodiments of the multi-nutrient challenge beverages described above, the fat content of the beverage is primarily from an edible vegetable oil.

In some embodiments of the multi-nutrient challenge beverages described above, the edible vegetable oil is palm oil.

In some embodiments of the multi-nutrient challenge beverages described above, the carbohydrate content of the beverage comprises from 10% to 30% of the total weight of the beverage.

In some embodiments of the multi-nutrient challenge beverages described above, the carbohydrate content of the beverage is primarily from monosaccharide sugar.

In some embodiments of the multi-nutrient challenge beverages described above, the monosaccharide sugar is dextrose.

In some embodiments of the multi-nutrient challenge beverages described above, the protein content of the beverage comprises from 2.5% to 10% of the total weight of the beverage.

In some embodiments of the multi-nutrient challenge beverages described above, the protein content of the beverage is primarily from a milk protein isolate.

In some embodiments of the multi-nutrient challenge beverages described above, the beverage further including one of more of a tastant, an emulsifier, a thickening agent, and a preservative.

In one aspect, the disclosure provides a method for measuring the metabolic adaptability of a user, including: (A) obtaining data on a user's blood insulin levels, blood glucose levels, and blood triglyceride levels prior to consumption of a multi-nutrient challenge beverage, after a first period of time following consumption of the multi-nutrient challenge beverage, and after a second period of time following consumption of the multi-nutrient challenge beverage; and (B) inputting the obtained data into a metabolic adaptability classifier, wherein the first period of time and second period of time following consumption of the multi-nutrient challenge beverage are each no longer than 120 minutes, and wherein the challenge beverage is a challenge beverage as described above.

In some embodiments of the method for measuring the metabolic adaptability of a user described above, the data obtained on the user's blood insulin levels, blood glucose levels, and blood triglyceride levels is derived from a dried blood sample collected by the user.

BRIEF DESCRIPTION OF THE FIGURES

So that the present disclosure can be understood in greater detail, a more particular description may be had by reference to the features of various embodiments, some of which are illustrated in the appended drawings. The appended drawings, however, merely illustrate the more pertinent features of the present disclosure and are therefore not to be considered limiting, for the description may admit to other effective features.

FIG. 3 is a list of phenotypic data that is used in accordance with some embodiments for processing a user's diet type.

FIG. 4 is a list of genotypic data that is used in accordance with some embodiments for processing a user's diet type.

FIG. 6 depicts an illustrative set of ranges for seven individualized diet types into which to categorize users based on their vitals, genotype and phenotype in accordance with some embodiments.

FIG. 7 depicts an illustrative collection of food groups and serving sizes for seven different diet types in accordance with some embodiments.

FIG. 8 is a list of micronutrients and in some cases foods that are used in accordance with some embodiments for determining micronutrient recommendations and meal or food ranking in accordance with some embodiments.

FIGS. 11A and 11B depict an illustrative classifier for determining a carbohydrate recommendation based on vitals, genotypic and/or phenotypic data in accordance with some embodiments.

FIGS. 12A, 12B, and 12C depict an illustrative classifier for determining a fats recommendation based on vitals, genotypic and/or phenotypic data in accordance with some embodiments.

FIG. 13 depicts an illustrative classifier for determining a protein recommendation based on vitals, genotypic and/or phenotypic data in accordance with some embodiments.

FIGS. 14A, 14B, 14C, 14D, and 14E depict a list of hero foods that are recommended to users in some embodiments.

FIG. 16 depicts an illustrative classifier for determining monounsaturated fatty acid and fiber recommendations based on vitals, genotypic and/or phenotypic data in accordance with some embodiments.

FIG. 17 depicts an illustrative classifier for determining dietary protein flexibility recommendations based on vitals, genotypic and/or phenotypic data in accordance with some embodiments.

FIG. 18 depicts an illustrative classifier for determining dietary carbohydrate flexibility recommendations based on vitals, genotypic and/or phenotypic data in accordance with some embodiments.

FIG. 19 illustrates insulin levels in subjects before and after consuming a multi-nutrient challenge beverage, as measured using capillary blood samples spotted on a substrate (insulin ADX) and venous blood collected in a catheter (insulin venous).

FIG. 20 illustrates a linear regression comparing insulin levels measured using capillary blood samples spotted on a substrate (insulin ADX) with venous blood collected in a catheter (insulin venous) before and after consuming a first multi-nutrient challenge beverage.

FIGS. 28A, 28B, 28C, 28D, 28E, 28F, 28G, and 28H are a flow chart illustrating a method of providing food recommendations based on the features of a user in accordance with some embodiments.

Figure 1:
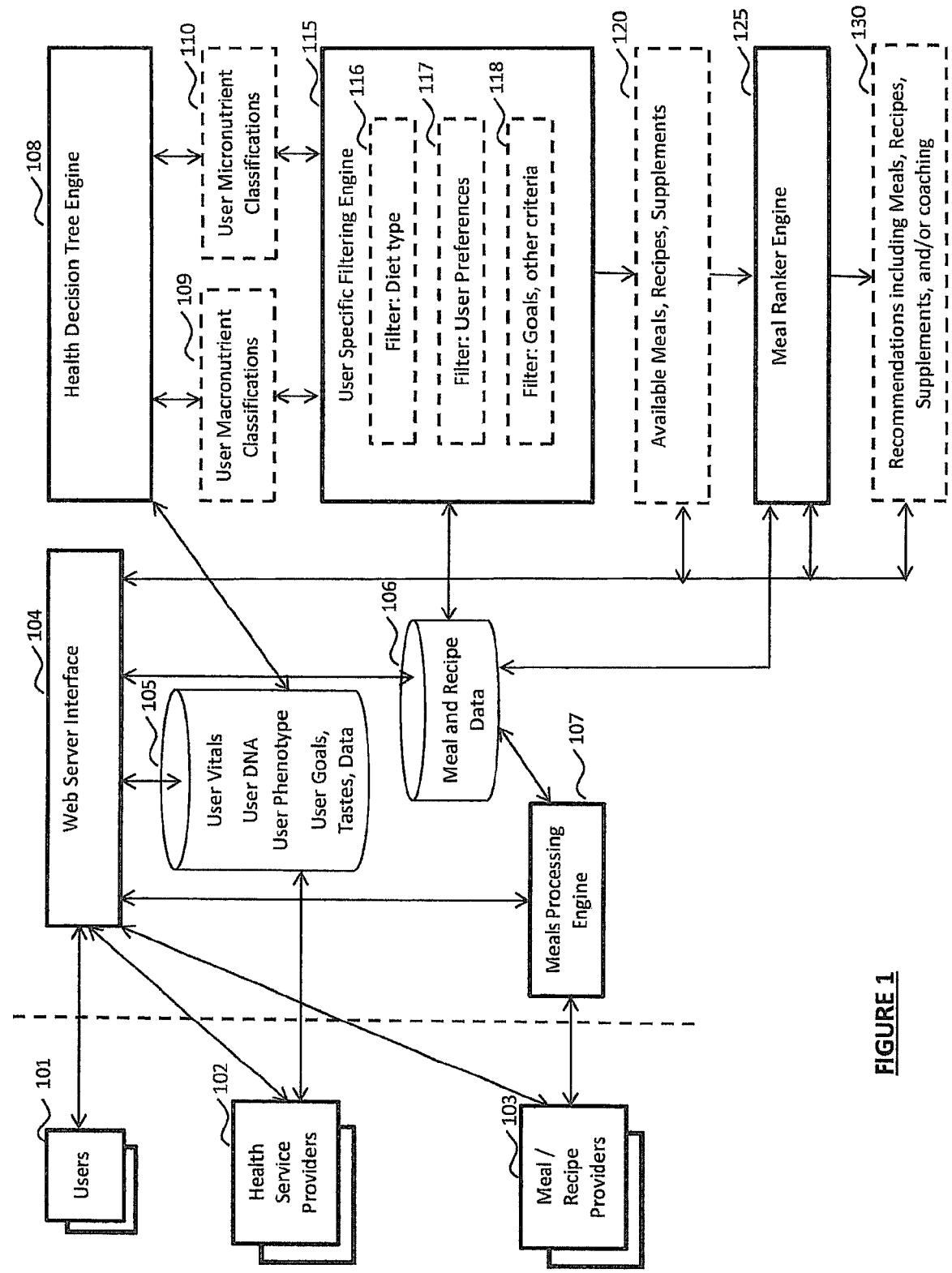
FIG. 1 is a block diagram illustrating an implementation of a personalized food and nutrition recommendation system, in accordance with some embodiments.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Overview

The various implementations described herein include systems, methods and/or devices used to enable individualized meal and food recommendations to a user based on that user's health vitals, such as height, weight, blood pressure, age, waist circumference; the user's genotype and in particular genetic markers, such as SNPs, and phenotype data as determined by blood tests.

The disclosed systems and methods use data from individual users, including their vitals data, such as waist circumference, blood pressure and age; genotypical data including data on a user's DNA and genetic variations such as particular single nucleotide polymorphisms (SNPs), and phenotypical data relating to markers obtained from blood samples from the individual. By focusing on all three types of data associated with a person's body, rules and logic may be applied to classify individuals into specific diet types that specify at the macronutrient and micronutrient level a personalized diet and also what foods should be eaten by the person. Moreover, with the addition of personal goals as well as food preferences, a list of available meals, recipes, hero foods, snacks or supplements can be selected, customized and prioritized for each user. In this manner, a user is provided prepared meals that may be delivered to the user, recipes that may be prepared by the user, food recommendations or supplement recommendations in order to help the user achieve a desired state of wellbeing or one or more health goals.

Systems of the Invention

FIG. 1 depicts a block diagram of a system 100 according to some embodiments of the invention. The system implements personalized nutrition analysis for a user and facilitates identifying meals, recipes, and foods or supplements (collectively foods) for users and may further facilitate selling and delivering meals and other foods to users. Referring to FIG. 1, the system 100 includes a plurality of users at user devices 101 that communicate with a server, such as a web server interface 104, typically via a network. The network may include the Internet, local area networks, wide area networks, wired networks, optical networks, wireless networks, telephone networks, cellular networks, email networks and any other type of network or bus connection that allows the exchange of data typically, though not limited to, through the Internet Protocol. The user devices 101 may be mobile devices, such as mobile phones, tablets, or laptop computers, for example. Alternatively, the devices 101 may be desktop or other computers or devices. The user devices 101 enable a plurality of users to interact with the web interface server 104 to provide information about the user to the web server 104 and to receive information back from the web server interface 104. Generally, the user devices 101 includes a processor, memory, a screen, and input devices such as a touchscreen, keyboard, keys, a mouse, or a microphone. The user interacts with the user device 101 and the web server interface 104 to exchange information between the system 100 and the user 101.

The system 100 also may include devices 102 associated with health service providers and devices 103 associated with meal, recipe or supplement providers. The devices 102 and 103 are similar to the user devices described above. The system 100 further includes a user health database 105, a meal and recipe database 106 and a meals processing engine 107.

The user devices 101 may be used by users to provide health information about themselves to the system 100. In particular, in some embodiments, the user may log into the web server interface 104 and upon authentication provide to the system 100 information about the user's vitals, such as the information shown in FIG. 1. The user may further provide genotype and phenotype information, for example, of the types shown in FIGS. 3 and 4. The user may in some embodiments also provide information about the user's goals, such as general wellbeing, weight loss, increase of muscle mass and/or improving endurance. The user may also in some embodiments provide information about the food preferences, for example food religion (e.g., vegan, kosher, gluten free), or a list of foods that the user prefers or does not like. This information may be elicited through a browser interface with questions or lists of questions with dropdown predetermined choices according to some embodiments.

The devices 102 may be used by health service providers to provide vitals, genotype or phenotype information regarding the user to the system 100. In general, the user and/or healthcare providers may enter or upload data via the web server. Alternatively, the user and or health service providers may upload the data for particular users directly to a database associated with the system 100, such as the database 105. The database 105 may be centralized or distributed and accessible by the system 100.

In general, the webserver 104 and devices 101 and 102 are used for inputting data about each user's vitals, genotype and phenotype. The web server interface 104 may serve a browser page that authenticates users and/or health service providers and allows them to enter relevant data into particular fields. Alternatively, the web server interface may facilitate uploading files to the database 105 or otherwise facilitating access to the database 105 to provide relevant information about users to the system. The web server interface 104 may further include parsing and filtering functionality that receives data on the vitals, genotypes and phenotypes of users and converts the data into a recommendation context with data populating fields that will be used by the system 100 for nutritional analysis according to some embodiments described herein. Similarly, goals and food preference information may be filtered and stored in the database 105.

Additional devices that interact with the system 100 may be coupled to the system, including in some embodiments devices 103. Devices 103 may be associated with meal, recipe or health supplements providers (hereinafter meal providers). The meal providers may provide meals, recipes or supplement information to the system to be stored in the meal and recipe database 106. The devices 103 may provide meal related information to the meal and recipe database 106 via the web server interface through browser entry, through uploading data via the web server interface 104 or via the meals processing engine 107.

The devices 101 may further include activity trackers associated with a user that provide additional information about users to the system 100. For example, in some embodiments, activity trackers may provide daily information about how many calories a user has burned, how much sleep a user has gotten, how many steps a user has taken, heart rate information, distance walked or run. In some embodiments, other information about the user's activities may be provided such as the type of activity done by the user and the duration, such as swimming for one hour. The user's device may automatically upload activity information or may upload it in response to synchronization operations initiated by the user. Additionally, the user may provide activity level, sleep and other data about the user to the system 100 via a webpage served by the web server interface 104 by uploading or linking a file with activity data.

The meals processing engine 107 receives data from the web server interface 104 or the devices, such as devices 103 regarding meals, recipes or other foods or supplements and converts the data into a format usable by the system 100 and then stores the data in the database 106. In general, the information regarding meals and recipes includes in some embodiments the number of calories associated with the meal and macronutrient information, such as the calories from protein, fat and carbohydrates. The meal information in some embodiments includes the number of grams of fat, protein and carbohydrates. In some embodiments, the meal and food information includes amounts associated with micronutrients, such as vitamins, or dietary fibers, or types of fats such as saturated, monounsaturated, or polyunsaturated fats. The data associated with foods, meals and/or recipes in terms of macronutrients and micronutrients may be directly provided to the database 106 or may be converted by a conversion process in the web server interface 104 or meals processing engine 107 in some embodiments into actionable macronutrient and micronutrient information. Similarly, hero foods, snacks or supplements may be described to the system in terms of micronutrient and other macronutrient information by the same processes describe above.

The web server interface 104 may maintain a user profile for each user. The user profile may include, for example, some or all of the following information:

User Number, User id, Password, biometric data
User location or shipping address, billing address or credit card information
User email address or telephone number at which to receive messages
User meal delivery data (daily, weekdays, # meals per week, monthly, breakfast, lunch, dinner, snack, supplement)
User offer preferences (offer user recommended meals every day by messages, weekly, monthly, other frequency)
User activity tracker information
User organization affiliation
User diet type classification
User goals and food preferences
User coaching preferences The system 100 in some embodiments processes the information received from users and providers to produce recommendations for meals, recipes and supplements. The web interface server 104, for example, includes information on each user in the user profile. The user profile may specify, for example that a user is to be given a meal recommendation for each meal three times a day. Alternatively, the user profile may specify only one meal a day or five meals a week. The profile may also call for delivery of the meals or alternatively recipe recommendations according to some embodiments. Additional details of how the system may be configured for users is discussed below.

The system 100 determines foods for users, including in some embodiments prepared meals, recipes, snacks, hero foods, supplements or some or all of the foregoing. In some embodiments, the determination is made in real time on request by a user. In some embodiments, the system 100 determines meals for users at some frequency determined by a user selecting from available options. When the web server interface 104 determines that the system is ready to identify recommended meals for a user the recommendation process starts. This process uses the decision tree engine 108 to produce macronutrient 109 and micronutrient 110 classifications for each user, which result in each user being classified in one of several possible diet types. Each diet type specifies ranges for protein, fats and carbohydrates as shown in FIG. 6. The ranges may be specified in grams or as percentages of calories.

The macronutrient 109 recommendations and the meal and recipe database 106 are inputs to a user specific filtering engine 115. The filtering engine 115 filters meal data based on the user's macronutrient classifications or diet type. The filtering engine may also filter the meals and recipes based on the user's goals, or food religion or food preferences. For example, if the user does not like fish, meals with fish will be excluded by the filter. Similarly, users whose food religion is vegan will have meals and recipes that include meat filtered out. When goals such as weight loss are factored in, certain meals may be filtered out based on calories or macronutrient factors, including those specific to the user. The result of the filtering engine 115 is a set of available meals, recipes or supplements for the user, sometimes referred to as the available meals 128.

The meal ranker engine 130 receives the available meals as well the user's macronutrient 109 classifications or diet type, and micronutrient 110 classifications. The meal ranker engine may also receive the following information from the databases 105 and 106:

Data on calories, macronutrients and micronutrients for each meal, recipe, food or supplement
Data on diet type, macronutrient and micronutrient recommendations for each user
Goals and user preference information The meal ranker algorithm outputs recommendations for one or more users. The meal ranker algorithm may rank meals, recipes, supplements, hero foods, snacks or other information. The meal ranker algorithm may take into account other user meals in a day or supplements that the user regularly takes. It may also take into account the activity level of the user, in addition to macronutrient and micronutrients.

Figure 2A:
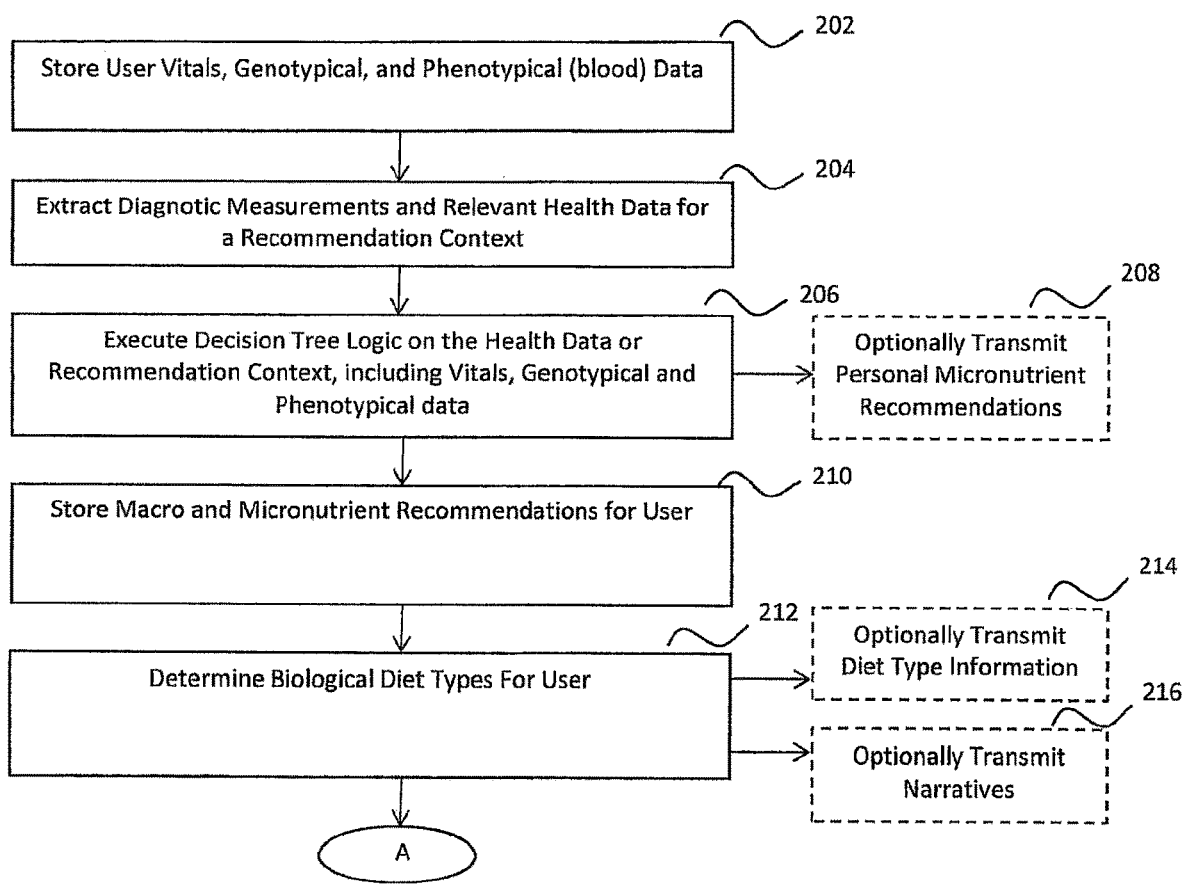
FIG. 2A is a flow chart illustrating a method of processing user vitals, genotypical and phenotypical data to determine a diet type for a user in accordance with some embodiments.

FIG. 2 depicts a method 200 of determining a diet type and a micronutrient recommendation for a user based on vitals, genotypical and phenotypical data. Referring to FIG. 2, according to the method user vitals, genotypical and phenotypical data are stored for a user in 202. The vitals data includes information specific to the user, including, for example, the following information: age, sex, waist circumference (size or high/medium/low), and blood pressure measurements. The phenotypical data is based on blood work done on the user. The phenotypical information may include the data set forth in FIG. 3. In some embodiments, the user is given a challenge beverage and samples of the user's blood are taken at different times before and after drinking the challenge beverage. The challenge beverage is described in more detail in the Challenge Beverage section. In general, the phenotypical data provides information about the user's metabolic health, insulin sensitivity, heart health, micronutrient levels, cholesterol and triglyceride levels and inflammation. The genotypical markers in some embodiments are those indicated in FIG. 4. In some embodiments, the genotypical markers are single nucleotide polymorphisms (SNPs) that have a bearing on, for example, gluten sensitivity, endurance performance, blood pressure and sodium, insulin sensitivity, heart health, and inflammation. More, fewer or different SNPs may be used as compared to the ones identified in FIG. 4. The vitals, phenotypical and genotypical data may be uploaded to the system by a user or health care provider. Once the data is uploaded, for example into database 105, then in 204 individual data elements may be stored as part of a recommendation context for the user. Diagnostic measurements, which may be combinations of data elements from the vitals, genotypical and phenotypical data, may also be determined and stored in connection with a user as part of the recommendation context for the user. In general, the recommendation context includes actionable data related to a user's genotype, phonotype and vitals that are to be used to determine the user's diet type, macronutrient and micronutrient recommendations, which in turn form the basis of meal, recipe, food and supplement recommendations.

In 206, decision tree logic is used on the recommendation context, including the vitals, genotype and phenotype information. The decision tree logic classifies the user according to specific rules specified herein that result in diet type, macronutrient and micronutrient recommendations. The diet type, macronutrient and micronutrient classifications are based not just on one piece of information. Rather, they are based on combinations of genotypical, phenotypical and vitals information. In some embodiments, the diet type, macronutrient and micronutrient classifications may also factor in the user's goals and activity levels.

The decision tree logic presents a specific implementation of determining diet types, macronutrient and micronutrient recommendations. The decision trees operate based on input from vitals, genotypical and phenotypical information for each user and are a particular application of rules that classify users into at least one of several diet types and recommended micronutrient levels. The diet types then become the basis for meal and recipe recommendations.

In 208 the system may optionally transmit the personalized diet type, macronutrient and micronutrient information to the user. The information may be part of a recommendation to supplement the user's diet with particular hero foods or particular vitamin supplements or part of a narrative or set of coaching instructions for the user. In 210, the macronutrient and micronutrient information is stored for the user.

In 212 the diet type is determined for the user and may be stored in the database 105 in association with the user. The diet type may be determined in 212 directly from macronutrient information. Alternatively diet type may be determined based on mapping one or more macronutrient recommendations or one or more macronutrient and micronutrient recommendations to a set of predetermined diet types for the system. For example, the macronutrient recommendation may be broken down into eight combinations: Fats (f and F), Carbohydrates (c and C), and Protein (p and P). The upper case letter designation refers to an increased level as compared to the lower level. The table below shows an example of mapping sets of macronutrient recommendations to five diet types or diet type vectors.

TABLE 1

Description of illustrative diet types.

| Diet Type | F/C/P | Description |
| --- | --- | --- |
| Balanced Harvester | FCP | High carb, medium fat, medium protein |
|  | FCp |  |
| Grain Seeker+ | fCP | High carb, low fat, medium protein |
| Grain Seeker | fCp | High carb, low fat, low protein |
| Protein Seeker | fcP | Low carb, low fat, high protein |
| Hunter | FcP | Low carb, medium fat, high protein |

Figure 5:
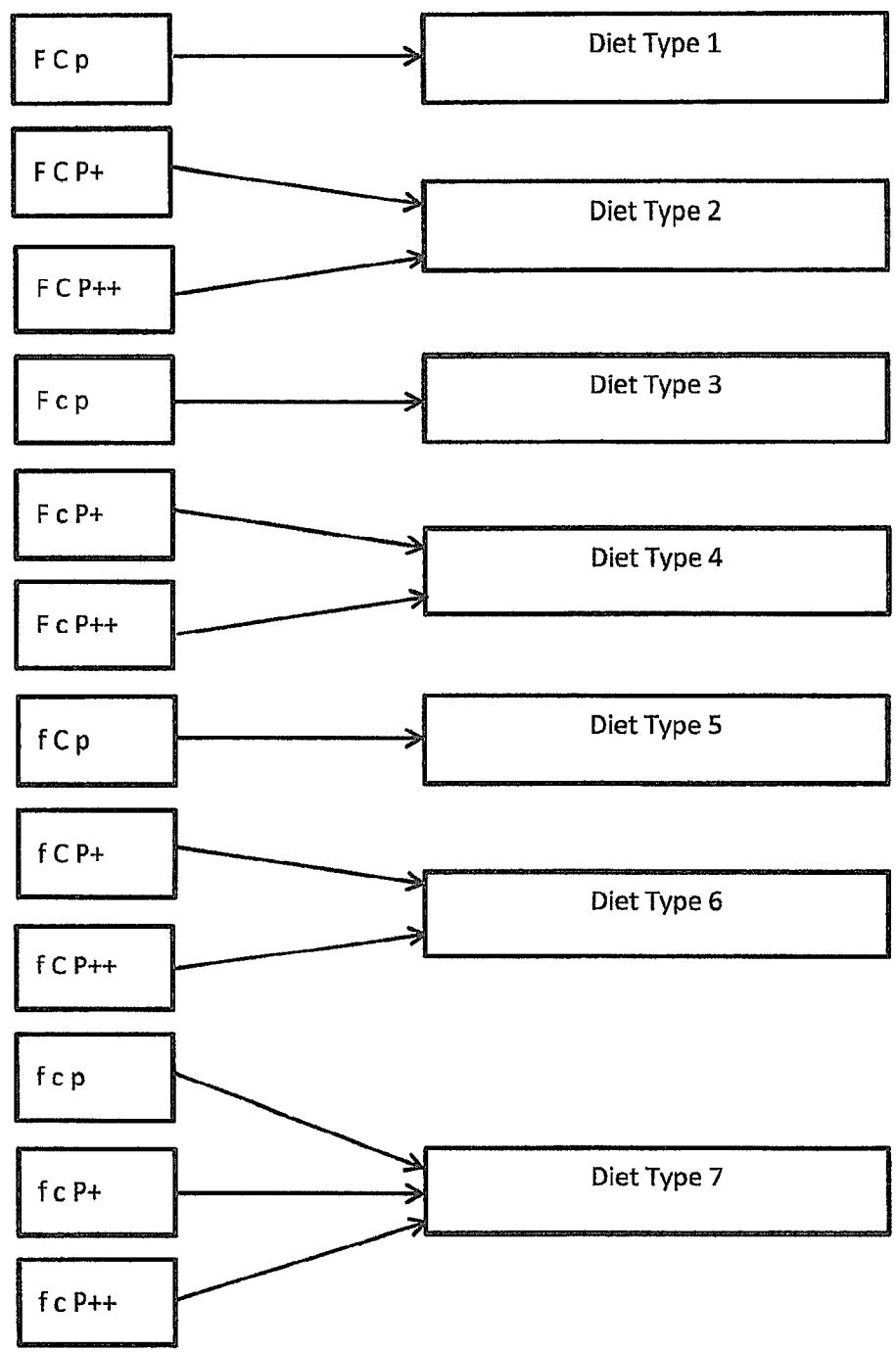
FIG. 5 depicts a mapping of combinations of macronutrient recommendations into diet types in accordance with some embodiments.
Figure 9:
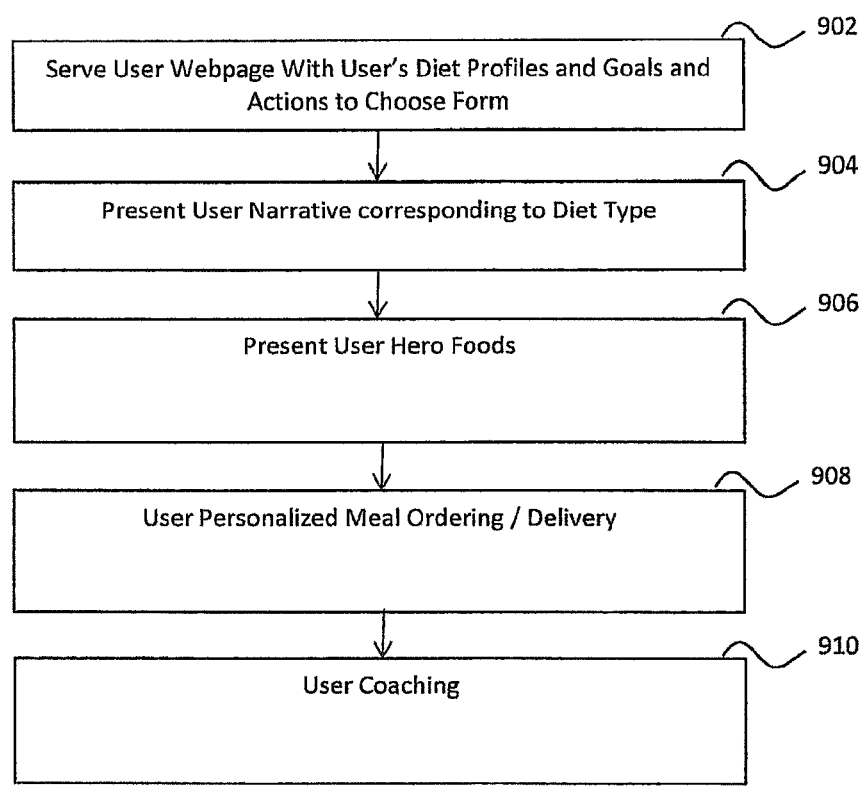
FIG. 9 depicts a method of interacting with a user over a network connection related to delivering meal, recipe, food and supplement related information based on the user's vitals, genotype and phenotype and other information provided by the user in accordance with some embodiments.

FIG. 5 shows another mapping of diet types based on macronutrient recommendations according to some embodiments. Here, there are twelve potential combinations of macro nutrient recommendations: Fats (f and F), Carbohydrates (c and C), and Proteins (p, P+ and P++). The diet types each reflect different levels of macronutrients that are personalized for the user based on vitals, genotype and phenotype data. FIG. 6 shows a table 600 that provides illustrative ranges for the seven diet types, or diet type vectors, shown in FIG. 5, according to some embodiments. Referring to the table 600, each diet type is shown with a recommended daily calorie intake of 2000 calories. The number of calories may be customized for each person based on sex, age, activity level and other factors or may be considered on a meal by meal basis. The table also includes recommended percentage ranges for each diet type or diet type vector that correspond in some embodiments to macronutrient recommendations. The macronutrient recommendations are shown as elements 605. Table elements 610 show illustrative values for calories associated with carbohydrates, fat and protein for each diet type for an exemplary meal falling within the ranges of the diet type. For each diet type, recommended meals falls within the macronutrient ranges 605 for each user. Table elements 615 show illustrative values in grams of carbohydrates, fat and protein for each diet type for an exemplary meal falling within the ranges of the diet type.

There may be different biological diet types for different groups of users or all of the diet types may be the same across the user population of a particular system 100. The diet types may range in number, but in some embodiments there are between six and nine biological diet types. There may be more or fewer depending on the design of the system or the overall vitals, phenotypical and genotypical variation found within the entire user community or groups of users defined by geography, organizations, families or other factors if desired.

After the diet types are determined for each user, the diet type information may be transmitted to the user in 214. The diet types in some embodiments may contain informative labels for the user to comprehend the type of diet that is recommended for the user. For example, diet type labels may include "balanced harvester, grain seeker, protein seeker, hunter, and other terms that are associated with macronutrient attributes of the diet type. In 216, the system may optionally transmit narratives describing ranges and the types of foods, snacks and meals that the user should eat. The narratives may include additional information about goals, micronutrient intake, supplements and other information related to the user's nutritional needs.

Figure 2B:
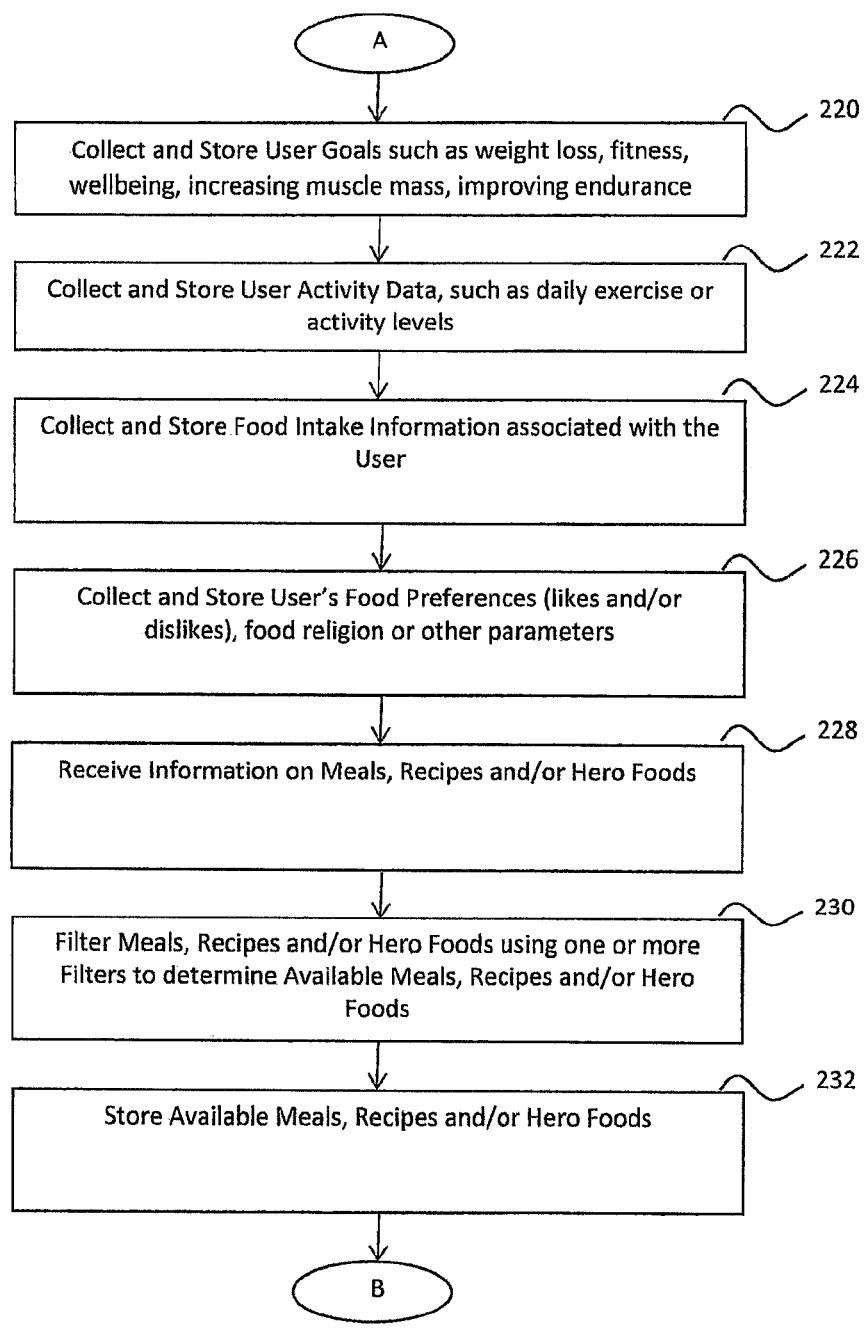
FIG. 2B is a flow chart illustrating a method of processing user diet type determined based on a user's vitals, genotypic and phenotypic data and information on available meals, recipes, foods and/or supplements to determine available meals, recipes, foods or supplements for a user in accordance with some embodiments.

FIG. 2B depicts a method of determining available meals, recipes or foods for a user based on a user's diet type and other information. In 220, the system 100 collects and stores information from the user, such as on goals, weight loss, fitness, well-being, increasing muscle mass or improving endurance. In some embodiments, the information on goals may be collected from the user by serving a webpage with a drop down menu of choices for the user to select. The goals set forth herein are illustrative only and may include any goals that have a bearing on the number of calories or types of meals, foods or supplements that a user with those goals might want to eat. The goals are stored in the database 105 associated with the system 100.

In 222, the system 100 collects and stores user activity data, such as one or more user's daily exercise or activity levels in the database 105. This data collection may be done by synchronizing a remote activity level tracker device or database associated with the user with the database 105 to transfer data to the database 105 on a user's activity levels. Alternatively, a user may upload a general description of the user's regular activity, daily activity, weekly activities, monthly activities or one time activities. The user may be prompted to enter this data or may be given a web page with drop down menus to use to describe regular or one time activities. The system may determine recommended meals or foods for users in some embodiments based on activity levels in a particular day. Alternatively, the activity levels may be used to determine calories burned by the user over periods of time and then used in meal recommendations to the user.

In 224, the system 100 collects and stores food intake information associated with the user in some embodiments. The food intake information may include: (i) information the user identifies to the system, for example in some embodiments, in response to a web page that the system provides to the user asking for food intake information; or (ii) information on meals or recipes that the user has purchased and consumed through the system. In either case, the user may identify for the system foods and supplements that the user has eaten or plans to eat in order to get meal or recipe recommendations for breakfast, lunch or dinner in a given day; to get snack, supplement or other food recommendations over the course of several days or a week based on what the user is expected to eat during that time period. The food intake information for one or more users may be stored in the database 105.

In 226, the system 100 collects and stores food preference information for each user. The food preference information may include in some embodiments: (i) a list of foods that the user is allergic to; (ii) a list of foods that the user does not like to eat; or (iii) a list of foods that the user likes to eat; (iv) the user's food religion (kosher, vegan, pescatarian and similar). Food preferences for one or more user are stored in the database 105. The food preferences may be provided by each user in response to a web pages soliciting this information with selectable choices. This information may also be uploaded by a user or a health or other service provider to the database 105.

In 228, the system receives information on meals, recipes and/or hero foods that are available for recommendation to the user and stores the information in the meals and recipe database 106. This information may be provided in some embodiments by administrators of the system 100 to the database meals and recipe database 106. Alternatively, meals, recipe and other food and supplement information may be provided by health service providers 102, meal or recipe providers 103 or users 101. The information such as recipes or available foods or meals in the database 106 may be designated to be specific to a user or specific to a group of users, for example a family, those users in a geographic area, or those users who work at a particular organization. Alternatively, some meals, foods, recipes or supplements may be designated in the database 106 to be available to all users or many groups of users.

In general, the meals and recipe information for each meal or recipe includes information on the calories of the meal or recipe and macronutrient information, such as calories from fat, carbs and protein or grams of fat, carbs and protein. The information may also include information of the type shown in FIG. 7 for each meal or recipe. The meal and recipe information may also include information on micronutrients, such as the volume, weight, or RDA percentage of one or more micronutrients. The meal processing engine 107 may provide macronutrient and micronutrient information based on the contents of the meal, recipe, food or supplement and known averages for the types of food in the recipe or meal or the types of nutrients in the food or supplements being described. Alternatively, the macronutrient and micronutrient information for the meal, recipe, food or supplement may be input by a meal or recipe provider or an administrator of the system. Meals or foods may also be stored with a breakfast, lunch, dinner, snack, hero food, supplement or other similar designation to facilitate specific recommendations to the user. Meals or recipes may be designated in more than one category in some embodiments.

In 230, meals, recipes, foods and/or supplements in the database 106 that are associated with the user may be filtered in order to determine available meals, recipes, foods or supplements for the user. One or more filters may be selected an applied for each user. For example, in some embodiments the available meals and recipes are filtered based on the user's biological diet type 116. This filtering is based on, for example, macronutrient recommendations and meals that do not fit within macronutrient ranges are filtered out.

In some embodiments, in 117 a user's food preferences are used to filter the available meals, recipes, foods or supplements. When a user's food preferences indicate that the user cannot eat fish, for example, then meals or recipes with fish will be filtered out. Similarly, other meals with one or more ingredients that are not allowed or desired for a user are filtered out in some embodiments.

In some embodiments, a user may provide other criteria in 118 that is used to filter meals. For example, a user might have a goal of not exceeding 500 calories at dinner. This criteria may be used to filter available dinners that have fewer than 500 calories. Similarly, a user may specify a criteria that the user is searching for one or more dinner meals or recipe. This criteria may be used to filter out breakfast or lunch recipes.

After any user (or user group) specific filtering 115 is applied to the available meals, recipes, foods and/or supplements, the available meals, recipes, foods and/or supplements 120 are generated and stored in connection with the user. These are available meals, recipes, food and/or supplements for a user based on each user's preferences, biological diet type and other criteria in some embodiments.

Figure 2C:
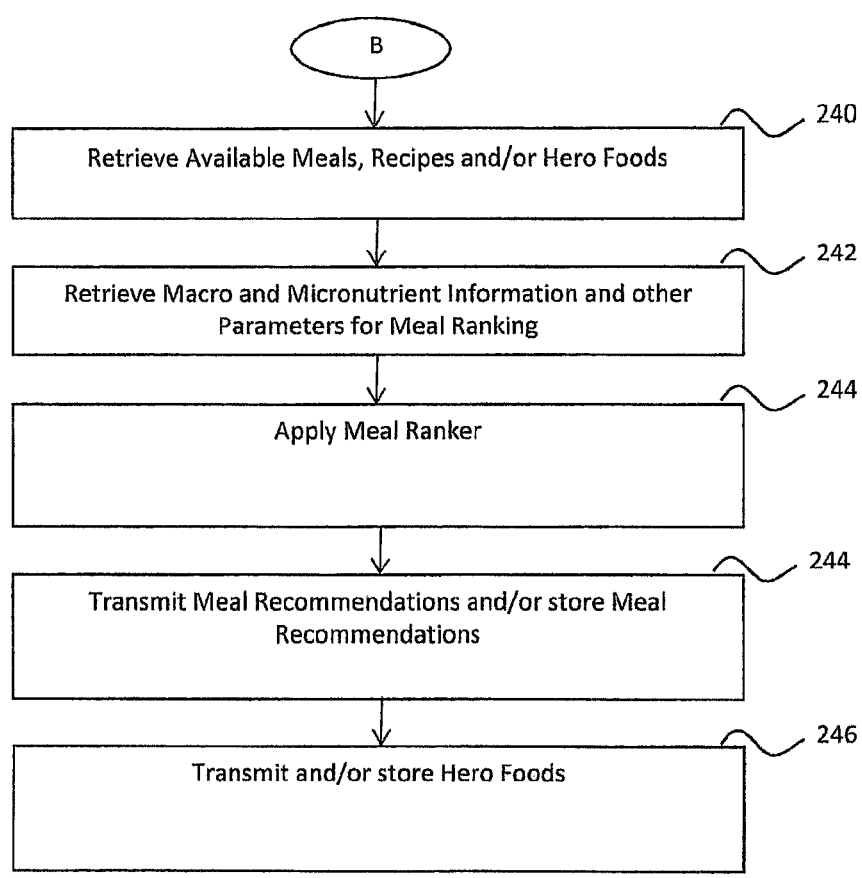
FIG. 2C is a flow chart illustrating a method of ranking available meals, recipes, foods and/or supplements for a user based on a user's diet type and vitals, genotypic and phenotypic data in accordance with some embodiments.

FIG. 2C depicts a method of generating meal, recipe, food or supplement recommendations for a user according to some embodiments. The method of 2C may be applied to selecting meals or recipes. Similarly, the method of 2C may be applied to selecting snacks, such as hero foods or other snacks with an ingredient list or supplements. Available meals, recipes, foods or supplements stored in 232 may be retrieved in 240 in connection with a particular user in order to make one or more recommendations to the user. In 242, the system 100 retrieves macronutrient and micronutrient recommendations for the user, diet type information associated with the user, and other meal ranking parameters. One or more of the following meal ranking parameters may be used in some embodiments:

Meal type—breakfast, lunch, dinner or snack;
User activity level;
User goals;
User food intake;
User group or organization;
Cost of meals or recipes;
Availability of ingredients for meals or recipes;
Micronutrients;
Macronutrients;
Calories;
Available meals associated with other users and the ability to share ingredients among a user group for which meals are being prepared;
Past user meal selections; and
Meal variety in view of past meal selections;

The meal ranking parameters in some instances are specific to users, user groups or geographies where users are located. In other instances, the meal ranking parameters may be specific to the meal preparer, or to the specific meals or recipes or ingredients.

In 244 a meal ranker algorithm is applied. In some embodiments, the meal ranker algorithm ranks meals based on the user's micronutrient recommendations and the ability of the meal to provide those micronutrients. This is performed in some embodiments by applying for at least some micronutrients recommend for the user, the following equation:

$$((\text{Micronutrient amount in the meal} - \text{Micronutrient recommendation for the user})/(\text{Micronutrient recommendation for the user} + \text{Micronutrient amount in the meal}))^2$$

Each micronutrient subject to the calculation is then summed together for each meal. The highest ranked meal has the lowest micronutrient score. The meals are ranked from first to last based on the lowest to highest micronutrient score. The top X meals or recipes are then transmitted or recommended to the user in 244. The value of X may be any number that is designed to give the user some choices without flooding the user with too many choices. When snacks supplements or hero foods are being ranked or recommended, those may be transmitted in 246 to the user. The foods, such as prepared meals, recipes, hero foods or supplements, are ranked and/or recommended for the user and may also be stored for the user. FIG. 8 depicts a list of micronutrients (or basic foods) that may be given values specific to a user and used to score each meal, recipe or snack in the meal ranker algorithm and that also may be given values in each meal, recipe, snack or supplement in the database 106.

The user may be given a web page to specify what recommendations the user is looking for in order to drive the method of FIG. 2C. For example, the user may be seeking a dinner recipe or to order meals for the next week. The user may specify that the user wants the top 10 recommended meals and/or recipes in some embodiments. The user may specify that the user wants only dinner recipes or breakfast, lunch and/or dinner meals and recipes to choose from. Similarly the user may specify snacks or supplements. The meal ranker algorithm will select from the available meals, recipes, foods and supplements and make recommendations according to the methods described herein after ranking.

Other techniques for ranking factor in cost, calories, and goals. Still other techniques may take into account meals (and ingredients) being made available to other users based on their respective diet types so that there are economies of scale for the food preparation process when there are a plurality of users for which meals are being prepared. Still other techniques may store selections of the user in response to past meal recommendations. This may be used to determine both what the user likes because of the user choices as well as what the user does not like because the user does not selected certain recommended meals. In some embodiments, different hueristic equations may be used to optimize selections for users. In some embodiments, the other ranking parameters may be given a score between 0 and 1 (or more than that) and then added to the micronutrient summation. Meal ranking is then performed for each meal based on its overall score with the low score representing a higher rank. There are many ways to rank meals, recipes, foods and/or supplements based on macronutrient and micronutrient content and macronutrient and micronutrient recommendations for the user and other meal ranking parameters and it will be understood by those having ordinary skill in the system may prioritize and score meals in a variety of ways all of which are within the scope of the invention.

Decision Tree Engine

Figure 10:
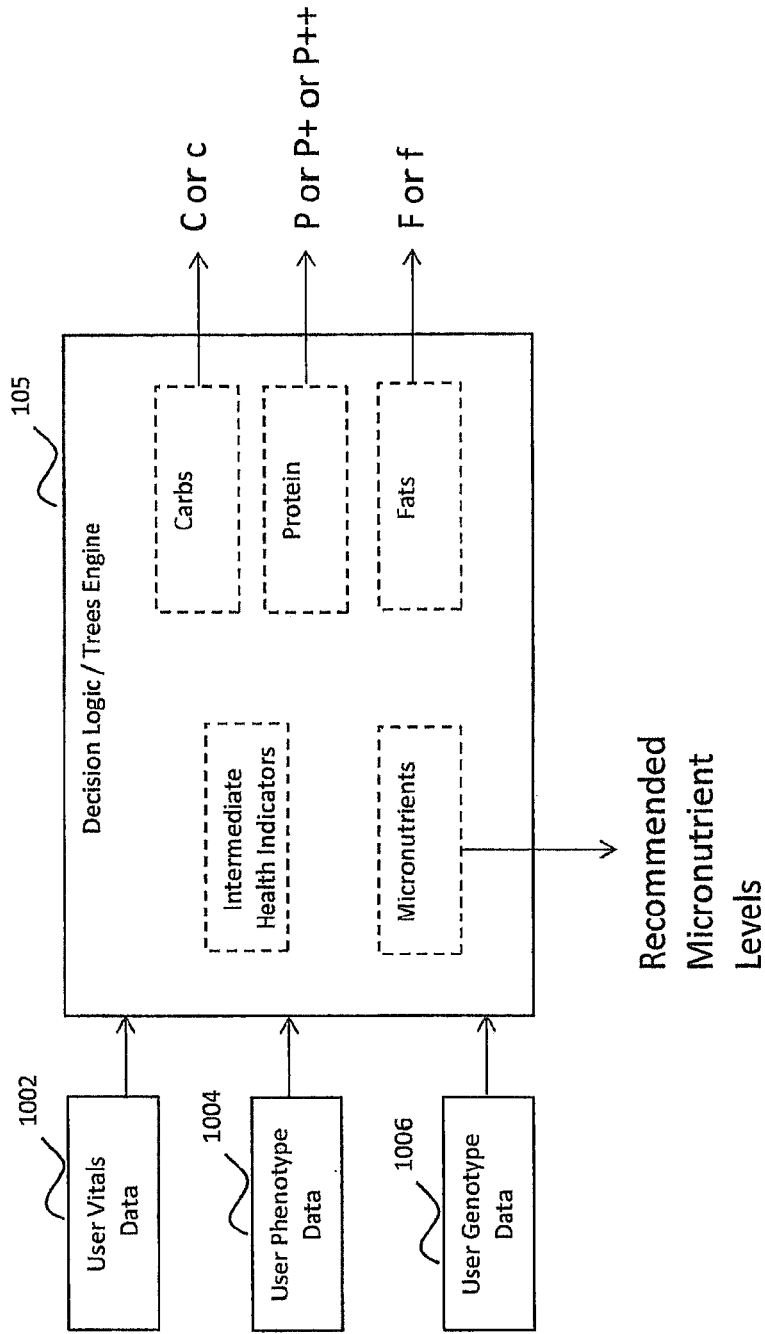
FIG. 10 depicts an illustrative classifier that produces macronutrient and micronutrient recommendations based on vitals, genotypic and/or phenotypic data for a user in accordance with some embodiments.

According to some embodiments of the invention, a user's diet type and recommended meals and foods are based on an individualized determination of each user's macronutrient and micronutrient needs. Referring to FIG. 10, these needs are determined by receiving vitals 1002, phenotype 1004 and genotype 1006 data from each user.

Vital Information

In general, the vitals data may include data such as shown below:

| | |
|---|---|
| UserId | # or alphanumeric |
| Height | # |
| Weight | # |
| Sex | M/F |
| Waist Circumference | High/Low or High/Med/Low or >33/<33 |
| Blood Pressure | High/Low or #/# |
| Activity Level | High/Med/Low or Calories/day or other measure |

In some embodiments, body mass index (BMI) can also be used.

Phenotypic Information

In addition to the vitals information, the system also utilizes measurements of phenotypic and genotypic biomarkers to assess a number of physiological factors such as metabolic health and endurance, insulin response, etc., as is more fully described below. The phenotype and genotype data in some embodiments is as shown in FIGS. 3 and 4 respectively.

The phenotype data generally includes information obtained from blood testing on the user. In some embodiments, the user's blood is sampled after fasting and at future times after ingestion of a challenge beverage as described in more detail below. The challenge beverage is designed to provide carbohydrates, fats and proteins to the user and then measure the user's response at intervals. The blood samples provide some insight into the user's ability to process sugars, fats and proteins based on the changes in biomarkers present in the blood over time. The blood samples also may include information about cholesterol, vitamin and/or mineral levels, triglicerides, hormone levels and other information.

Accordingly, the user takes a blood sample at a fasting state, drinks the challenge beverage and then takes blood samples at a number of different time points, usually from one to three time intervals, with a fasting level, a measure at 30 minutes and another at two hours finding use in many situations, although other time periods can be done, including, but not limited to, thirty minutes, one hour, two hours and three hours. The blood levels of one or more of the following phenotypic biomarkers are then assayed and input into the system, with from one, 5, 10, 15, 20, 25 or all 28 being tested in some embodiments.

In one embodiment, glucose levels are measured as a marker of metabolic health and insulin sensitivity as it relates to metabolic health. Accordingly, glucose can be measured at t=0 (fasting), t=30 minutes (glucose_t30) and t=120 minutes (glucose_t120).

In one embodiment, C-peptide biomarkers are used as a measure of metabolic health and insulin sensitivity as it relates to metabolic health. The connecting peptide, or C-peptide, is a short 31-amino-acid polypeptide that connects insulin's A-chain to its B-chain in the proinsulin molecule and is a marker for how much insulin a user is making. Accordingly, the C-peptide levels can be measured at t=0, t=30 minutes (C-peptide_t30) and t=120 minutes (C-peptide_t120).

In one embodiment, the blood level of carotenoids in the plasma are tested for all time points as an indication of carotenoid intake. In one embodiment, a disposition index is measured as this is an indicator of beta cell function and thus can be used to assess metabolic health and insulin sensitivity. In one embodiment, a hepatic insulin index is done on each time point, which measures hepatic glucose production (HGP) and calculates indices of hepatic insulin resistance as an indicator of metabolic health, insulin sensitivity.

In one embodiment, several different cholesterol levels are determined at all time points, including HDL, LDL, total cholesterol and using a ratio of total cholesterol:HDL cholesterol.

In one embodiment, total cholesterol is measured at all time points. In one embodiment, HDL cholesterol levels are measured at all time points, which is an indicator of heart health. In one embodiment, LDL cholesterol levels are measured at all time points as well.

In one embodiment, high sensitivity C-reactive protein is measured at all time points as a biomarker for inflammation. The cut points of low risk (<1.0 mg/L), average risk (1.0 to 3.0 mg/L), and high risk (>3.0 mg/L) may be used.

In one embodiment, a magnesium category test is measured at all time points which is a marker for blood pressure, inflammation and insulin sensitivity.

In one embodiment, an Omega-3 index is done at all time points, which can be used for recommendations regarding the intake of omega 3 for heart health.

In one embodiment, a potassium category test is done at all time points, which is relevant to blood pressure and heart health.

In one embodiment, the ratio of two essential amino acids ARA/AA and EPA is measured at all time points. The AA/EPA ratio is an indication of levels of cellular inflammation, with a ratio of 1.5 to 3 indicating low inflammation, 3 to 6 indicating moderate inflammation, 7 to 15 is elevated inflammation and >15 indicating high inflammation.

In one embodiment, sodium levels are measured at all time points as an indicator of blood pressure and heart health and for intake recommendations.

In one embodiment, the blood level of triglycerides are measured at a fasting state (t=0), and then at 30 minutes and 120 minutes, as an indication of heart health, blood lipids, metabolic health and metabolic syndrome.

In one embodiment, vitamin A levels are measured at all time points for intake recommendations.

In one embodiment, vitamin B6 levels are measured at all time points as an indicator of blood pressure and heart health and for intake recommendations.

In one embodiment, vitamin C levels are measured at all time points as an indicator of blood pressure and for intake recommendations.

In one embodiment, vitamin D levels are measured at all time points for intake recommendations.

In one embodiment, vitamin B6 levels are measured at all time points for intake recommendations.

In one embodiment, zinc levels are measured at all time points for intake recommendations.

Genotypic Data

In general, the genotype data is taken from DNA analysis on the user. Certain single nucleotide polymorphisms (SNPs) or genetic markers may be selected based on their correlation with health and dietary intake and are depicted in FIG. 4. In general, one or more of the following 34 genotypic biomarkers are tested, with from at least about 5, 10, 15 20, 25, 30 or all 34 finding use in many embodiments.

As will be appreciated by those in the art, any number of standard SNP detection techniques can be used, including, but not limited to, hybridization methods, enzyme based methods and nucleic acid sequencing methods. Hybridization methods include, but are not limited to, dynamic allele-specific hybridization (DASH) genotyping which takes advantage of the differences in the melting temperature in DNA that results from the instability of mismatched base pairs; this is frequently done as in known in the art using molecular beacon technologies or SNP microarray technologies. Enzymatic methods include enzyme based amplification technologies, where the amplification only occurs and/or doesn't occur based on the presence or absence of the SNP, such as polymerase chain reaction (PCR), oligonucleotide ligation assays (OLA), primer extension methods, etc. Nucleic acid sequencing methods utilize a number of different technologies, including single molecule sequencing (Pacific Biosciences), sequencing by synthesis (Illumina), pyrosequencing (454), ion semiconductor (Ion Torrent), and sequencing by ligation (SOLiD).

In some embodiments, the user's blood is tested for the presence of the angiotensin I-converting enzyme insertion/deletion (ACE VD) polymorphism ACE rs1799752, the presence of which is associated with human physical performance including endurance, see Ma et al., PLOS, The Association of Sport Performance with ACE and ACTN3 Genetic Polymorphisms: A Systematic Review and Meta-Analysis. PLoS ONE 8(1): e54685, hereby incorporated by reference in its entirety.

In some embodiments, the user's blood is tested for the presence of the angiotensin I-converting enzyme insertion/deletion (ACE VD) polymorphism ACE rs4646994, the presence of which is associated with blood pressure and sodium recommendations. The most influential dietary factor for the renin-angiotensin system (RAS) is sodium. Interactions between the ACE VD polymorphism, sodium intake and the RAS system determine blood pressure and therefore influence risk for hypertension.

In some embodiments, the user's blood is tested for the presence of the ADAMT69 risk allele rs4607103, the presence of which is associated with insulin sensitivity, insulin secretion and fiber recommendations.

In some embodiments, the user's blood is tested for the presence of the ADRB3 rs4994, the presence of which is associated with human physical performance including endurance, In some embodiments, the user's blood is tested for the presence of the AGT rs5051 SNP, the presence of which is associated with blood pressure and sodium recommendations.

In some embodiments, the user's blood is tested for the presence of the AGT rs699 SNP, the presence of which is associated with blood pressure and sodium recommendations.

In some embodiments, the user's blood is tested for the presence of the APOA5-A4-C3-A1 rs964184, the presence of which is associated with macro fat recommendations, diet type, blood pressure, insulin sensitivity (specifically fat consumption).

Cholesteryl ester transfer protein (CETP) is an important regulator of plasma HDL-C. Several genetic mutations in the CETP gene were found to be associated with HDL-C levels. Accordingly, in some embodiments, the user's blood is tested for the CETP rs1532624 allele, the presence of which is an indicator of heart health based on LDL and a total cholesterol diagnosis.

In some embodiments, the user's blood is tested for the CETP rs1532624 allele, the presence of which is an indicator or useful for classifying the carbohydrate diet types and insulin sensitivity low carb tree.

In some embodiments, the user's blood is tested for CYP1A2 rs762551, with the rs762551(A) allele being associated as a "fast metabolizer" and the (C) allele is by comparison a slower metabolizer of certain substrates (including caffeine).

The FADS1 gene codes for the fatty acid delta-5 desaturase, a key enzyme in the metabolism of long-chain polyunsaturated omega-3 and omega-6 fatty acids. In some embodiments, the user's blood is tested for one or both of FADS1 rs174546 or rs174548, as variants in the fatty acid desaturase 1 (FADS1) gene are also associated with altered polyunsaturated fatty acids (PUFAs) such as omega-3, and the presence of these SNPs is used as an indicator of heart health, blood pressure for the epa dha recommendation (omega 3), for intake omega-3.

The FTO gene encodes the fat mass and obesity-associated protein (also known as alpha-ketoglutarate-dependent dioxygenase FTO). In some embodiments, the user's blood is tested for the FTO rs11221980 SNP, the presence of which is used for diet type classification (carbs and fats), and as a marker for insulin sensitivity for fat consumption, insulin sensitivity for low carbohydrates, and weight maintenance for energy balance.

In some embodiments, the user's blood is tested for the FTO rs9939609 SNP, the presence of which is used for diet type classification (carbohydrates, proteins and fats), and as a marker for blood pressure relating to fat.

In some embodiments, SNPs associated with group-specific component (vitamin D binding protein) GC gene area tested as they have been linked by several studies to vitamin D serum concentrations. The allele associated with lower vitamin D, and thus the potential for vitamin D insufficiency, is rs2282679(C). Thus in some embodiments, the user's blood is tested for the GC rs2282679 SNP, the presence of which is related to the recommendation for vitamin D levels as well as for inflammation.

In some embodiments, the user's blood is tested for the presence of the GC rs4588 SNP, the presence of which is related to the recommendation for vitamin D levels as well as for inflammation.

In some embodiments, the user's blood is tested for the presence of the GC rs7041 SNP, the presence of which is related to the recommendation for vitamin D levels as well as for inflammation.

The T-allele of GCKR (glucokinase regulatory protein (GCKR) gene) SNP rs780094 is associated with increased triglycerides. Accordingly, in some embodiments, the user's blood is tested for the presence of the GCJR rs7800094 SNP, the presence of which is related to insulin sensitivity for fasting glucose levels.

HLA-DQ is a gene family for a αβ heterodimer cell surface receptor. In some embodiments, a user's blood is tested for an HLA-DQ SNP, as a number of these are related to celiac disease and gluten sensitivity. In some embodiments, the SNP is the HLA-DQ2.2 rs2395182 SNP. In some embodiments, the SNP is the HLA-DQ2.2 rs4713586 SNP. In some embodiments, the SNP is the HLA-DQ2.2 rs7775228 SNP. In some embodiments, the SNP is the HLA-DQ2.5 rs2187668. In some embodiments, the SNP is the HLA-DQ7 rs4639334 SNP.

The rs4402960 SNP in the insulin like growth factor 2 mRNA binding protein (IGF2BP2 rs4402960) are associated with type-2 diabetes risk and is thus used as a biomarker for the fat diet type and insulin sensitivity for fat consumption. In some embodiments, the user's blood is tested for the presence of the IGF2BP2 rs4402960 SNP.

The IL6 rs1800795 SNP is a SNP in the promoter of the IL-6 gene that is associated with inflammation. In some embodiments, the user's blood is tested for the presence of the IL6 rs1800795 SNP.

The MCM6 gene encodes the protein DNA replication licensing factor MCM6, one of the highly conserved minichromosome maintenance complex proteins that are essential for the initiation of eukaryotic genome replication. The MCM6 rs4988235 SNP is associated with lactose intolerance and lactose sensitivity. In some embodiments, the user's blood is tested for the presence of the MCM6 rs4988235 SNP.

The MTHFR gene encodes the vitamin-dependent enzyme, methylenetetrahydrofolate reductase, involved in folate metabolism and thus associated with blood pressure in terms of riboflavin. The MTHFR rs1801133 SNP Homozygous rs1801133(T; T) individuals have ~30% of the expected MTHFR enzyme activity, and rs1801133(C; T) heterozygotes have ~65% activity, compared to the most common genotype, rs1801133(C; C). In some embodiments, the user's blood is tested for the presence of the MTHFR rs1801133 SNP.

The nitrous oxide synthase gene NOS3 gene variant rs1799983 is strongly associated with coronary artery disease; a large study found that homozygosity for rs1799983 (T; T) increases risk of ischemic heart disease and can be used as a biomarker for blood pressure for cocoa flavanols and resveratrol recommendations. In some embodiments, the user's blood is tested for the presence of the NOS3 gene variant rs1799983.

The PPARG rs1801282 associates with type 2 diabetes and interact with physical activity, as diet type (fats), insulin sensitivity for fat consumption In some embodiments, the user's blood is tested for the presence of PPARG rs1801282 (Pro12A1a).

In some embodiments, the user's blood is tested for the presence of the R577X rs1815739 SNP. This SNP, in the ACTN3 gene, encodes a premature stop codon in a muscle protein called alpha-actinin-3. The polymorphism alters position 577 of the alpha-actinin-3 protein. In publications the (C; C) genotype is often called RR, whereas the (T; T) genotype is often called XX. The (T; T) is under-represented in elite strength athletes, consistent with previous reports indicating that alpha-actinin-3 deficiency appears to impair muscle performance and is accordingly a marker for muscle performance.

In some embodiments, the user's blood is tested for the presence of the TCF7L2 (Transcription Factor 7 Like 2) rs7903146 SNP as this is one of two SNPs within the TCF7L2 gene that have been reported to be associated with type-2 diabetes, It is used as a biomarker for diet types relating to carbohydrates and fats, blood pressure for fat, insulin sensitivity for low carbohydrates, and weight maintenance for energy balance.

The TNF rs1800629 SNP in the tumor necrosis factor-alpha gene, rs1800629, is also known as the TNF-308 SNP. Occasionally the rs1800629(A) allele is referred to as 308.2 or TNF2, with the more common (G) allele being 308.1 or TNF1. The (A) allele is associated with higher levels of TNF expression. This SNP has been linked to a wide variety of conditions including inflammation. Accordingly, in some embodiments, the user's blood is tested for this SNP.

In some embodiments, the user's blood is tested for the presence of the VDR rs1544410, also known as the BsmI polymorphism, is a SNP in the Vitamin D receptor (VDR) and is used as a marker for Vitamin D.

Figure 12B:
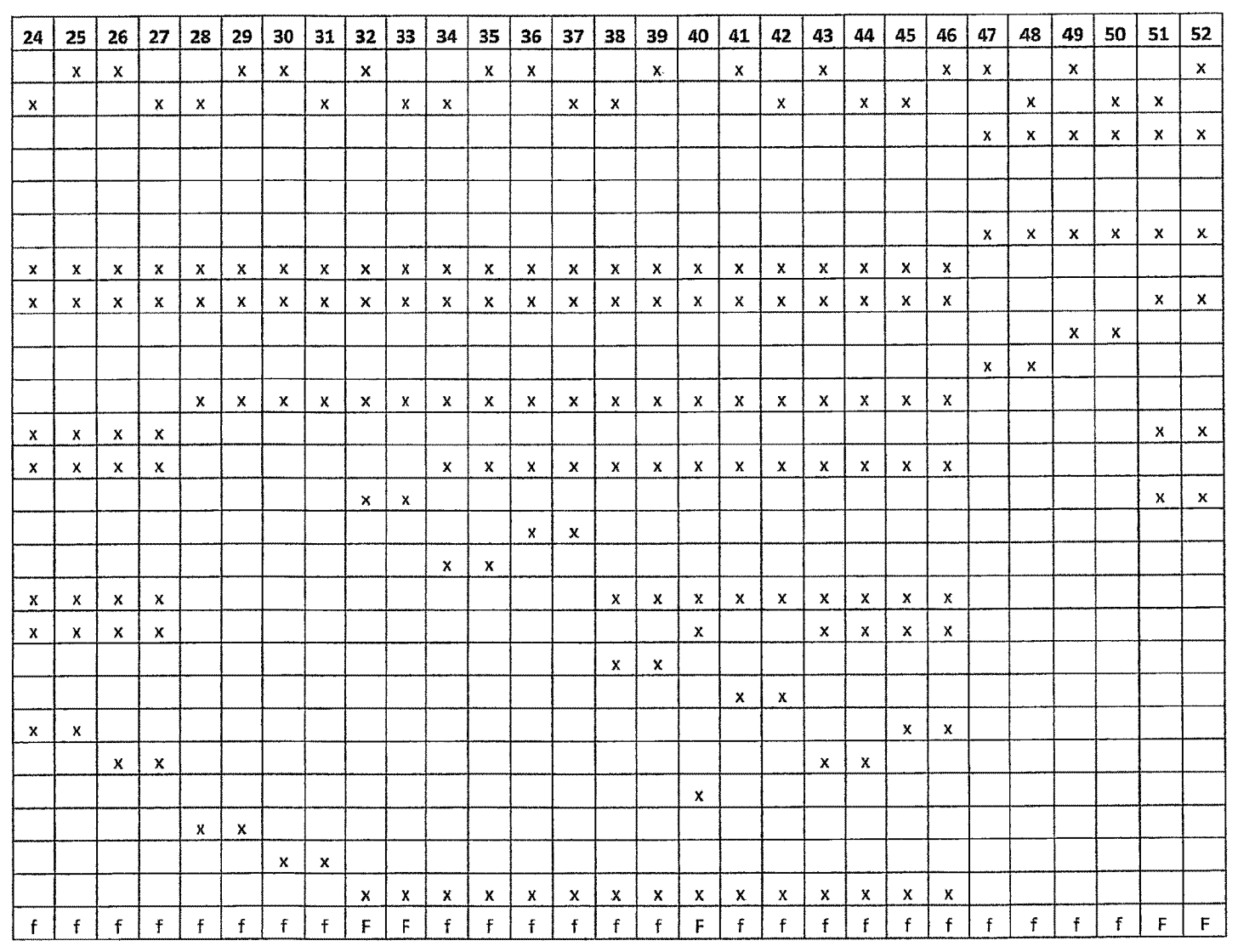
Figure 12C:
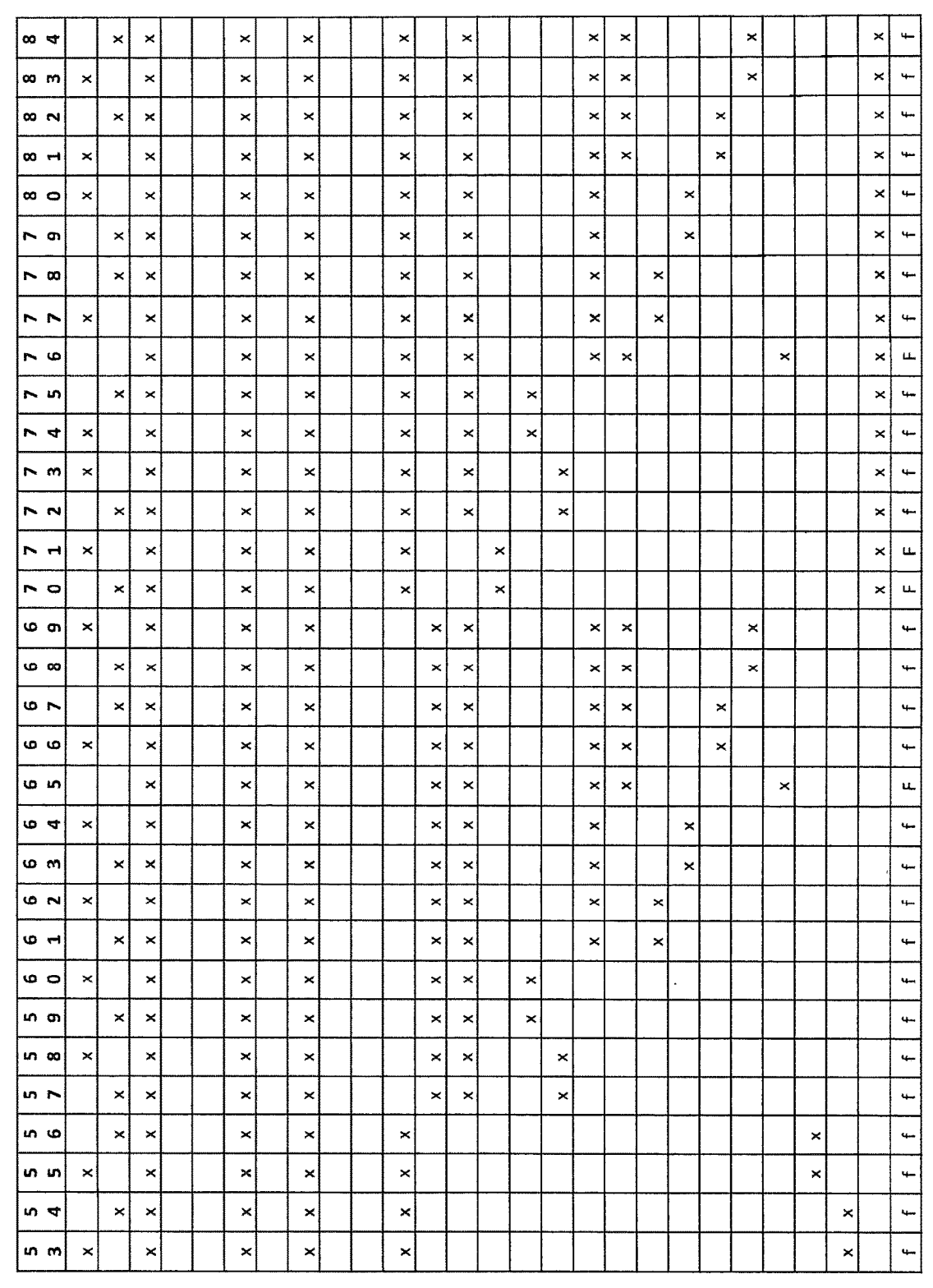

The decision tree Engine 108 receive the vitals, genotype and phenotype data for each user and convert this data into macronutrient and micronutrient recommendations. The recommendations are essentially vectors that correlate relevant macronutrients or micronutrients with a level or range for each user. In the case of macronutrients, the user's vector includes values as shown for Carbohydrates, Fats and Protein. An illustrative decision tree for carbohydrates is shown in FIGS. 11A and B. An illustrative decision tree for Fats is shown in FIG. 12. An illustrative decision tree for Protein is shown in FIG. 13. In general, the decision trees receive the inputs of vitals, genotype and genotype data, and through the application of rules and logic, the decision trees produce the user's macronutrient recommendation vector. The range of values produced and included in the user's macronutrient recommendation vector may be as shown in FIGS. 5 and 10. Alternatively, values, value ranges thresholds may be applied. As shown in FIG. 5, the macronutrient recommendations may be mapped into diet types. Alternatively, the decision tree or decision logic may directly output diet types from input values. The macronutrient recommendations and diet types for each user in some embodiments are based on vitals, phenotype and genotype data for each user.

The micronutrient recommendations for each user are similarly based on the vitals, phenotype and genotype data for each user. However, certain micronutrient recommendations may be based on less than all three data types. A list of micronutrients and/or foods, levels for all or some of which may be determined for each user are shown in FIG. 8. Meals, recipes, foods, snacks and supplements that are stored in the database 106 also may include information on levels of micronutrients such as those in the list of FIG. 8. Both for the macronutrient recommendations and the micronutrient recommendations, the decision logic may include determining intermediate values that are used in determining multiple macronutrient or micronutrient recommendations. Some examples of intermediate values include The decision tree engine may implemented in program instructions that implement decision tree logic that are stored in memory of a computer and then are executed by a processor within the computer to process the inputs and produce macronutrient, micronutrient and diet types based on the vitals, genotypical and phenotypical data for each user. The decision trees may be static. Alternatively, the decision tree logic may be updated over time. The relevant vitals, phenotypical or genotypical data for each user that is used in the recommendations may also change over time in some embodiments. The changes in decision tree logic may be driven by new scientific information about food and the impact of genotype or phenotype on health in some embodiments. In some embodiments, the decision tree logic be updated based on feedback from results of users of the system as the vitals and phenotypical data of users change over time based on their meals. activity levels and aging.

In general, each of the methods and processes shown and described herein may be implemented on a server or other computer and the web server interface, decision tree engine, filtering engine and meal ranker engine may implemented by a server or other network connected computer. These computers may one computer or may be centralized or distributed and may share data with each other and other network elements shown in FIG. 1 via the Internet, local area networks, wide area networks or other networks. The processes in some embodiments are implements as program instructions that may be stored as software or firmware in the memory of a device or other computer and executed by a processor. In general, for each of the devices, servers and engines shown herein, the device includes a memory, a processor, input/output units, and networking units. The processor executes program instructions to perform the processes shown and described herein, including database queries, web interfaces, meals processing, health decision trees, filtering, meal ranking and other user interactions to ensure user registration, meal and food recommendations and in other instances payment and arranging for delivery of meals or other food.

The databases include stored data regarding users, which may be stored in an encrypted and secure manner. Additional information that is collected or generated during the processes shown and described herein may be stored in the databases. In general, the databased are network connected and may store or provide information in response to queries to any of the network elements in order to facilitate the processes shown and described herein.

Figure 15:
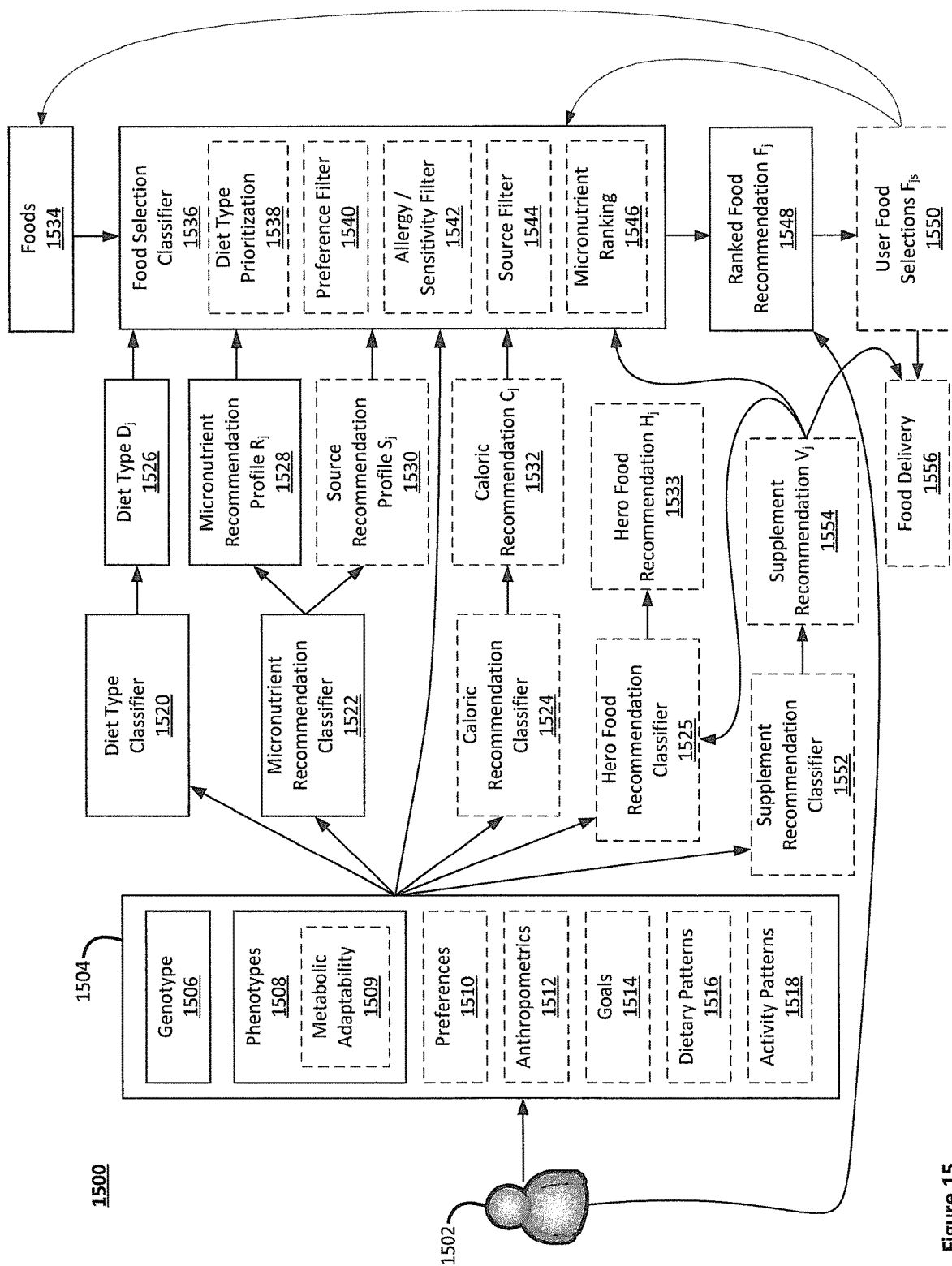
FIG. 15 is a block diagram illustrating an implementation of a personalized food and nutrition recommendation method, in accordance with some embodiments.

FIG. 15 illustrates methods and systems for personalized food and nutrition recommendation system 1500, in accordance with some embodiments. Information about the user 1502 is collected, e.g., one or more of genotypic information 1506, phenotypic information 1508 which, in some embodiments includes metabolic adaptability information determined, for example, through analysis of the user's blood following consumption of a multi-nutrient challenge beverage as described herein, food preferences 1510 (e.g., food likes, dislikes, food religions, or other dietary preferences), anthropometrics 1512 (e.g., physical measurements of the individual), goals 1514 (e.g., weight loss, muscle building, or increases in energy), dietary patters 1516 (e.g., eating habits or food logs), and activity patterns 1518 (e.g., typical physical activities, exercise logs, or measured caloric outputs). In some embodiments, information about the user is collected multiple times, e.g., before initial classification and one or more times after adapting a particular diet. In some embodiments, information collected after implementation of a food habit is used to track changes in the user and/or adjust classification of the user based on changes accompanying the adapted food habits. For example, a user initially identified as having elevated blood pressure may be initially classified as requiring a diet low in fats. However, upon re-testing after implementing a low fat diet, it may be found that the user's blood pressure has been reduced. This information can be used to reclassify the user as no longer requiring a diet low in fats, e.g., in combination with other risk factors.

The information about the user is applied to one or more food recommendation classifiers, e.g., one or more of diet type classifier 1520, micronutrient recommendation classifier 1522, caloric recommendation classifier 1524, hero food classifier 1525, and a supplement recommendation classifier 1552, to provide one or more food classifications and/or recommendations for the user, e.g., one or more of a diet type 1526, a micronutrient recommendation profile 1528, a source recommendation profile 1530, a caloric recommendation 1532, a hero food recommendation 1533, and a supplement recommendation classifier.

In one embodiment, a method for recommending foods to a user includes obtaining genotypic data about the user comprising a plurality of first features $X=\{x_1 \ldots, x_m\}$ (e.g., one or more of the genotypes described above with respect to FIG. 1 and/or identified in FIG. 4), wherein each respective feature xi in the plurality of first features X is a status of a locus in a plurality of loci and obtaining phenotypic data about the user comprising a plurality of second features $Y=\{y_1 \ldots, y_n\}$ (e.g., one or more of the phenotypes described above with respect to FIG. 1 and/or identified in FIG. 3), wherein each respective feature $y_i$ in the plurality of second features Y is a status of a phenotype in a plurality of phenotypes.

The method then includes assigning a respective diet type $D_j$ in a plurality of diet types $D=\{D_1 \ldots, D_q\}$ (e.g., assigning one of diet types 1-7 as described above with respect to FIGS. 1 and 5) to the user by inputting a first sub-plurality $X_1$ of the plurality of first features X and a first sub-plurality $Y_1$ of the plurality of second features Y into a diet type classification model (e.g., diet type classifier 1520 in FIG. 15, health decision tree engine 108 in FIG. 1, and/or and illustrative macronutrient classification models in FIGS. 11-13).

The method also includes assigning a micronutrient recommendation profile $R_j=\{r(z_i) \ldots, r(z_s)\}$ comprising a recommendation $r(z_i)$ for each respective micronutrient $z_i$ in a plurality of micronutrients $Z=\{z_1 \ldots, z_s\}$ (e.g., one or more of the micronutrients identified in FIG. 8 and/or described above with reference to FIG. 1) to the user by inputting a second sub-plurality $X_2$ of the plurality of first features X and a second sub-plurality $Y_2$ of the plurality of second features Y into a micronutrient classification model (e.g., one or more illustrative micronutrient classification model in FIGS. 16-23).

Finally, the method includes ranking one or more foods in a plurality of foods $L=\{N_1 \ldots, N_t\}$ (e.g., foods 1534 such as meals in a master library of meals or menu of selected meals, for example, a weekly menu of meals), wherein each respective food $N_i$ in the plurality of foods has a corresponding nutrition profile $P_{Ni}=\{D_{ki}, P(z_{ki})\}$ comprising an assigned diet type $D_k$ in the plurality of diet types D and an assigned micronutrient profile $P(z_k)=\{v(z_1) \ldots, v(z_s)\}$, wherein the micronutrient profile $P(z_k)$ includes a respective value $v(z_i)$ for each micronutrient $Z_i$ in the plurality of micronutrients Z, by comparing the diet type $D_j$ and micronutrient recommendation profile $R_j$ assigned to the user to the nutrition profiles $P_N$ of foods N in the plurality of foods L (e.g., via one or more of user specific filtering engine 115 as described with respect to FIG. 1, meal ranker engine 125 as described with respect to FIG. 1, and food selection classifier 1536 described with respect to FIG. 15).

In some embodiments, assigning a respective diet type $D_j$ includes assigning macronutrient recommendations for fat, carbohydrate, and protein intake to the user and then matching the assigned macronutrient recommendations to a diet type D (e.g., one of the seven diet types described above with reference to FIG. 5).

For example, in some embodiments, the method includes assigning a macronutrient fat intake recommendation $F_j$ to the user by inputting a third sub-plurality $X_3$ of the plurality of first features X and a third sub-plurality $Y_3$ of the plurality of second features Y into a fat recommendation classification model (e.g., the fat recommendation classifier described above with reference to FIG. 12). In some embodiments, the user is assigned either a low fat dietary recommendation (f) or a regular fat dietary recommendation (F). In other embodiments, the fat macronutrient dietary recommendation is one of more than two classes of recommendations, e.g., one of three, four, five, or more classes of recommendations.

In some embodiments, the method also includes assigning a macronutrient carbohydrate intake recommendation $C_j$ to the user by inputting a fourth sub-plurality $X_4$ of the plurality of first features X and a fourth sub-plurality $Y_4$ of the plurality of second features Y into a carbohydrate recommendation classification model (e.g., the carbohydrate recommendation classifier described above with reference to FIG. 11). In some embodiments, the user is assigned either a low carbohydrate dietary recommendation (c) or a regular fat dietary recommendation (C). In other embodiments, the carbohydrate macronutrient dietary recommendation is one of more than two classes of recommendations, e.g., one of three, four, five, or more classes of recommendations.

In some embodiments, the method also includes assigning a macronutrient protein intake recommendation $P_j$ to the user by inputting a fifth sub-plurality $X_5$ of the plurality of first features X and a fifth sub-plurality $Y_5$ of the plurality of second features Y into a carbohydrate recommendation classification model (e.g., the protein recommendation classifier described above with reference to FIG. 11). In some embodiments, the user is assigned either a low protein dietary recommendation (p) or a regular protein dietary recommendation (P). In some embodiments, the user is assigned either a low protein dietary recommendation (p), a regular protein dietary recommendation (P), or a high protein dietary recommendation (P+). In some embodiments, the user is assigned either a low protein dietary recommendation (p), a regular protein dietary recommendation (P), a high protein dietary recommendation (P+), or an extra high protein dietary recommendation (P++). In other embodiments, the carbohydrate macronutrient dietary recommendation is one of more than four classes of recommendations, e.g., one of five, six, seven, or more classes of recommendations.

In some embodiments, the method includes comparing the assigned macronutrient fat intake recommendation Fj, macronutrient carbohydrate intake recommendation $C_j$, and macronutrient protein intake recommendation $P_j$ to the plurality of diet types $D=\{D_1 \ldots, D_q\}$. In some embodiments, every combination of fat, carbohydrate, and protein dietary recommendations defines a different diet type. In other embodiments, certain combinations of fat, carbohydrate, and protein dietary recommendations are classified in a same diet type (for example, in the diet type classifications described above with respect to FIG. 5, FCP+ and FCP++ combinations both correspond to Diet Type 2). In yet other embodiments, one or more combination of fat, carbohydrate, and protein dietary recommendations is associated with more than one diet type, for example, based on one or more additional factors (e.g., a particular genotypic marker, phenotypic marker, metabolic adaptability feature, food preference, food religion, anthropometric feature, user goal, dietary pattern, or activity pattern).

In some embodiments, the food classifications and/or recommendations assigned to the user are used to provide ranked food recommendations 1548 using food selection classifier 1536. In some embodiments, the user's food classifications and/or recommendations, along with list of foods 1534 (e.g., a list of all meals in a menu database, or a sub-selection of meals, such as a menu of meals to be prepared on a particular week) are input into food selection classifier 1536, which optionally includes one or more of diet type prioritization algorithm 1538, preference filter 1540, allergy and/or sensitivity filter 1542, source filter 1544, and micronutrient ranking algorithm 1546. In various embodiments, any or all of these components are used in any order to rank foods for recommendation to a user.

In some embodiments, food selection classifier 1536 assigns a numerical value to one or more of foods 1536. In some embodiments, the numerical value for a particular food reflects both a diet type suitability of the food for a user and a micronutrient suitability of the food for a user. For example, in some embodiments, the food is assigned a first number corresponding to a diet type of the food and a second number corresponding to a micronutrient profile of the food. For example, a food assigned to a first Diet Type may be assigned a value of 1 and a food assigned to a second Diet Type may be assigned a value of 5. Then a second value is assigned to each food based on a similarity of the micronutrients in the food to a micronutrient recommendation profile of the user. In some embodiments, the two numbers are kept separate, e.g., as an ordered pair of numbers (X, Y) or X.Y. In other embodiments, the two numbers may be combined arithmetically, e.g., by generating a sum of the two numbers. In this fashion, the foods can then be ranked numerically to determine which foods are best suited for the user.

In some embodiments, Diet type prioritization algorithm 1538 filters or ranks foods (e.g., meals) based on a comparison between the diet type assigned to a user and a diet type assigned to the food (e.g., meal). For example, in some embodiments, each food is classified as belonging to one of the Diet Types (e.g., Diet Types 1-7, as described herein with reference to FIG. 5) and foods having the same Diet Type designation as a user's Diet Type assignment are prioritized over foods having different Diet Type designations as the user's Diet Type assignment. In some embodiments, a food having a Diet Type designation that is different from the user's Diet Type assignment is filtered out (e.g., removed from a list of eligible foods for the user).

In some embodiments, the food is assigned a Diet Type designation based on the fat, carbohydrate, and protein contents of the food. In some embodiments, the fat, carbohydrate, and protein contents of the food are used to classify the food according to the same fat, carbohydrate, and protein consumption recommendations assigned to users. For example, a food with a carbohydrate content below a threshold value (e.g., according to the percent of carbohydrates by weight or calories in the food) is assigned a low carbohydrate food designation (c) that corresponds to a low carbohydrate dietary recommendation (c). Conversely, a food with a carbohydrate content above a threshold value (e.g., according to the percent of carbohydrates by weight or calories in the food) is assigned a high carbohydrate food designation (C) that corresponds to a low carbohydrate dietary recommendation (C). Likewise, the food is assigned one of a plurality of fiber dietary recommendations (e.g., for F) and protein dietary recommendations (e.g., p or P; or p, P, or P+; or p, P, P+, or P++). The combination of fat, carbohydrate, and protein classification of the food is then mapped to a Diet Type (e.g., one of Diet Types 1-7, as described herein with reference to FIG. 5).

In some embodiments, preference filter 1540 is applied to deprioritize foods that does not comply with a user's preference (e.g., vegetarian, dairy-free, gluten free, kosher, etc.). In some embodiments, the system removes a food that does not comply with a user's preference from a list of eligible foods for the user.

In some embodiments, allergy/sensitivity filter 1542 is applied to deprioritize foods the user is allergic to and or is sensitive. In some embodiments, the system removes a food the user is allergic to or sensitive to from a list of eligible foods for the user. For example, in some embodiments, food selection classifier 1536 applies a sodium filter to deprioritize or remove meals with a sodium content above a threshold level when the user has been identified as having a salt sensitivity. In some embodiments, food sensitivities are determined based on a user feature 1504 (e.g., a genotype 1506, phenotype 1508, or metabolic adaptability characteristic).

In some embodiments, source filter 1544 is applied to deprioritize foods that do not comply with a source recommendation for the user (e.g., a MUFA or Fiber source recommendation as described herein with reference to FIG. 16). In some embodiments, the system removes a food that does not comply with a source recommendation for the user from a list of eligible foods for the user.

In some embodiments, micronutrient ranking algorithm 1546 is applied to prioritize foods with micronutrient profiles that most closely match a micronutrient recommendation profile assigned to the user (e.g., user micronutrient classifications 110 described herein with reference to FIG. 1 and/or micronutrient recommendation profile 1528 as described herein with reference to FIG. 15).

In some embodiments, food selection classifier 1536 adjusts the ranking of one or more meals (e.g., deprioritizes) belonging to a same meal family (e.g., meals having similar bases that vary, for example, primarily by the identity of the protein) as a higher ranked meal. For example, where a list of available meals includes both beef over noodles and chicken over noodles, the lower ranked meal will be deprioritized with in the ranking to avoid presenting the user with highly similar meal choices.

In some embodiments, the systems and methods described herein also include providing a caloric recommendation $C_j$ to the user by inputting a sixth sub-plurality $X_6$ of the plurality of first features X and a sixth sub-plurality $Y_6$ of the plurality of second features Y into a caloric recommendation classification model (e.g., caloric recommendation classifier 1524 illustrated in FIG. 15). In some embodiments, the caloric recommendation classifier uses features of the user, e.g., one or more of gender, age, height, weight, waist circumference, and activity levels, to assign a caloric recommendation (e.g., caloric recommendation 1532 illustrated in FIG. 15) to the user, for example, a recommendation on how many calories to consume at a single meal, an entire day, a week, etc.

In some embodiments, food selection classifier 1536 applies caloric recommendation 1532 to prioritize foods (e.g., meals) that closely match the user's caloric requirements. In some embodiments, the system deprioritizes a food (e.g., a meal) that does not conform with a user's caloric recommendation, e.g., a food with a calorie content that exceeds a maximum calorie content determined based on the user's caloric recommendation and/or a food with a calorie content less than a minimum calorie content determined based on the user's caloric recommendation. In some embodiments, the system removes a food that does not conform to a user's caloric recommendation from a list of eligible foods for the user.

In some embodiments, one or more ranked food recommendations 1548 are presented to the user, e.g., through a web-based user interface. In some embodiments, the ranked food recommendations correspond to meals that can be prepared and/or delivered to the user. The user selects user food selections 1550 from ranked food recommendations 1548, which are prepared and/or delivered to the user in some embodiments (e.g., as food delivery 1556 illustrated in FIG. 15).

In some embodiments, ranked food recommendations 1548 represent a sub-plurality of all available foods 1534, which most closely fit food classifications and/or recommendations for the user. In some embodiments, the user selects a number of meals to be displayed, e.g., 1, 2, 3, 4, 5, 6, 7, 8, 9, 10, or more meals for a particular week. In some embodiments, the user specifies the number and types of meals to be displayed, e.g., a certain number of breakfasts, a certain number of lunches, and a certain number of dinners. The system then selects the meals that best match the user's food profile (e.g., classifications and/or recommendations) and displays suggested meals to the user. In some embodiments, the system also displays one or more alternative meals to the user that the user may select in lieu of a suggested meal. In some embodiments, the alternative meals are those ranked just below the suggested meals by the food selection classifier.

In some embodiments, the system monitors and analyses user food selections 1550 over one or more user selection events and uses the information to refine food selection classifier 1536 for the user. For example, where the user consistently chooses an alternative meal containing chicken for a suggested meal containing salmon, the system may update food selection classifier 1536 for the user to more heavily weight meals containing chicken and/or less heavily weight meals containing salmon. In some embodiments, a learning classifier algorithm is implemented to refine the output of food selection classifier 1536 for the individual.

In some embodiments, the system monitors and analyses user food selections 1550 over one or more user selection events for a plurality of users and uses the information to refine a master list of meals (e.g., foods 1536), selection of meals for a particular menu (e.g., selection of foods 1534 from a master list of foods), and/or development of new meals to be added to a master list of meals. For example, if the system identifies a pattern that users select meals containing chicken more often than meals containing beef, the system may refine an algorithm used to select potential meals to offer chicken dishes more often and/or beef dishes less often on a global scale (e.g., for all or a subset of users of the system.)

In some embodiments, the methods and systems described herein apply features 1504 of the user to a supplement recommendation classifier (e.g., supplement recommendation classifier 1552 illustrated in FIG. 15) to provide a supplement recommendation (e.g., supplement recommendation 1554). In some embodiments, the supplements recommended to a user are selected from a predetermined list of supplements that address different health needs, e.g., one or more of metabolic health, cholesterol reduction, maintenance of polyunsaturated fat (e.g., omega-3 fatty acids) levels, blood pressure control, cardiac health, and general health (e.g., in a gender-specific or gender-neutral fashion).

In some embodiments, the supplement recommendation classifier ranks potential supplement recommendations for a user (e.g., based on a classifier that considers, for example, one or more of the importance of the supplement to health and the user's need for the particular supplement) and selects up to a predetermined number of supplement recommendations to provide the user (e.g., the top 2, 3, 4, 5, 6, 7, 8, 9, or more supplements). For example, in one embodiment, the supplement recommendation classifier may rank a first supplement over a second supplement because the first supplement has been shown to greatly reduce incidence of cardiac failure, while the second supplement has a largely cosmetic effect, regardless of the user's relevant needs for the two supplements. In another embodiment, the supplement recommendation classifier may rank the second supplement, with the largely cosmetic effect, higher than the first supplement, associated with greatly reduced incidence of cardiac failure, if a user has a much greater need for the second supplement than for the first supplement.

In some embodiments, a metabolic supplement is recommended to a user that would benefit from assistance with maintaining blood glucose levels. In one embodiment, a metabolic supplement contains one or more of green tea catechins and chromium picolinate, known to contribute to maintenance of normal blood sugar.

In some embodiments, a phytosterol supplement is recommended to a user that would benefit from assistance maintaining healthy cholesterol levels because phytosterols have been shown to reduce cholesterol levels.

In some embodiments, a cardiac health supplement is recommended to a user that would benefit from assistance maintaining a healthy cardiac system. In one embodiment, a cardiac health supplement contains one or more of coenzyme Q10 and grapeseed extract, both of which promote healthy blood vessels.

In some embodiments, an omega-3 fatty acid supplement is recommended to a user that would benefit from assistance maintaining healthy polyunsaturated fat levels. In one embodiment, an omega-3 fatty acid supplement contains one or more of fish oil and algal oil because EPA and DHA contribute to maintenance of healthy omega-3 fatty acid levels.

In some embodiments, an omega-3 fatty acid supplement is recommended to a user that would benefit from assistance lowering their blood pressure. In one embodiment, an omega-3 fatty acid supplement contains one or more of fish oil and algal oil because EPA and DHA contribute to maintenance of normal blood pressure.

In some embodiments, recommended supplements are delivered to the user (e.g., along with user food selections as part of food delivery 1556). In some embodiments, as a consequence of providing the user with one or more recommended supplements, the system provides feedback to one or both of the food selection classifier engine (e.g. meal ranker engine 125 as described herein with reference to FIG. 1 and/or food selection classifier 1536 as described herein with reference to FIG. 15) and hero food recommendation engine, that the user has been provided a supplement. In some embodiments, the food selection classifier engine and/or hero food recommendation engine considers that the user is taking supplements when making a future food recommendation. For example, in some embodiments, in response to an input that the user has or will be provided a fish oil supplement, the food selection classifier deprioritizes foods (e.g., meals) containing fish and/or foods (e.g., meals) high in omega-3 fatty acids, because the user is receiving a large amount of omega-3 fatty acids from the fish oil supplements. In one embodiment, the system will remove a food (e.g., a meal) containing fish and/or high in omega-3 fatty acids, from a list of foods available to the user while the user is receiving fish oil supplements. Likewise, in some embodiments, a hero food recommendation engine (e.g., meal ranker engine 125 in FIG. 1 and/or hero food recommendation classifier engine 1525 in FIG. 15) deprioritizes and/or removes a hero food recommendation high in omega-3 fatty acids while the user is receiving fish oil supplements.

In some embodiments, the systems and methods described herein also include providing a hero food recommendation $H_j$ to the user by inputting a seventh sub-plurality $X_7$ of the plurality of first features X and a seventh sub-plurality $Y_7$ of the plurality of second features Y into a hero food recommendation classification model (e.g., a meal ranker engine 125 as described herein with respect to FIG. 1 and/or a hero food recommendation classifier engine 1525 as described herein with respect to FIG. 15). In some embodiments, the hero food recommendation classifier uses features and/or Diet Type assignments to recommend one or more hero foods (e.g., one or more hero foods shown in FIG. 14) to the user.

It should be understood that the particular order in which the operations in the methods and systems described above with respect to FIG. 15 have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to methods and systems described above with respect to FIG. 15. For example, information collection methods, the classifiers, genotypes, phenotypes, vitals, communication networks, computer infrastructures, etc. described above with reference to FIG. 15 optionally have one or more characteristics of the information collection methods, classifiers, genotypes, phenotypes, vitals, communication networks, computer infrastructures, etc. described with reference to FIG. 1. For brevity, these details are not repeated here.

In some embodiments, the methods described herein include assigning one or more source recommendation to an individual. In some embodiments, the source recommendations include a fiber source recommendation, suggesting that the user eat foods higher in fiber (e.g., a recommendation that the user consumes foods with a minimum amount of fiber or in which a minimum percentage of carbohydrates are fibers). In some embodiments, the source recommendations include a monounsaturated fatty acid source recommendation, suggesting that the user eat foods higher in monounsaturated fatty acids (e.g., a recommendation that the user consumes foods with a minimum amount of monounsaturated fatty acids or in which a minimum percentage of fats are monounsaturated fatty acids).

FIG. 16 shows an illustrative classifier for providing monounsaturated fatty acid (MUFA) and fiber source recommendations (e.g., an exemplary source recommendation profile $S_j$, as illustrated in FIG. 15), in accordance with some embodiments. In some embodiments, a classifier providing source recommendations is implemented as part of a micronutrient recommendation classifier, e.g., as illustrated in FIG. 15. In other embodiments, a classifier providing source recommendations is implemented separate from a micronutrient recommendation classifier.

In FIG. 16, user features (e.g., genotypes, phenotypes, vitals, anthropometrics, and metabolic adaptability traits) that lead to a MUFA or Fiber source recommendation are shown of the left hand side of the table. The source recommendation assigned to the user trait is represented by an 'X' on the right side of the table. For example, identifying the user as having elevated blood pressure results in both a MUFA and a fiber recommendation, in accordance with some embodiments. (*) Individuals with an increased waist circumference (WC) plus the FTO risk variant will also get a fiber recommendation because of their increased WC (e.g., independent of their rs9939609 allele status). (**) Individuals with a low disposition index with impaired fasting glucose (IFG), impared glucose tolerance (IGT), or IGT & IFG will also get a fiber recommendation because of their IFG, IGT, or IGT & IFG.

In some embodiments, the methods described herein include providing the user with information about their metabolic flexibility associated with consuming one or more of fats, carbohydrates, and protein. For example, FIG. 17 shows an illustrative classifier for providing the user with information about their metabolic flexibility associated with consuming protein, in accordance with some embodiments. In FIG. 17, user features (e.g., genotypes, phenotypes, vitals, anthropometrics, and metabolic adaptability traits) that result in information about a user's protein consumption flexibility are shown of the left hand side of the table. The flexibility associated with the user's feature is shown on the right side of the table. For example, determining the user has elevated blood pressure identifies the user as having flexibility to consume a diet rich in protein (e.g., in which 18-30% of the user's calories come from protein).

FIG. 18 shows an illustrative classifier for providing micronutrient recommendations based on user features (e.g., as described above with respect to health decision tree engine 108 in FIG. 1 and/or micronutrient recommendation classifier 1522 in FIG. 15), in accordance with some embodiments. In FIG. 18, user features (e.g., genotypes, phenotypes, vitals, anthropometrics, and metabolic adaptability traits) determinative of a micronutrient recommendation are displayed across the top of the table, while the micronutrient is identified at the left of the table.

Figure 20:
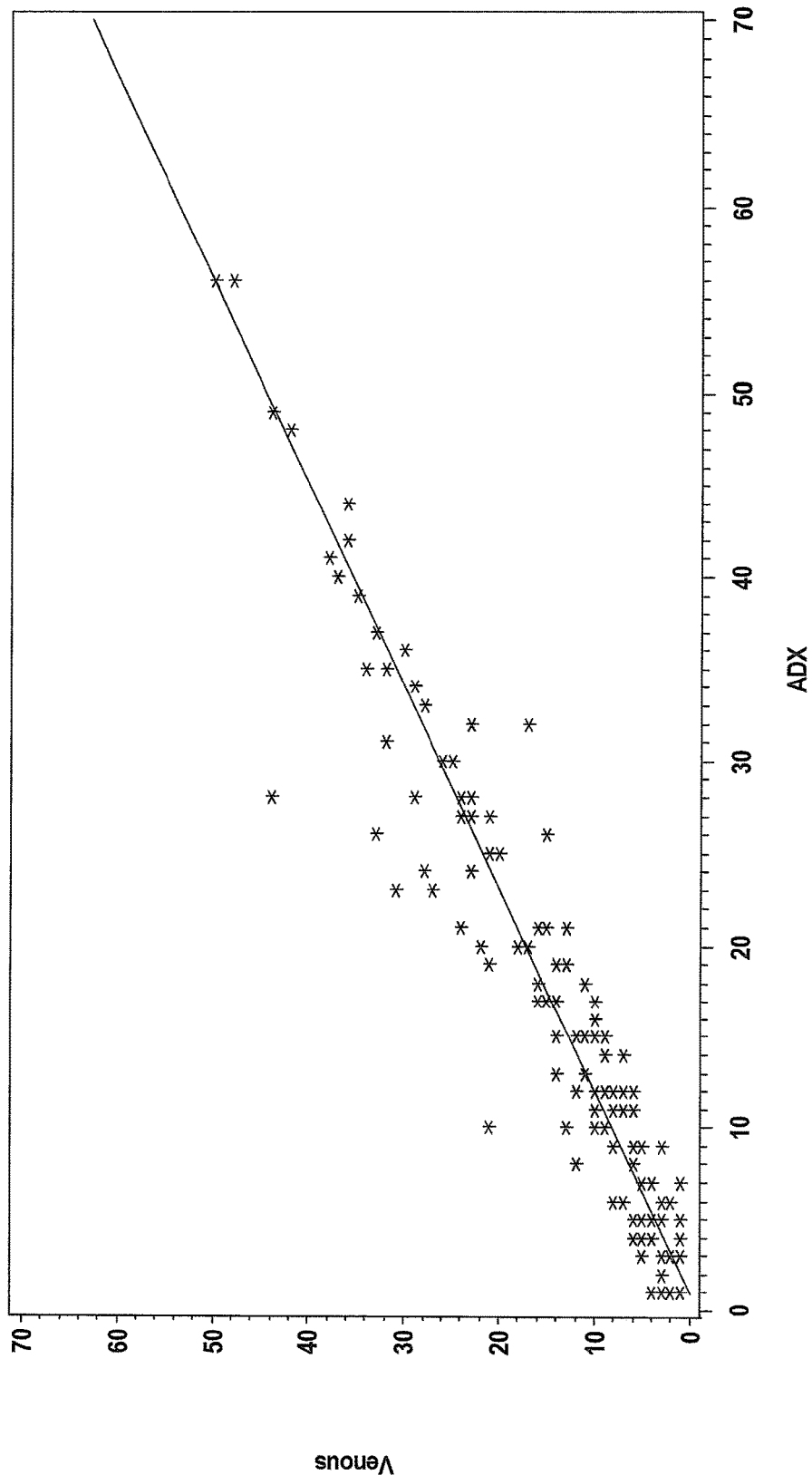
FIG. 20 depicts an illustrative classifier for determining carbohydrate micronutrient recommendations based on vitals, genotypic and/or phenotypic data in accordance with some embodiments.

In some embodiments, a default micronutrient recommendation is provided (e.g., one associated with a daily recommended intake for the micronutrient) and the system modifies the micronutrient recommendation when detecting a user feature associated with an increased need for, or beneficial results of, consuming more or less of the particular micronutrient. For example, as illustrated in FIG. 17, baseline recommendations (DRI) for the micronutrient are shown in the column next to the micronutrient. Modified micronutrient recommendations for a user identified with a particular feature are shown below the feature identified and in-line with the micronutrient. For example, as illustrated in FIG. 20, a user identified as having elevated or high impaired glucose tolerance (e.g., as identified using a challenge beverage test as further described herein) is assigned one or more of the following recommendations: that they consume 90 grams of whole grains, that 5 grams out of every 100 grams of carbohydrates they consume are alpha-cyclodextrin, 8 grams out of every 100 grams of carbohydrates they consume are arabinoxylan, 3.5 grams out of every 100 grams of carbohydrates they consume are beta-glucans, and 14 grams of every 100 grams of carbohydrates they consume are resistant starch.

In some embodiments, the systems and methods provided herein apply classifiers providing recommendations for one or more of the micronutrients listed in FIG. 8. In some embodiments, a micronutrient classifier is informed by studies linking improved health to the administration of a micronutrient to subjects with a specific feature (e.g., genotype, phenotype, metabolic flexibility, anthropometric characteristic, etc.).

In one embodiment, the disclosure provides a method 2800 for providing personalized food recommendations. The method includes obtaining (2802) feature data about a user, for example, one or more features as described herein with reference to FIG. 1 (e.g., via user health database 105), FIG. 2 (e.g., storing (202) user vitals, genotypic, and phenotypic data), FIG. 3 (e.g., illustrative phenotypes), FIG. 4 (e.g., illustrative genotypes), FIG. 10 (e.g., user vitals data 1002, user phenotypic data 1004, and user genotypic data 1006), and FIG. 15 (e.g., feature data 1504). In some embodiments, the user feature data includes one or more of a plurality of genotypic markers $X=\{x_1 \ldots, x_m\}$ (2804) of the user, a plurality of phenotypes $Y=\{y_1 \ldots, y_n\}$ (2806) of the user, one or more metabolic adaptability characteristics (2808), e.g., as identified using a multi-nutrient challenge beverage, one or more food preference (2810), one or more user goals (2814), one or more user dietary patterns (2816), and one or more user activity patterns (2818).

In some embodiments, the method includes assigning (2820) a respective diet type $D_j$ in a plurality of diet types $D=\{D_1 \ldots, D_q\}$ (e.g., diet types 1-7 as described herein with reference to FIG. 5) to the user by inputting user features, including a first sub-plurality $X_1$ of the plurality of first features $X$ and a first sub-plurality $Y_1$ of the plurality of second features $Y$, into a diet type classification model (e.g., health decision tree engine 108 as described herein with reference to FIG. 1 and/or diet type classifier 1520 as described herein with reference to FIG. 15).

In some embodiments, assigning a respective diet type includes (2822): assigning a macronutrient fat intake recommendation $F_j$ to the user by inputting a third sub-plurality $X_3$ of the plurality of first features $X$ and a third sub-plurality $Y_3$ of the plurality of second features $Y$ into a fat recommendation classification model (e.g., as described herein with reference to FIG. 12), assigning a macronutrient carbohydrate intake recommendation $C_j$ to the user by inputting a fourth sub-plurality $X_4$ of the plurality of first features $X$ and a fourth sub-plurality $Y_4$ of the plurality of second features $Y$ into a carbohydrate recommendation classification model (e.g., as described herein with reference to FIG. 11), and assigning a macronutrient protein intake recommendation $P_j$ to the user by inputting a fifth sub-plurality $X_5$ of the plurality of first features $X$ and a fifth sub-plurality $Y_5$ of the plurality of second features $Y$ into a protein recommendation classification model (e.g., as described herein with reference to FIG. 13).

In some embodiments, the method includes assigning (2824) a micronutrient recommendation profile $R_j=\{r(z_i) \ldots, r(z_s)\}$ including a recommendation $r(z_i)$ for each respective micronutrient $z_i$ in a plurality of micronutrients $Z=\{z_1 \ldots, z_s\}$ to the user by inputting user features, including a second sub-plurality $X_2$ of the plurality of first features $X$ and a second sub-plurality $Y_2$ of the plurality of second features $Y$, into a micronutrient classification model (e.g., health decision tree engine 108 as described herein with reference to FIG. 1 and/or micronutrient recommendation classifier 1520 as described herein with reference to FIG. 15).

In some embodiments, the method includes assigning (2826) one or more source recommendations $S_j$ to the user by inputting user features, including a sub-plurality of first features $X$ and a sub-plurality of second features $Y$, into a source classification model (e.g., micronutrient recommendation classifier 1520 as described herein with reference to FIG. 15 or a classifier implemented separately from micronutrient recommendation classifier 1520 and/or a an illustrative source classifier as described herein with reference to FIG. 16). In some embodiments, a source recommendation includes a recommendation for dietary fiber (e.g., as described herein with reference to FIGS. 15 and 16). In some embodiments, a source recommendation includes a recommendation for dietary monounsaturated fatty acids (e.g., as described herein with reference to FIGS. 15 and 16).

In some embodiments, the method includes assigning (2832) a caloric recommendation $C_j$ to the user by inputting user features into a caloric recommendation classification model (e.g., caloric recommendation classifier 1525 as described herein with reference to in FIG. 15). In some embodiments, the caloric recommendation is based on a user daily activity level (2834). For example, in some embodiments the user is presented with a questionnaire asking about their physical activity levels during a normal day (e.g., at work, school, and/or home). In some embodiments, the caloric recommendation is based on a user exercise level (2836). For example, in some embodiments, the user is presented with a questionnaire asking about the physical activities they routinely engage in (e.g., sports, weightlifting, cardiovascular exercising, and outdoor activities). For example, the user is asked about one or more of what activities they routinely participate in, how often they participate in the activities, and how vigorously they participate in the activities. In some embodiments, activity information is provided by an electronic activity monitor. In some embodiments, the user's reported daily physical activity levels and/or leisure activity levels are weighted according to a model of the caloric output and/or caloric requirement for each activity and then used to arithmetically personalize a daily caloric requirement, e.g., as based off of a starting caloric requirement for a male or female, optionally considering other features of the individual (e.g., one or more phenotype, metabolic adaptability characteristic, or anthropometric measurement).

In some embodiments, the method includes assigning (2838) one or more hero food recommendations $H_j$ (e.g., one or more hero foods as described herein with reference to FIG. 14) to the user by inputting user features, including a sub-plurality of first features $X$, a sub-plurality of second features $Y$, and/or a dietary type, into a hero food recommendation classification model (e.g., caloric recommendation classifier 1525 as described herein with reference to in FIG. 15).

In some embodiments, the method includes assigning (2838) one or more supplement recommendations $V_j$ to the user by inputting user features, including a sub-plurality of first features $X$ and a sub-plurality of second features $Y$, into a supplement recommendation classification model (e.g., supplement recommendation classifier 1552 as described herein with reference to in FIG. 15).

In some embodiments, the method includes recommending one or more foods to the user by inputting (F) one or more of the user features and/or recommendations into a food recommendation classifier (e.g., meal ranker engine 125 as described herein with reference to FIG. 1 and/or food selection classifier 1536 as described herein with reference to FIG. 15). In some embodiments, a plurality of foods (e.g., a plurality of meals) is input into the classifier and the food recommendation classifier selects one or more foods (e.g., meals) that best match the dietary needs of the user based on the one or more user features and/or recommendations.

For example, in one embodiment, the method includes ranking (2842) one or more foods in a plurality of foods $L=\{N_1 \ldots, N_t\}$ (e.g., a list of meals), where each respective food $N_i$ in the plurality of foods has a corresponding nutrition profile $P_{Ni}=\{D_{ki}, P(z_{ki})\}$ comprising an assigned diet type $D_k$ in the plurality of diet types D and an assigned micronutrient profile $P(z_k)=\{v(z_1) \ldots, v(z_s)\}$, where the micronutrient profile $P(z_k)$ includes a respective value $v(z_i)$ for each micronutrient $z_i$ in the plurality of micronutrients Z.

In some embodiments, ranking one or more foods includes deprioritizing (2844) a food $N_i$ that does not conform to a user preference. For example, deprioritizing a meal containing chicken for a user with a vegetarian preference. In some embodiments, deprioritizing (2846) includes assigning the food a lower rank in the ranking of the one or more foods in the plurality of foods L. For example, assigning a meal containing beef a lower ranking than a meal containing salmon for a user with a preference for fish as a protein. In some embodiments, deprioritizing (2848) includes removing the food from a list of eligible foods for the user. For example, removing a dish containing pork as an option for a user with a kosher food preference. In some embodiments, different types of food preferences will result in different rules for food prioritization. For example, in one embodiment, a preference for a particular food religion will result in removing a food from a list of foods available to the user, while a preference for a particular protein source may just prioritize meals containing that protein as compared to meals containing other proteins.

In some embodiments, ranking one or more foods includes prioritizing (2850) foods N by comparing the diet type $D_j$ assigned to the user with the diet types $D_k$ assigned to each food $N_i$. In some embodiments, prioritizing (2852) includes assigning a food $N_1$ having a same diet type $D_{k1}$ as the diet type $D_j$ assigned to the user a higher rank in the ranking of the one or more foods than a food $N_2$ having a different diet type $D_{k2}$ as the diet type $D_j$ assigned to the user. For example, ranking a meal having a high protein content higher than a meal containing a low protein content for a user with a diet type associated with a high protein requirement (e.g., associated with a P+ or P++ dietary protein recommendation as described herein). In some embodiments, prioritizing (2854) includes removing a food $N_3$ having a different diet type $D_{k3}$ as the diet type $D_j$ assigned to the user from a list of eligible foods for the user, e.g., the plurality of foods. For example, removing a meal having a high carbohydrate content and low protein content from a list of available foods for a user with a diet type associated with a high protein requirement (e.g., associated with a P+ or P++ dietary protein recommendation as described herein) and a low carbohydrate requirement (e.g., associated with a c dietary carbohydrate recommendation as described herein).

In some embodiments, ranking one or more foods includes deprioritizing (2856) a food $N_i$ that does not conform to a user allergy and/or sensitivity. For example, deprioritizing a meal high in caffeine for a user with a caffeine sensitivity. In some embodiments, deprioritizing (2858) includes assigning the food a lower rank in the ranking of the one or more foods in the plurality of foods L. For example, assigning a meal containing a cream sauce a lower ranking than a meal containing a tomato sauce for a user with a lactose sensitivity. In some embodiments, deprioritizing (2860) includes removing the food from a list of eligible foods for the user. For example, removing a dish containing peanut butter as an option for a user with a peanut allergy. In some embodiments, different types of food sensitivities and allergies will result in different rules for food prioritization. For example, in one embodiment, a peanut allergy will result in removing a food from a list of foods available to the user, while sensitivity for caffeine may just result in deprioritizing meals containing caffeine.

In some embodiments, ranking one or more foods includes deprioritizing (2862) foods N by comparing the source recommendation $S_j$ assigned to the user with the nutrition profile $P_N$ of each food e.g., deprioritizing a food $N_i$ that does not conform to a user source recommendation. For example, deprioritizing a meal low in fiber for a user with a fiber source recommendation. In some embodiments, deprioritizing (2864) includes assigning a food $N_1$ that does not conform to a user source recommendation a lower rank in the ranking of the one or more foods than a food $N_2$ that does conform to a user source recommendation. For example, assigning a meal with high fiber content above a meal having low fiber content for a user with a fiber source recommendation. In some embodiments, deprioritizing (2866) includes removing the food from a list of eligible foods for the user. For example, removing a dish having a low fiber content as an option for a user with fiber source recommendation. In some embodiments, different types of source recommendations will result in different rules for food prioritization. For example, in one embodiment, a fiber source recommendation with result in the removal of foods with low fiber content, while a monounsaturated fatty acid source recommendation will result in the prioritization of foods rich in monounsaturated fatty acids.

In some embodiments, ranking one or more foods includes prioritizing (2868) foods N by comparing the micronutrient recommendation profile assigned to the user with the micronutrient profile $P(z_{ki})$ assigned to each food $N_i$. In some embodiments, prioritizing (2870) includes assigning, within a diet type $D_k$, a food $N_1$, having a micronutrient profile $P(z_{k1})$ that more closely matches the user's micronutrient recommendation profile $R_j$ than the micronutrient profile $P(z_{k2})$ of a food $N_2$ having the same diet type as food $N_1$, a higher ranking than food $N_2$.

In some embodiments, ranking one or more foods includes deprioritizing (2872) (e.g., further lowering a ranking of) a food $N_1$ having a lower ranking than a food $N_2$ when food $N_1$ and food $N_2$ belong to a same food family. For example, where two meals are substantially identical other than for the identity of the protein (e.g., a chicken dish and a beef dish served over rice), if the chicken dish is ranked higher than the beef dish, the beef dish is deprioritized with respect to other, previously lower ranked dishes, in order to provide the user with diverse food choices/recommendations.

In some embodiments, ranking one or more foods includes deprioritizing (2874) a food $N_i$ by comparing a supplement recommended to the user to the nutrition profile $P_N$ of each food N. For example, where the method includes recommending and/or delivering a nutrient supplement in addition to one or more foods, the system will compensate for the nutrients by deprioritizing foods rich in that nutrient. In some embodiments, deprioritizing (2876) includes lowering the ranking of food $N_1$ that is rich in a nutrient present in the supplement recommended to the user. For example, where the user is receiving a fish oil supplement, a meal containing salmon is ranked below a meal containing chicken because salmon is rich in omega-3 fatty acids. In some embodiments, deprioritizing (2878) includes removing a food $N_1$ that is rich in a nutrient present in the supplement recommended to the user from a list of eligible foods for the user. For example, where the user is receiving a fish oil supplement, a meal containing salmon is removed from a list of foods eligible to the user. In some embodiments, different supplement recommendations will result in different rules for food prioritization. For example, in one embodiment, receiving a fish oil supplement will remove meals containing salmon as an available food, while receiving a multivitamin supplement will result in lowering a ranking of a food rich in one of the vitamins in the supplement.

In some embodiments, ranking one or more foods includes deprioritizing (2880) foods N by comparing a caloric recommendation $C_j$ assigned to the user with the nutrition profile $P_N$ of each food $N_i$. For example, ranking a higher calorie meal above a lower calorie meal for an extremely active user with a high caloric recommendation. In some embodiments, deprioritizing (2882) includes assigning a food $N_1$ that does not conform to a user caloric recommendation a lower rank in the ranking of the one or more foods than a food $N_2$ that does conform to a user caloric recommendation. In some embodiments, deprioritizing (2884) includes removing a food $N_1$ that does not conform to a user caloric recommendation from a list of eligible foods for the user.

In some embodiments, the method includes presenting (2886) to the user a sub-plurality of ranked foods from the list of ranked foods for selection of one or more foods to be prepared and/or delivered to the user. For example, after ranking a group of 100 foods, the system displays the five foods ranked highest according to the ranking classifier (e.g., meal ranker engine 125 as described herein with respect to FIG. 1 and/or food selection classifier 1536 as described herein with reference to FIG. 15). In some embodiments, presenting (2888) includes providing (2888) at least one primary food recommendation and at least one secondary food recommendation that the user may substitute for the primary food recommendation. For example, he system displays to the user the highest ranked food according to the ranking classifier as the default food for the user, but also displays the second highest ranked food according to the ranking classifier as a substitute for the default food.

In some embodiments, the method includes preparing and/or delivering (2890) a food selected (G) for the user based on a system recommendation (e.g., a food selected based on a recommendation from a diet type classifier, a micronutrient recommendation classifier, a source recommendation classifier, a hero food recommendation classifier, a supplement recommendation classifier, and/or a food selection classifier). In some embodiments, the food is selected based on a diet type $D_j$ assigned to the user (2892). In some embodiments, the food is selected based on a micronutrient recommendation profile $R_j$ assigned to the user (2894). In some embodiments, the food is selected based on a source recommendation $S_j$ assigned to the user (2898). In some embodiments, the food is a hero food selected based on a hero food recommendation $H_j$ assigned to the user (2898). In some embodiments, the food is a supplement selected based on a supplement recommendation $V_j$ assigned to the user (2902). In some embodiments, the food is selected based on a ranking of foods from a list of foods available to the user (2904). In some embodiments, the food is a prepared meal (2906). In some embodiments, the food is selected by the user based on a ranking of foods presented to the user (2908). In some embodiments, the food is a prepared meal (2910).

In some embodiments, the method includes providing (2912) the user with a food recommendation based (H) on a system recommendation (e.g., a food selected based on a recommendation from a diet type classifier, a micronutrient recommendation classifier, a source recommendation classifier, a hero food recommendation classifier, a supplement recommendation classifier, and/or a food selection classifier). In some embodiments, the food recommendation is based on a diet type $D_j$ assigned to the user (2914). In some embodiments, the food recommendation is based on a micronutrient recommendation profile $R_j$ assigned to the user (2914). In some embodiments, the food recommendation is based on a source recommendation $S_j$ assigned to the user (2916). In some embodiments, the food recommendation is based on a hero food recommendation $H_j$ assigned to the user (2918). In some embodiments, the food recommendation is based on a supplement recommendation $V_j$ assigned to the user (2920). In some embodiments, the food recommendation is based on a caloric recommendation $C_j$ assigned to the user.

Figure 29:
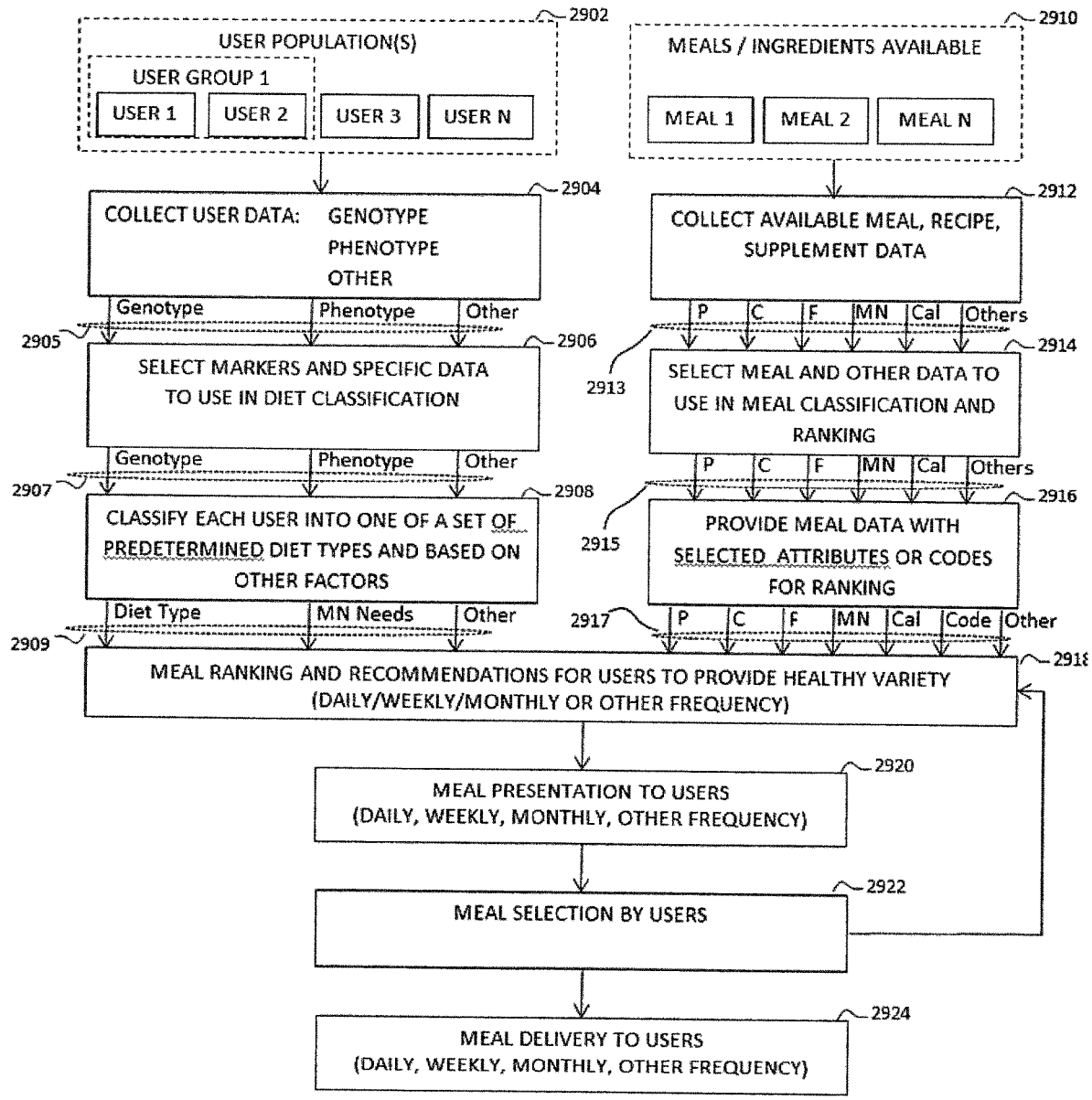
FIG. 29 depicts an illustrative method of collecting data from users and about meals and available ingredients and classifying the users into diet types and the meals according to their data in order to match users with a variety of different, healthy meal options on a daily, weekly, monthly or other frequency basis that are individualized for the user and that may be delivered to the user, in accordance with some embodiments.

FIG. 29 depicts an illustrative method of collecting data from users and about meals and available ingredients and classifying the users into diet types and the meals according to their data in order to match users with a variety of different, healthy meal options on a daily, weekly, monthly or other frequency basis that are individualized for the user and that may be delivered to the user. Referring to FIG. 29, there is a user population 2902 associated with a system according to some embodiments of the invention for making meal, food, recipe and supplement recommendations to each user. In 2904, each user provides information a DNA sample and a blood sample as described in this application from which genotype and phenotype data may be obtained. In addition other information including but not limited to vitals, goals, and exercise is collected.

In 2906 the collected genotype, phenotype and other data 2905 is stored or otherwise made available on the system and for each user, specific genotypical and phenotypical biomarkers are selected for use in classifying a user according to a diet type. In addition in 2906, certain data from the other data is selected to be used in the classification of each user into a diet type. The biomarkers selected may change over time. In 2908, each user is classified into a diet type that is stored on the system for that user along with data corresponding to the user's micronutrients needs and other information that is useful for selecting meals for the user such as calories, allergies and other information described elsewhere herein. This information 2909 including diet types, micronutrient needs and other information may be provided to the meal ranking and recommendation algorithm.

In addition to a population of users of the system, a set of meals and/or ingredients are available. The meals may include foods, prepared meals, supplements or recipes. Data corresponding to each meal, supplement or food is collected in 2912 and stored. In 2914, data associated with each meal 2913 is received and processed in order select a subset of data or to create new data corresponding to the meal that will be used in meal selection for the user.

In 2916, the system receives selected data associated with the meal such as protein, carbohydrates, fats, micronutrient data, calories and other detailed information as described elsewhere herein and optionally codes the meals in a form that facilitates correlating meals with diet types and ranking them. For example, a meal might be coded 0, 5 or 10 and if there are six diet types, all codes 0, 5 or 10 might be available for consumption by certain diet types. However, for others only meal types 5 and 10 might be available, while for still others only diet type 0 may be available. In any event, the meals may be coded and the code used along with a map correlating diet type with acceptable codes in a meal ranking algorithm. The selected meal data, micronutrient data and any selected codes 2017 may be provided to the meal ranking process 2918.

In 2918, a meal ranking and recommendation is performed in order to provide a healthy variety of food recommendations to a user on a daily, weekly, monthly or other basis. The recommendations, which may be a ranked subset from a large number of choices compatible with a user's diet type and micronutrient needs, may be of food, supplements, recipes, prepared meals, or hero foods as described elsewhere herein, including in connection with FIGS. 1 and 15, the meal ranker engine 125 and the element 1536. In 2920, the meals recommended for each user are presented to the corresponding user through email, messaging or the user logging in to the system and being presented with them there. The user selects a meal or multiple meals, foods, recipes or supplements in 2922 for the day, week or month. The user is presented with a healthy variety of meals that are each a match for the user's genotype and phenotype and the user's selections may also be fed back into the meal ranker 2918 as shown so that the user's preferences are considered in the recommendation. In 2924, selected meals, foods, or supplements may be delivered to the user.

Classifiers

In some embodiments, classifiers for determining nutritional recommendations based on user vitals, genotypic and/or phenotypic data can be developed or refined by training a decision rule using data from one or more training sets and applying the trained decision rule to data from users interested in receiving nutritional recommendations. Information on pattern recognition and prediction algorithms for use in data analysis algorithms for constructing decision rules if found, for example, in National Research Council; Panel on Discriminant Analysis Classification and Clustering, Discriminant Analysis and Clustering, Washington, D.C.: National Academy Press and Dudoit et al., 2002, "Comparison of discrimination methods for the classification of tumors using gene expression data." JASA 97; 77-87, the entire contents of which are hereby incorporated by reference herein in their entirety for all purposes.

In some embodiments, a classifier for determining nutritional recommendations based on user vitals, genotypic, and/or phenotypic data (e.g., for classifying a diet type, one or more macronutrient recommendation, one or more micronutrient recommendation, one or more source recommendation, or one or more hero food recommendation, or one or more food ranking or recommendation) may be built de novo by compiling existing clinical study results, performing and/or integrating new clinical study results, and/or observational theory. In some embodiments, one or more classifiers are further refined after implementation based on individual or population feedback.

For example, in an embodiment where the metabolic adaptability of an individual (e.g., as determined using a multi-nutrient challenge beverage) informs a diet type classifier, the metabolic adaptability of the individual may be determined one or more times following adaption of a particular diet type to track changes in the individual's metabolic adaptability following implementation of a particular diet. In this fashion, detrimental changes to the user's metabolic adaptability when on a particular diet can be identified and the diet type classifier can be refined such that the individual is classified into a more suitable diet type.

In some embodiments, a refined classifier is implemented in a user-independent fashion, e.g., refinement of a particular classifier based on data from a plurality of users leads to a change in a diet type classifier used to assign diet types to all users. In other embodiments, a refined classifier is implemented in a user-specific fashion, e.g., refinement of a food selection classifier based on observations that a particular user chooses certain types of meals (e.g., meals containing quinoa, or does not choose certain types of foods (e.g., meals including salmon as a protein), leads to a change in the food selection classifier implemented for that specific user, but not other users.

Relevant algorithms for decision rule include, but are not limited to: discriminant analysis including linear, logistic, and more flexible discrimination techniques (see, e.g., Gnanadesikan, 1977, Methods for Statistical Data Analysis of Multivariate Observations, New York: Wiley 1977; tree-based algorithms such as classification and regression trees (CART) and variants (see, e.g., Breiman, 1984, Classification and Regression Trees, Belmont, Calif.: Wadsworth International Group; generalized additive models (see, e.g., Tibshirani, 1990, Generalized Additive Models, London: Chapman and Hall; neural networks (see, e.g., Neal, 1996, Bayesian Learning for Neural Networks, New York: Springer-Verlag; and Insua, 1998, Feedforward neural networks for nonparametric regression In: Practical Nonparametric and Semiparametric Bayesian Statistics, pp. 181-194, New York: Springer, the entire contents of each of which are hereby incorporated by reference herein. Other suitable data analysis algorithms for decision rules include, but are not limited to, logistic regression, or a nonparametric algorithm that detects differences in the distribution of feature values (e.g., a Wilcoxon Signed Rank Test (unadjusted and adjusted)).

In some embodiments, the decision rule is based on multiple measured values, e.g., two, three, four, five, ten, twenty, or more measured values, corresponding to observables from multiple data sets, e.g., two, three, four, five, ten, twenty, or more data sets. In some embodiments, decision rules may also be built using a classification tree algorithm. Other data analysis algorithms known in the art include, but are not limited to, Classification and Regression Tree (CART), Multiple Additive Regression Tree (MART), Prediction Analysis for Microarrays (PAM), and Random Forest analysis. Such algorithms classify complex spectra and/or other information in order to distinguish subjects as normal or as having a particular medical condition. Other examples of data analysis algorithms include, but are not limited to, ANOVA and nonparametric equivalents, linear discriminant analysis, logistic regression analysis, nearest neighbor classifier analysis, neural networks, principal component analysis, quadratic discriminant analysis, regression classifiers and support vector machines. Such algorithms may be used to construct a decision rule and/or increase the speed and efficiency of the application of the decision rule and to avoid investigator bias. For further review of algorithm classifiers, see Duda, 2001, Pattern Classification, John Wiley & Sons, Inc., New York. pp. 396-408 and pp. 411-412, Hastie et al., 2001, The Elements of Statistical Learning, Springer-Verlag, New York, Chapter 9, and Breiman, 1999, "Random Forests—Random Features," Technical Report 567, Statistics Department, U. C. Berkeley, September 1999, the entire contents of which are hereby incorporated by reference herein in their entireties for all purposes.

Challenge Beverage

A challenge food or beverage may be used to evaluate a user's biological response to various foods and macronutrients. Exogenous factors, including food and drink, constantly stress our body's capacity to maintain physiological homeostasis. Our body's ability to adequately react to these external challenges to maintain homeostasis is termed "phenotypic flexibility." Phenotypic flexibility is determined by a series of interconnected physiological processes and molecular mechanisms. Challenge tests that temporarily disturb homeostasis, including challenge tests based on carbohydrates (oral glucose tolerance test, OGTT), lipids (oral lipid tolerance test, OLTT), protein (oral protein tolerance test, OPTT), and/or combinations thereof, have been used to test these processes and access phenotypic flexibility.

Challenge tests based on individual macronutrients may not be representative of an individual's diet. Furthermore, effects elicited by single macronutrient challenges do not include all process associated with phenotypic flexibility. A mixed macronutrient challenge test is used to evaluate all processes triggered by each individual challenge test at once and also to trigger all physiological systems representative of phenotypic flexibility. According to some embodiments, a challenge test includes consuming a food that includes relative large quantities of glucose, lipids, and protein. According to some embodiments, the challenge beverage includes only glucose, lipids or protein in large quantities, or a combination of them. In some embodiments, the challenge food is a beverage or a solid food. According to some embodiments, a challenge beverage includes or is made with the following ingredients:

| Ingredient | Weight in mg | Percentage by Weight |
|---|---|---|
| Water | 268.106 | 60.922 |
| Organic Palm Oil - Olein 18 C.; fully melted | 60.000 | 13.634 |
| Dextrose; Non-GMO | 83.380 | 18.947 |
| MPI 90 | 23.350 | 5.306 |
| Canola lecithin - Non GMO | 0.933 | 0.212 |
| Natural Flavors | 3.525v | 0.801 |
| gellan gum | 0.132 | 0.030 |
| Trisodium Citrate | 0.570 | 0.130 |
| Sodium Hydroxide 10% | 0.084 | 0.019 |
| | 440.080 | 100.000 |

In some embodiments, the water is heated and mixed with the other ingredients. The natural flavors may include vanilla in some embodiments or *cassia* flavors or combinations of both. In some embodiments, the natural flavors may be entirely different, or encompass other flavors in combination with natural flavors identified herein. The beverage in some embodiments is sterilized, homogenized and packed. The sterilization in some embodiments is by direct steam injection. The challenge beverage serving size in some embodiments is approximately 415 mg. However, the overall portion may be much smaller or larger depending on a range of factors, including the size of the individual, the expected range of the test results, the number of types of macronutrients present in the challenge beverage and taste. There may be in some embodiments multiple challenge beverage or food options for a single person to take multiple tests. Alternatively, there may be in some embodiments multiple challenge beverages available to choose from, including different sizes or flavors based on the personal preference of the user. In some embodiments, a blood test is done prior to the consumption of a challenge beverage. Bood tests at time intervals are done as described above after a user consumes a challenge beverage.

An example challenge beverage in some embodiments may comprise:

| | |
|---|---|
| Total Fat | 61 g |
| Saturated Fat | 26 g |
| Trans Fat | 0 g |
| Polyunsaturated Fat | 7 g |
| Monounsaturated Fat | 25 g |
| Cholesterol | 15 mg |
| Sodium | 150 mg |
| Total Carbohydrates | 77 g |
| Dietary Fiber | 0 g |
| Sugars | 75 g |
| Protein | 20 g |

In some embodiments, the disclosure provides a multi-nutrient challenge beverage for measuring the metabolic adaptability of a user containing fats, carbohydrates, and proteins. In some embodiments, the multi-nutrient challenge beverage contains from 44 to 66 grams total fats, 75±15 grams total carbohydrates, and 20±3 grams total protein.

In some embodiments, the multi-nutrient challenge beverage contains 60±6 grams total fats. In other embodiments, the multi-nutrient challenge beverage contains 50±6, 51±6, 52±6, 53±6, 54±6, 55±6, 56±6, 57±6, 58±6, or 59±6 grams totals fats. In some embodiments, the fat content of the multi-nutrient challenge beverage comprises from 10% to 20% of the total weight of the beverage. In other embodiments, the fat content of the multi-nutrient challenge beverage comprises 10%±2%, 11%±2%, 12%±2%, 13%±2%, 14%±2%, 15%±2%, 16%±2%, 17%±2%, 18%±2%, 19%±2%, or 20%±2% of the total weight of the beverage.

In some embodiments, the fat content of the beverage is primarily (e.g., at least 85%, 90%, 95%, or 99% of the fat content is derived) from an edible vegetable oil. Vegetable oils are primarily triglycerides extracted from plants. Non-limiting examples of vegetable oils include, but are not limited to, palm oil, coconut oil, corn oil, cottonseed oil, olive oil, peanut oil, rapeseed oil (e.g., canola oil), safflower oil, sesame oil, soybean oil, sunflower oil, and mixtures thereof. In one embodiment, the edible vegetable oil is palm oil.

In some embodiments, the fat content of the beverage is primarily (e.g., at least 85%, 90%, 95%, or 99% of the fat content is derived) from edible nut oil. Nut oils are primarily triglycerides extracted from nuts. Non-limiting examples of nut oils include, but are not limited to, almond oil, beech nut oil, brazil nut oil, cashew oil, hazelnut oil, macadamia nut oil, mongongo nut oil, pecan oil, pine nut oil, pistachio nut oil, walnut oil, pumpkin seed oil, and mixtures thereof.

In some embodiments, the multi-nutrient challenge beverage contains 80±15 grams total carbohydrates. In other embodiments, the multi-nutrient challenge beverage contains 60±5, 65±5, 70±5, 75±5, 80±5, 85±5, or 90±5, grams totals carbohydrates. In some embodiments, the carbohydrate content of the multi-nutrient challenge beverage comprises from 10% to 30% of the total weight of the beverage. In other embodiments, the carbohydrate content of the multi-nutrient challenge beverage comprises 20%±8%, 20%±6%, 20%±4%, 20%±2%, about 18%, about 19%, about 20%, about 21%, or about 22% of the total weight of the beverage. In other embodiments, the carbohydrate content of the multi-nutrient challenge beverage comprises 10%±2%, 11%±2%, 12%±2%, 13%±2%, 14%±2%, 15%±2%, 16%±2%, 17%±2%, 18%±2%, 19%±2%, 20%±2%, 21%±2%, 22%±2%, 23%±2%, 24%±2%, 25%±2%, 26%±2%, 27%±2%, 28%±2%, 29%±2%, or 30%±2% of the total weight of the beverage.

In some embodiments, the carbohydrate content of the beverage is primarily (e.g., at least 85%, 90%, 95%, or 99% of the carbohydrate content is derived) from monosaccharide sugar. Non-limiting examples of monosaccharide sugars include, but are not limited to, pentose sugars (e.g., arabinose, lyxose, ribose, xylose, ribulose, and xylulose), hexose sugars (e.g., allose, altroses, glucose (dextrose), mannose, gulose, Idose, galactose, talose, psicose, fructose, sorbose, and tagatose), heptose sugars (e.g., sedoheptulose, mannoheptulose, and L-glycero-D-manno-heptose). In one embodiments, the carbohydrate content of the beverage is primarily (e.g., at least 85%, 90%, 95%, or 99% of the carbohydrate content is derived) from glucose (dextrose).

In some embodiments, the multi-nutrient challenge beverage contains 20±10 grams total protein. In some embodiments, the multi-nutrient challenge beverage contains 10±5, 15±5, 20±5, 25±5, or 30±5 grams total protein. In other embodiments, the multi-nutrient challenge beverage contains 15±2, 16±2, 17±2, 18±2, 19±2, 20±2, 21±2, 22±2, 23±2, 24±2, or 25±2 grams total protein. In some embodiments, the protein content of the multi-nutrient challenge beverage comprises from 2.5% to 10% of the total weight of the beverage. In other embodiments, the protein content of the multi-nutrient challenge beverage comprises 2%±2%, 3%±2%, 4%±2%, 5%±2%, 6%±2%, 7%±2%, 8%±2%, 9%±2%, or 10%±2%, of the total weight of the beverage.

In some embodiments, the protein content of the beverage is primarily (e.g., at least 85%, 90%, 95%, or 99% of the protein content is derived) from protein isolated from an edible source, e.g., from soy, whey, or milk. In one embodiment, the protein content of the beverage is primarily (e.g., at least 85%, 90%, 95%, or 99% of the protein content is derived) from a milk protein isolate. Protein isolates, such as milk protein isolates, are used as emulsifiers and stabilizers in dairy products such as yogurt, ice cream and ice cream novelties, and liquid and powdered nutritional formulations. They are also used as a protein source in protein-enrichment applications such as powdered and ready-to-drink beverages for sports nutrition, adult nutrition, and weight management.

Other sources of edible protein include, without limitation, milk protein (e.g., lactose-free skim milk or milk protein isolate), soy milk, whey protein, caseinate, soy protein, egg whites, gelatins, collagen and combinations thereof.

In some embodiments, a multi-nutrient challenge beverage also contains one or more of a tastant (e.g., a flavoring agent), an emulsifier, a thickening agent, and a preservative.

Non-limiting examples of tastants (e.g., flavoring agents) include vanilla, cocoa, strawberry, and peanut butter.

Non-limiting examples of emulsifiers useful in a challenge beverage include canola lecithin, propane-1,2-diol alginate, konjac, polyoxyl 8 stearate, polyoxyethylene stearate, polysorbate 20, polysorbate 80, ammonium phosphatides, diphosphates, methyl cellulose, hydroxypropyl cellulose, hydroxypropyl methyl cellulose, ethyl methyl cellulose, carboxymethylcellulose, sodium carboxy methyl cellulose, sodium caseinate, magnesium stearate, sorbitan monostearate, sorbitan tristearate, sorbitan monolaurate, and sorbitan monopalmitate. In one embodiment, canola lecithin is used as an emulsifying agent in a challenge beverage described herein. Typically, the emulsifier is present in the challenge beverage at from about 0.01% to 2.0% by weight.

Non-limiting examples of thickening agents include gellan gum, alginic acid, sodium alginate, potassium alginate, ammonium alginate, calcium alginate, propane-1,2-diol alginate, agar, carrageenan, processed eucheuma seaweed, locust bean gum (carob gum), guar gum, tragacanth, acacia gum, xanthan gum, karaya gum, tara gum, pectin, xanthan, starches and modified starches, and mixtures thereof. In one embodiment, gellan gum is used as a thickening agent in a challenge beverage described herein.

Non-limiting examples of preservatives include citrates, e.g., sodium citrate and potassium citrate, benzoic acid, benzoates, e.g., sodium, calcium, and potassium benzoate, sorbates, e.g., sodium, calcium, and potassium sorbate, polyphosphates, e.g., sodium hexametaphosphate (SHMP), dimethyl dicarbonate, and mixtures thereof. Also of use are antioxidants, such as ascorbic acid, EDTA, BHA, BHT, TBHQ, EMIQ, dehydroacetic acid, ethoxyquin, heptylparaben, and combinations thereof. In one embodiment, sodium citrate is used as a preservative in a challenge beverage described herein.

In some embodiments, other ingredients are added to a challenge beverage composition including, but not limited to, one or more flavanols, aeidulants, coloring agents, minerals, vitamins, herbs, soluble fibers, non-caloric sweeteners, oils, carbonation components, and the like.

In some embodiments, a method for measuring the metabolic adaptability of a user is provided. The method includes obtaining data on a user's blood insulin levels, blood glucose levels, and blood triglyceride levels prior to consumption of a multi-nutrient challenge beverage, after a first period of time following consumption of the multi-nutrient challenge beverage, and after a second period of time following consumption of the multi-nutrient challenge beverage, and inputting the obtained data into a metabolic adaptability classifier. In some embodiments, the first period of time and second period of time following consumption of the multi-nutrient challenge beverage are each no longer than 120 minutes. In some embodiments, the challenge beverage is a challenge beverage described herein.

In some embodiments, the data obtained on the user's blood insulin levels, blood glucose levels, and blood triglyceride levels is derived from a dried blood sample collected by the user.

It will be understood that changes may be made to the composition of the challenge beverage or food as discussed above and that the above example is illustrative only.

Example 1—Challenge Beverage Validation Study

In order to validate the use of a multi-nutrient challenge beverage for determining metabolic adaptability of individuals, a trial was established using two challenge beverages containing 75 grams of carbohydrates, 50-60 grams of fats, and 20 grams of protein. Specifically, the study was designed to assess postprandial lipid and glycemic responses and gastrointestinal tolerance for the challenge beverages, assess the feasibility of assessing postprandial responses in dried capillary blood samples, and assess the feasibility of performing the test over a shorter time frame, e.g., within two hours.

Briefly, 18 subjects between the ages of 30-60, having a body mass index of from 18.5 to 30 kg/m' and normal GI function, were randomly administered either Challenge Beverage A (75 g carbohydrates, 60 g fat, 20 g protein, 940 kcal) or Challenge Beverage B (75 g carbohydrates, 50 g fat, 20 g protein, 860 kcal). The subjects fasted for 10 to 14 hours prior to administration and avoided vigorous physical activity (24 hours), alcohol consumption (24 hours), and tobacco use (1 hour) before administration. An intravenous catheter was inserted and venous and capillary blood samples were taken ten minutes prior to administration. After consumption of the assigned beverage, venous and capillary blood samples were collected at 30, 60, 90, 120, 180, and 240 minutes.

The collected samples were then analyzed as outlined in Table 2 to determine the following parameters:

Change in triglyceride concentrations from 0 to 120 min [the pre-consumption measurement (t=−10 min) will be counted as time 0 for the calculation];

Changes in glucose and insulin concentrations from 0 to 30, 120, 180, and 240 min [the pre-consumption measurement (t=−10 min) will be counted as time 0 for the calculation];

Changes in triglyceride concentration from 0 to 180 and 240 min [the pre-consumption measurement (t=−10 min) will be counted as time 0 for the calculation];

Triglyceride area under the curve (AUC) from 0 to 60, 90, 120, 180, and 240 min [the pre-consumption measurement (t=−10 min) will be counted as time 0 for the calculation];

Glucose and insulin AUC from 0 to 60, 90, 120, 180, and 240 min [the pre-consumption measurement (t=−10 min) will be counted as time 0 for the calculation];

Peak values for TG, glucose, and insulin; and

Composite score and individual ratings (nausea, GI rumblings, abdominal pain, bloating, flatulence, and diarrhea) using a GI tolerability questionnaire.

TABLE 2

Outline of the analyses performed on each collected blood sample.

| | Time (min) | | | | | | |
|---|---|---|---|---|---|---|---|
| | −10 | 30 | 60 | 90 | 120 | 180 | 240 |
| Glucose | X | X | X | X | X | X | X |
| Insulin | X | X | X | X | X | X | X |
| Triglycerides | X | X | X | X | X | X | X |
| Metabolic Profile | | | | | | | |
| TC* | X | | | | | | |
| HDL-C* | X | | | | | | |
| Hs-CRP | X | | | | | | |
| $HbA_{1C}$ | X | | | | | | |
| Fatty acids[1] | | | | X | | | |
| Vitamin A | | X | | | | | |
| Vitamin D | | X | | | | | |
| Vitamin E | | X | | | | | |
| Carotenoids[2] | | | | X | | | |

*Calculated LDL-C
[1]Fatty acids include: C16, C18, C18:1, C18:2, C18:3n6, C18:3n3, C20:3n6, C20:4n6, C20:5n3, and C22:6n3.
[2]Carotenoids include: alpha-carotene, beta-carotene, beta-crytoxanthin, lycopene, lutein, and zeaxanthin.

Figure 19:
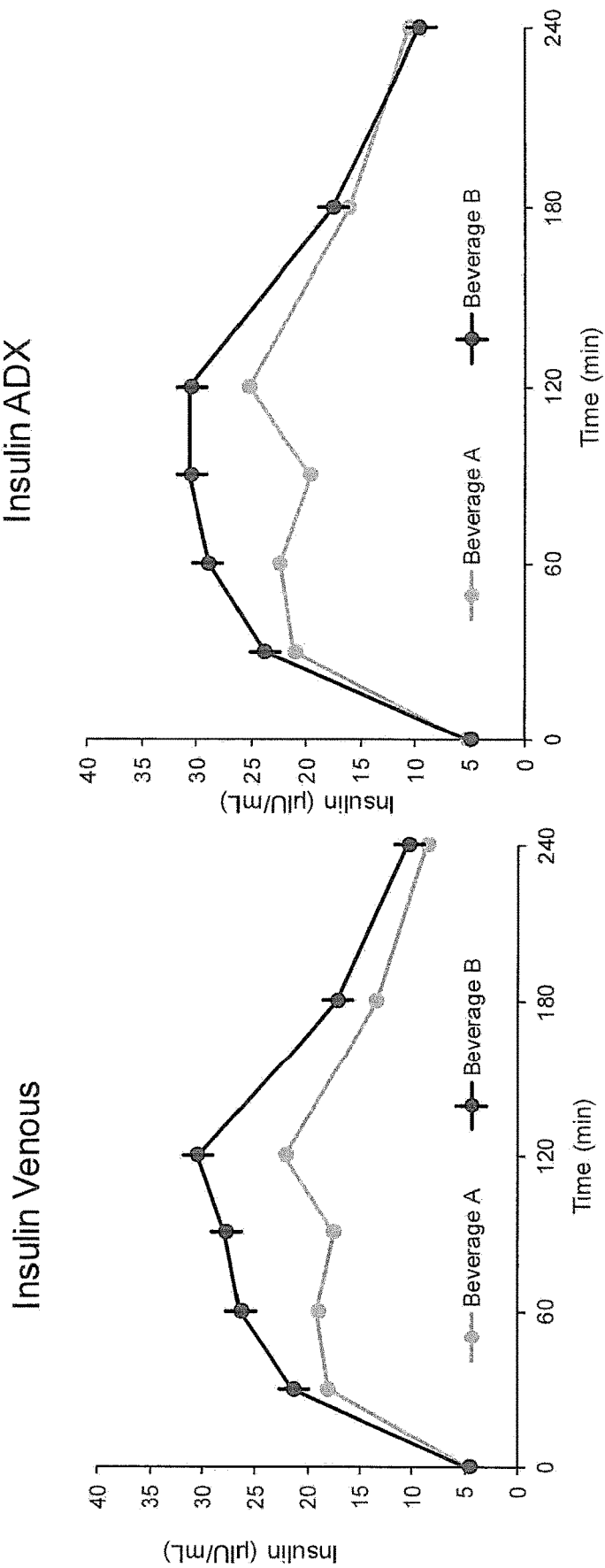
FIG. 19 depicts an illustrative classifier for determining dietary fat flexibility recommendations based on vitals, genotypic and/or phenotypic in accordance with some embodiments.
Figure 21:
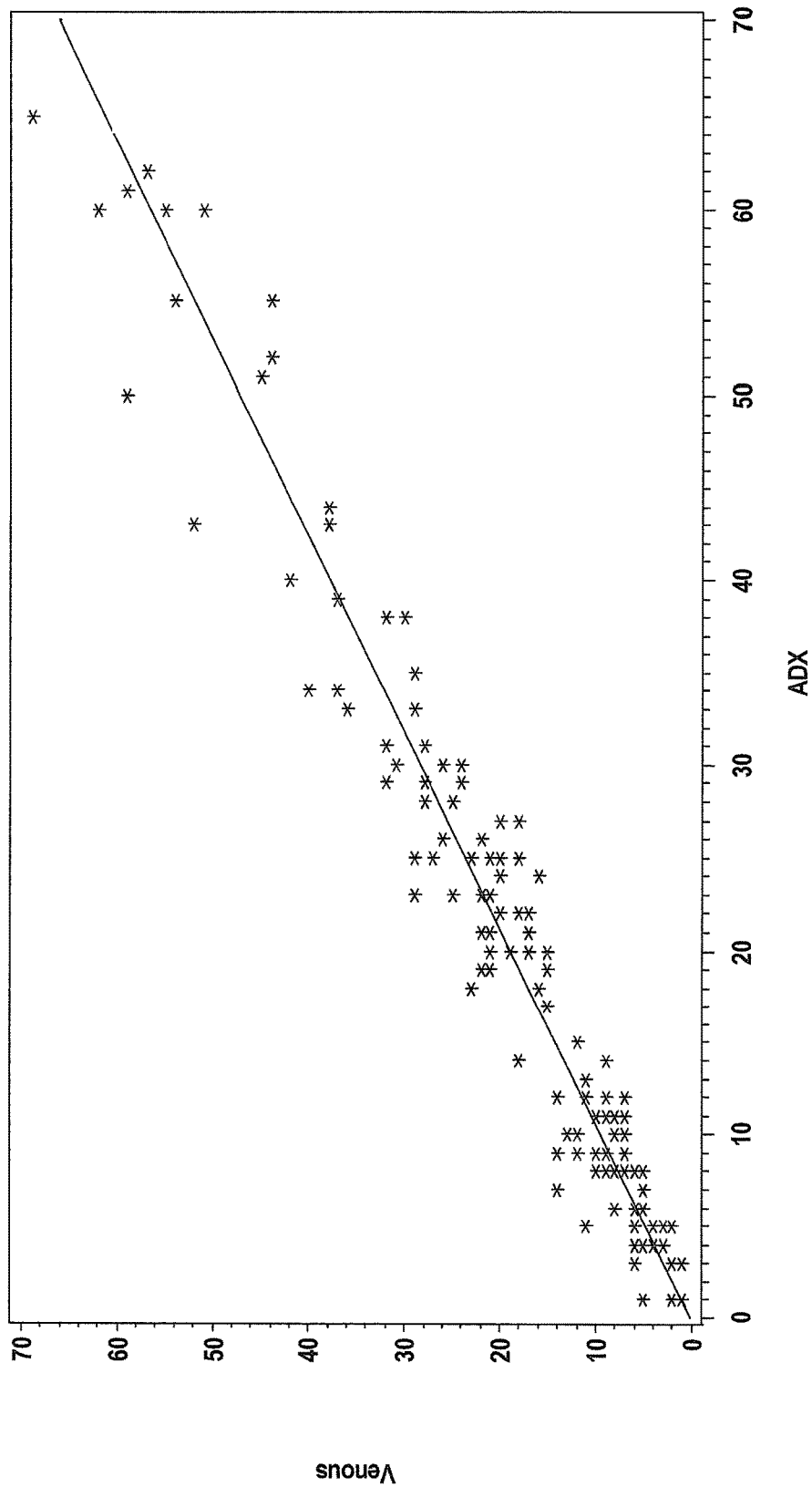
FIG. 21 illustrates a linear regression comparing insulin levels measured using capillary blood samples spotted on a substrate (insulin ADX) with venous blood collected in a catheter (insulin venous) before and after consuming a second multi-nutrient challenge beverage.

FIG. 19 shows plots of the average insulin levels detected in the venous catheter collected blood samples (Insulin Venous) and the dried capillary blood samples (Insulin ADX) for both challenge beverages. FIGS. 20 and 21 illustrate linear regressions comparing the insulin levels detected in the venous samples and the capillary samples for Challenge Beverage A (FIG. 20) and Challenge Beverage B (FIG. 21). As shown in the figures, there was a strong correlation between the insulin levels detected in the venous catheter collected blood sample and the dried capillary blood sample for both challenge beverages, evidencing that insulin sampling could be performed using dried blood spot (DBS) technology. Further, the measured insulin response following consumption of both challenge beverages peaked around 120 minutes, evidencing that longer time points were not necessary for sufficient measurement of an individual's insulin response to food.

Figure 22:
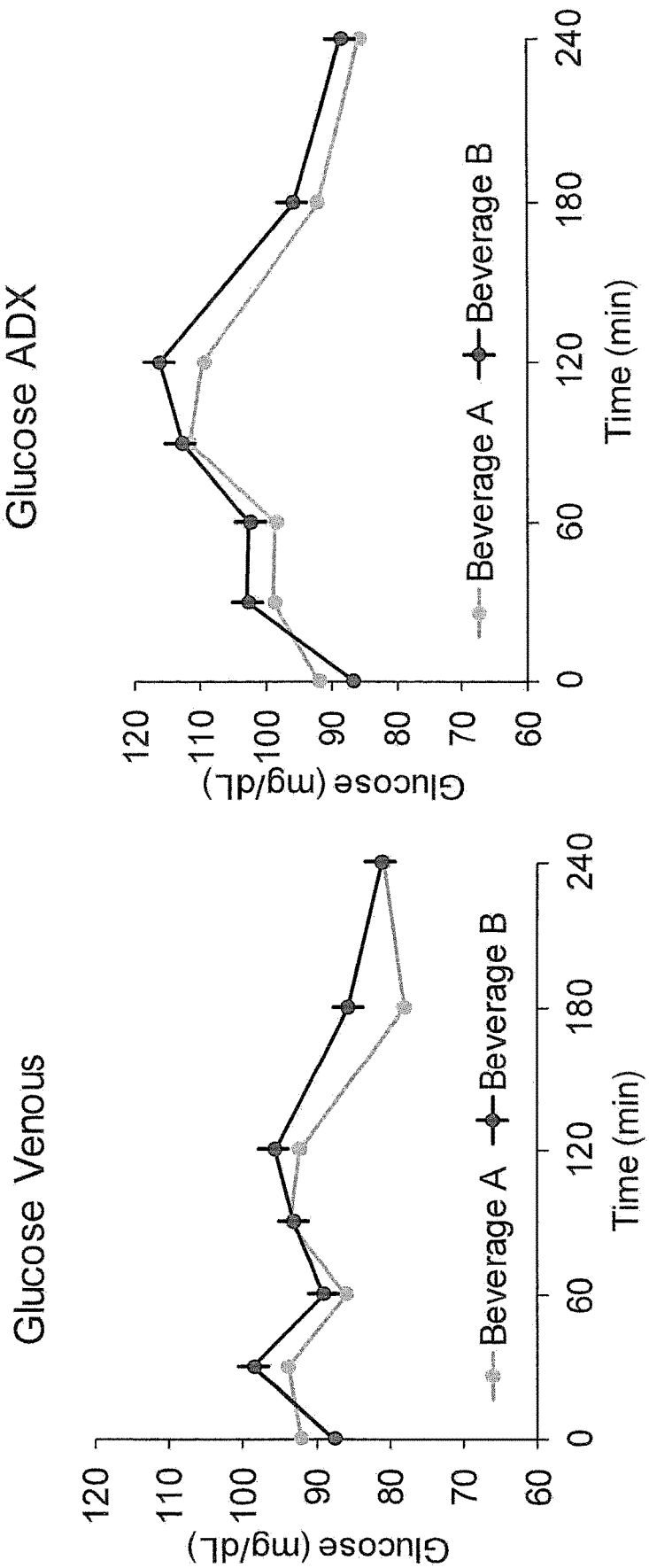
FIG. 22 illustrates glucose levels in subjects before and after consuming a multi-nutrient challenge beverage, as measured using capillary blood samples spotted on a substrate (insulin ADX) and venous blood collected in a catheter (insulin venous).
Figure 23:
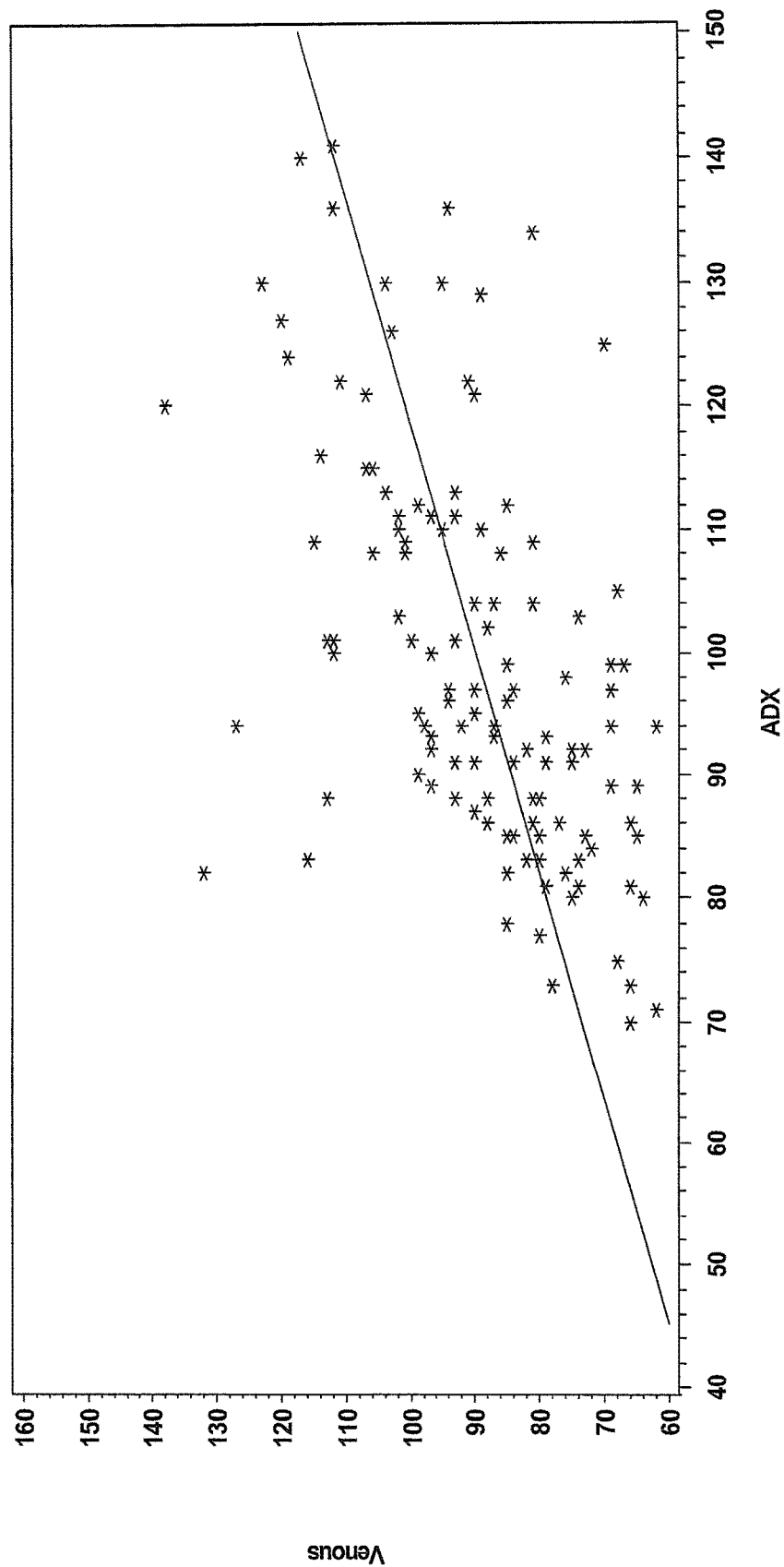
FIG. 23 illustrates a linear regression comparing glucose levels measured using capillary blood samples spotted on a substrate (insulin ADX) with venous blood collected in a catheter (insulin venous) before and after consuming a first multi-nutrient challenge beverage.
Figure 24:
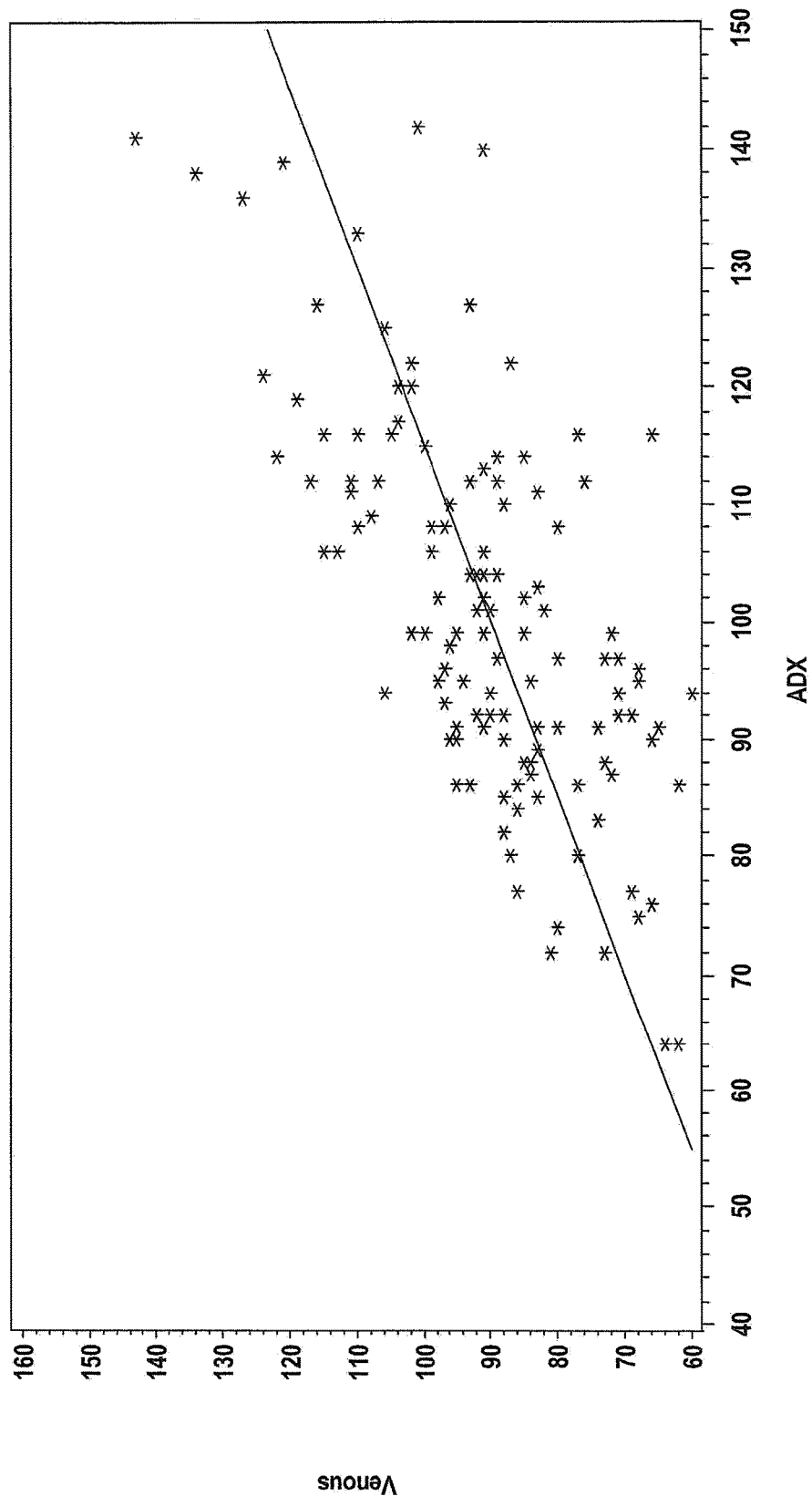
FIG. 24 illustrates a linear regression comparing glucose levels measured using capillary blood samples spotted on a substrate (insulin ADX) with venous blood collected in a catheter (insulin venous) before and after consuming a second multi-nutrient challenge beverage.

FIG. 22 shows plots of the average glucose levels detected in the venous catheter collected blood samples (Glucose Venous) and the dried capillary blood samples (Glucose ADX) for both challenge beverages. FIGS. 23 and 24 illustrate linear regressions comparing the glucose levels detected in the venous samples and the capillary samples for Challenge Beverage A (FIG. 23) and Challenge Beverage B (FIG. 24). As shown in the figures, there was a strong correlation between the glucose levels detected in the venous catheter collected blood sample and the dried capillary blood sample for both challenge beverages, evidencing that glucose sampling could be performed using dried blood spot (DBS) technology. Further, the measured glucose response following consumption of both challenge beverages peaked around 120 minutes, evidencing that longer time points were not necessary for sufficient measurement of an individual's glucose response to food.

Figure 25:
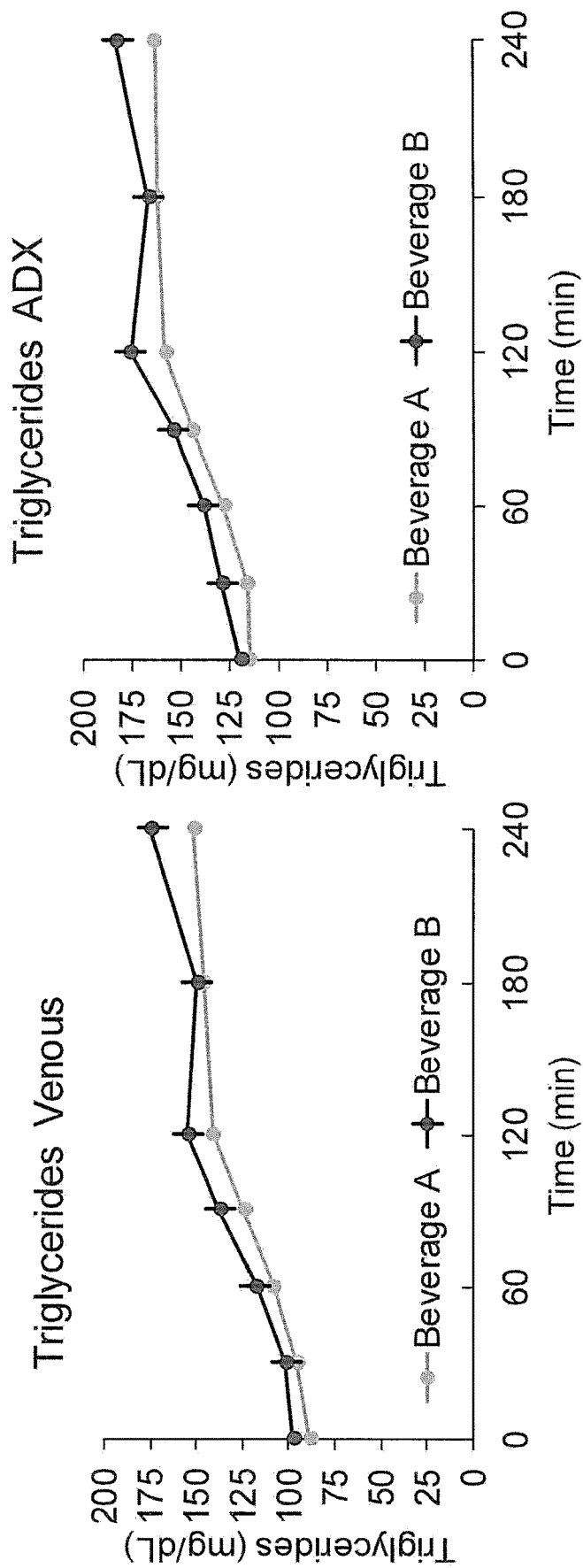
FIG. 25 illustrates triglyceride levels in subjects before and after consuming a multi-nutrient challenge beverage, as measured using capillary blood samples spotted on a substrate (insulin ADX) and venous blood collected in a catheter (insulin venous).
Figure 26:
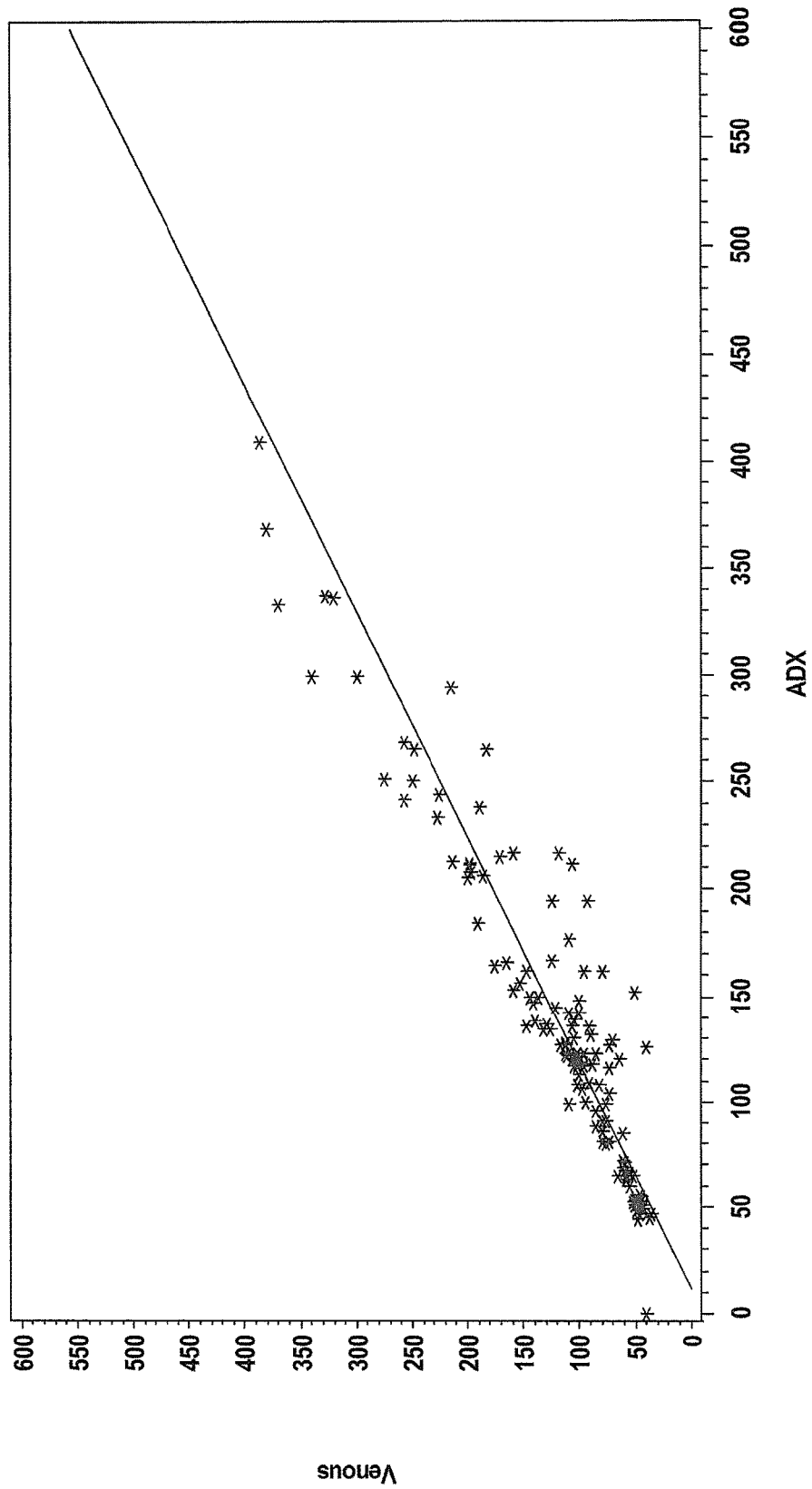
FIG. 26 illustrates a linear regression comparing triglyceride levels measured using capillary blood samples spotted on a substrate (insulin ADX) with venous blood collected in a catheter (insulin venous) before and after consuming a first multi-nutrient challenge beverage.
Figure 27:
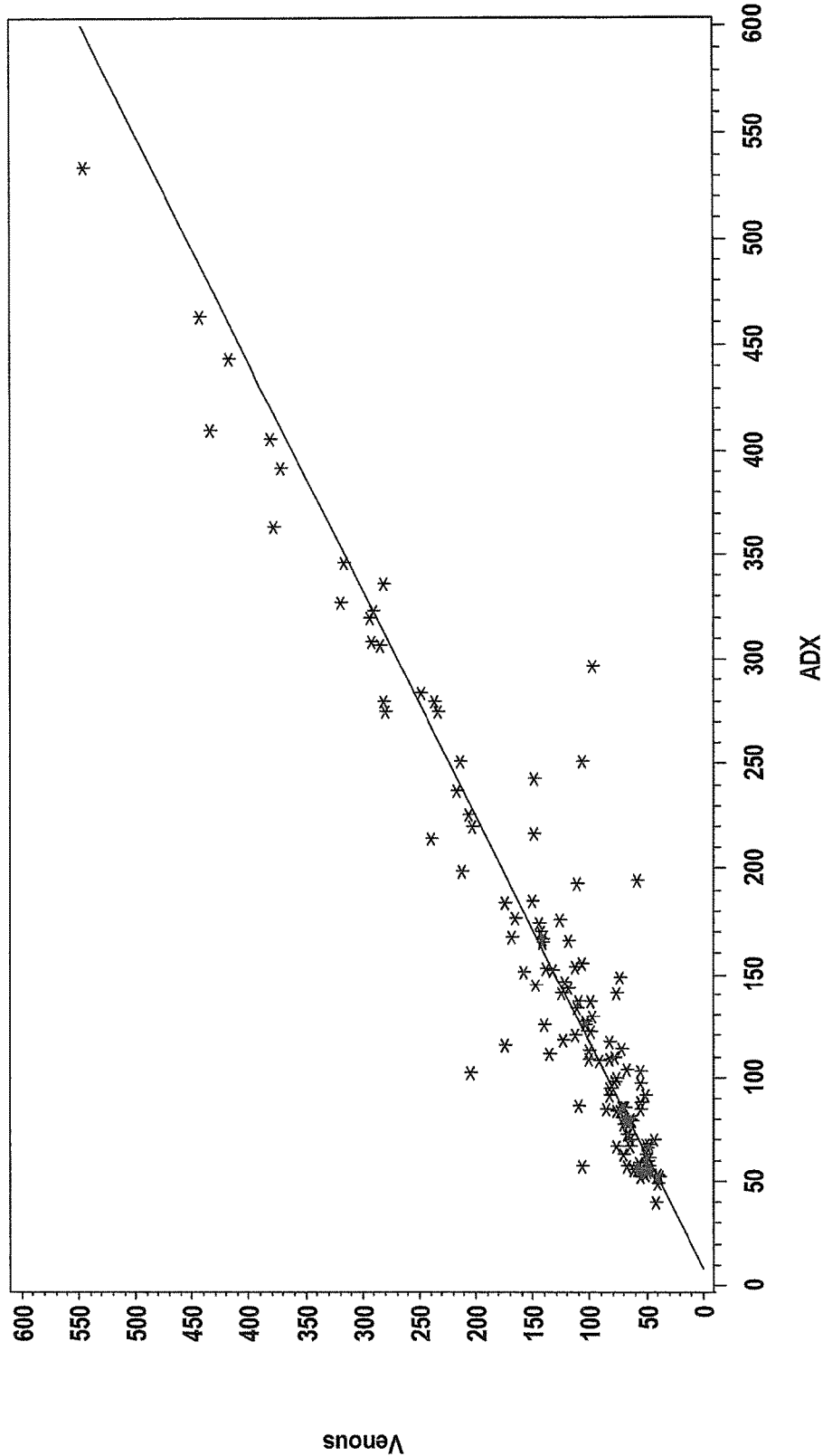
FIG. 27 illustrates a linear regression comparing triglyceride levels measured using capillary blood samples spotted on a substrate (insulin ADX) with venous blood collected in a catheter (insulin venous) before and after consuming a second multi-nutrient challenge beverage.
Figure 28B:
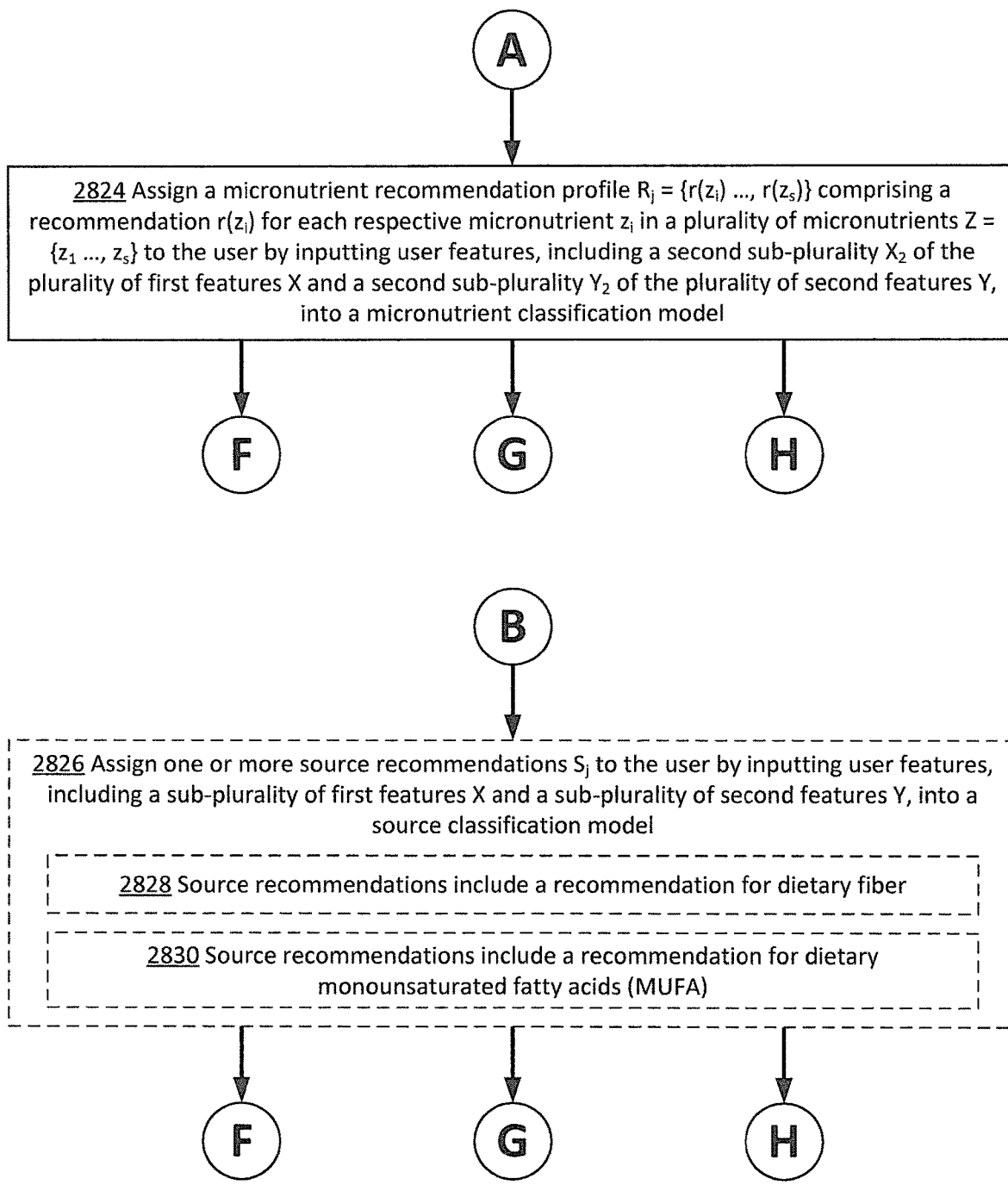
Figure 28C:
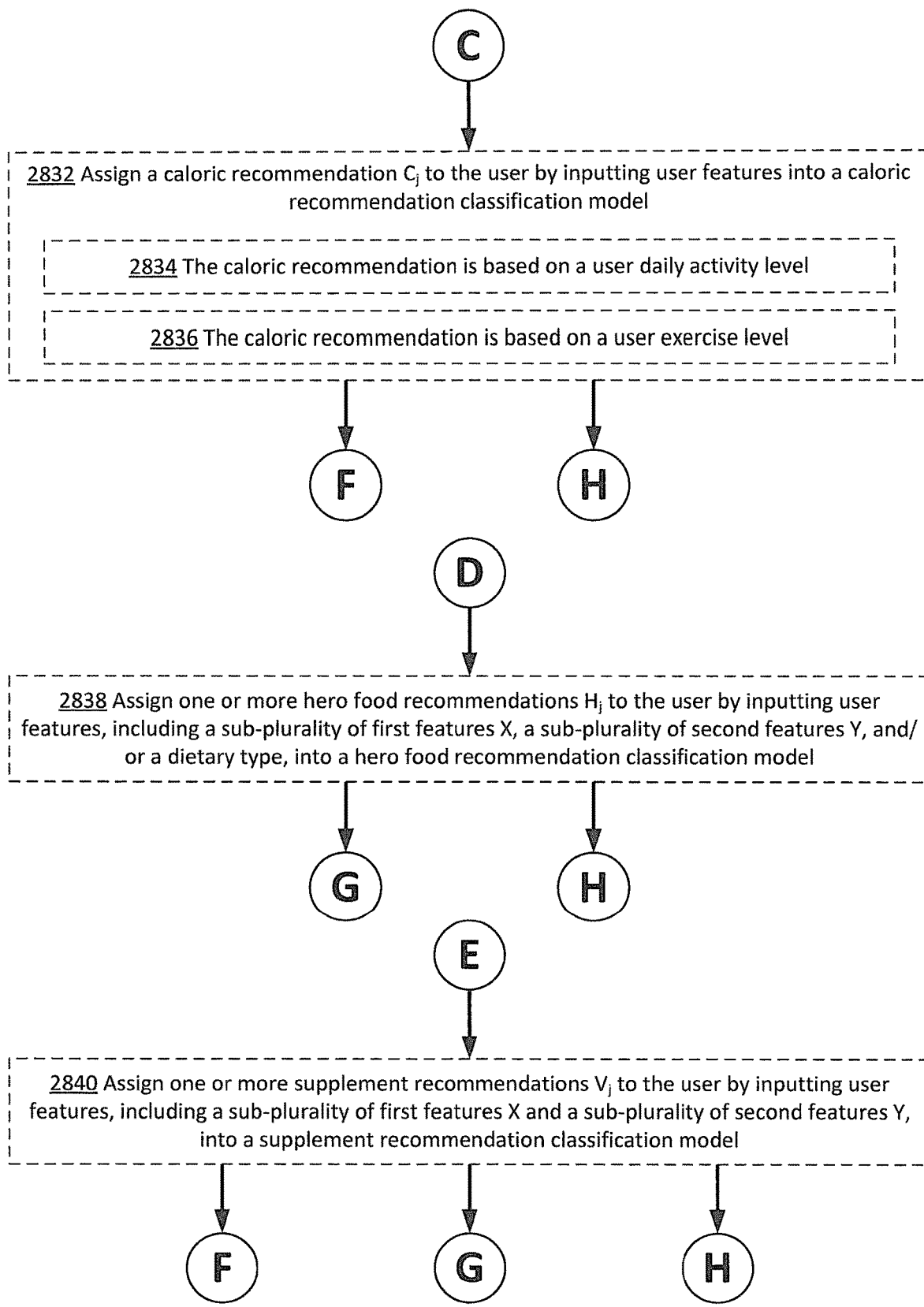
Figure 28F:
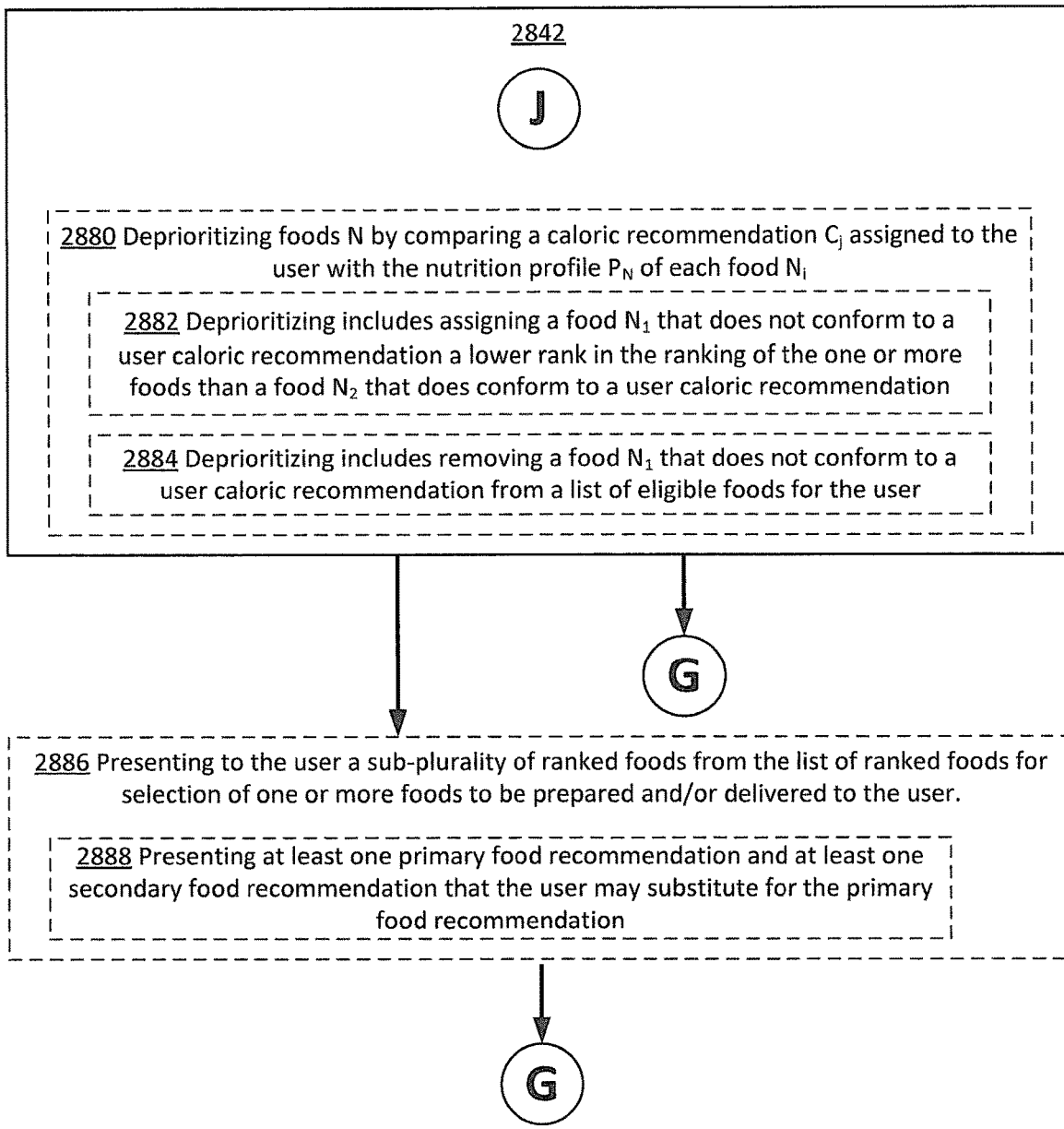
Figure 28G:
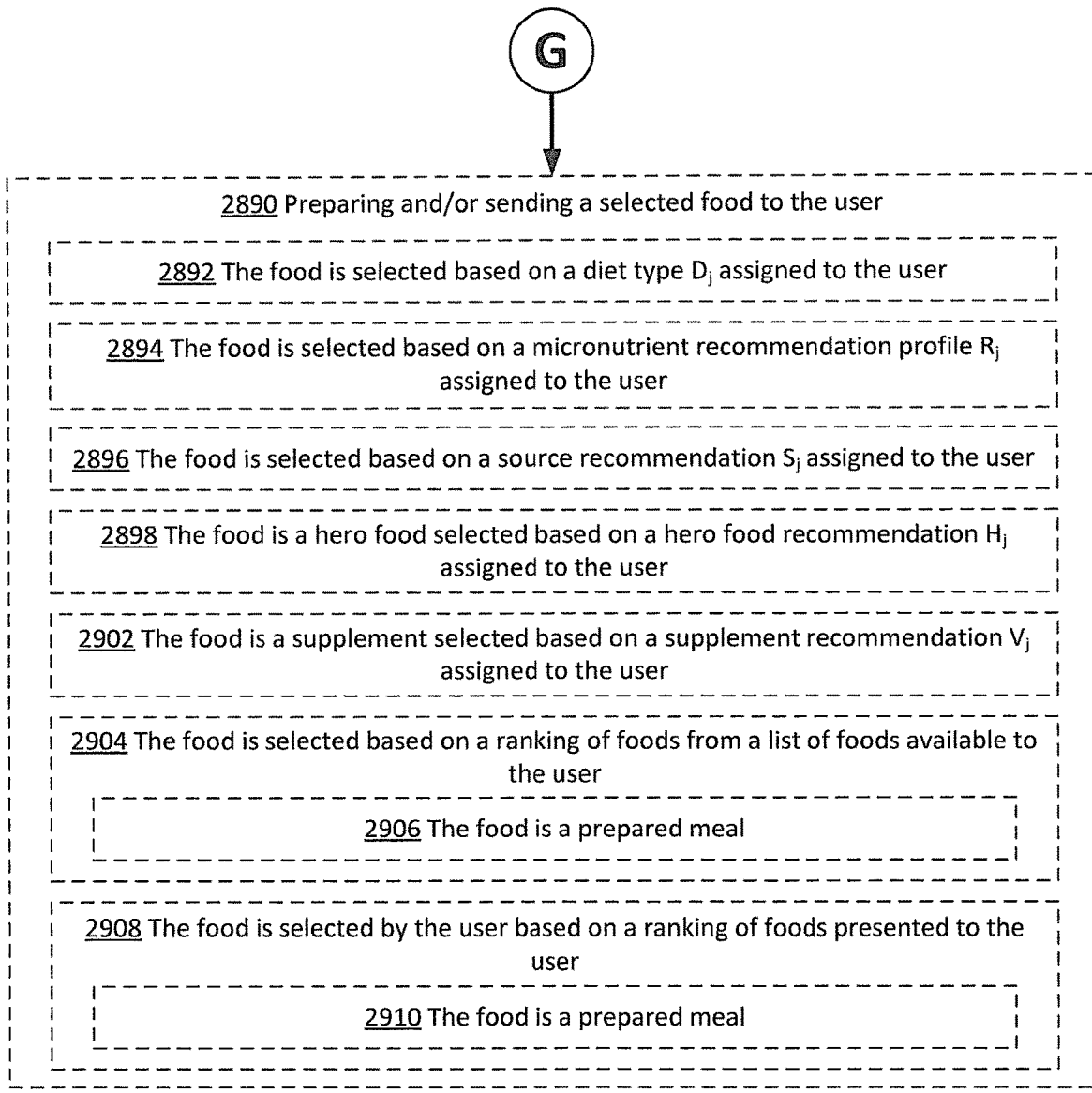

FIG. 25 shows plots of the average triglyceride levels detected in the venous catheter collected blood samples (Triglycerides Venous) and the dried capillary blood samples (Triglycerides ADX) for both challenge beverages. FIGS. 26 and 27 illustrate linear regressions comparing the triglyceride levels detected in the venous samples and the capillary samples for Challenge Beverage A (FIG. 26) and Challenge Beverage B (FIG. 27). As shown in the figures, there was a strong correlation between the triglyceride levels detected in the venous catheter collected blood sample and the dried capillary blood sample for both challenge beverages, evidencing that triglyceride sampling could be performed using dried blood spot (DBS) technology. Further, the measured triglyceride response following consumption of both challenge beverages first peaked around 120 minutes, evidencing that longer time points were not necessary for sufficient measurement of an individual's triglyceride response to food.

Advantageously, the use of dried capillary blood samples, as compared to venous liquid samples, requires minimal sample volumes, facilitates non-invasive sampling, does not require special training for collection, and provides stability of the sample at room temperature. All of the benefits facilitate home sample collection and delivery to a clinical laboratory by regular mail.

It will be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific implementations. However, the illustrative discussions above are not intended to be exhaustive or to limit the claims to the precise forms disclosed. Many modifications and variations are possible in view of the above teachings. The implementations were chosen and described in order to best explain principles of operation and practical applications, to thereby enable others skilled in the art.

What is claimed is:

1. A system for recommending foods to a user based on health data of the user, comprising:
   one or more processors;
   memory addressable by the one or more processors;
   an interface configured to receive data associated with a user, wherein the user's data comprises multiple fields and the fields comprise received values, wherein the received values comprise:
   A) genotypic data about the user comprising a plurality of first features $X=\{x_1 \ldots, x_m\}$, wherein each respective feature xi in the plurality of first features X is a status of a locus in a plurality of loci;
   B) phenotypic data about the user comprising a plurality of second features $Y=\{y_1 \ldots, y_n\}$, wherein each respective feature $y_i$ in the plurality of second features Y is a status of a phenotype in a plurality of phenotypes;
   C) a first sub-plurality $X_1$ of the plurality of first features X and a first sub-plurality $Y_1$ of the plurality of second features Y; and
   D) a second sub-plurality $X_2$ of the plurality of first features X and a second sub-plurality $Y_2$ of the plurality of second features Y;
   a database configured to store
   E) a plurality of foods $L=\{N_1 \ldots, N_t\}$, wherein each respective food $N_i$ in the plurality of foods has a corresponding nutrition profile $P_{Ni}=\{D_{ki}, P(z_{ki})\}$ comprising an assigned diet type $D_k$ in a plurality of diet types $D=\{D_1 \ldots, D_q\}$ and an assigned micronutrient profile $P(z_k)=\{v(z_1) \ldots, v(z_s)\}$, wherein the micronutrient profile $P(z_k)$ includes a respective value $v(z_i)$ for each micronutrient $z_i$ in the plurality of micronutrients Z;
   the memory storing instructions as one or more programs that, when executed by the one or more processors, cause the system to:
   retrieve, from the memory, the received values of the user's data;
   iteratively compare, via the one or more processors executing a machine-learning model trained on users' genotypic data and phenotypic data to predict three or more scalar values representing macronutrient recommendations, the first sub-plurality $X_1$ and the first sub-plurality $Y_1$ to ranges associated with categories, with each category having one or more thresholds separating ranges, wherein the iterative comparisons adjust a comparison result across the iterative comparisons;
   convert, based on the three or more determined scalar values and via the one or more processors, the three or more determined scalar values from scalars to a multi-dimensional vector representation of the three or more determined scalar values;
   compare, based on the conversion and via the one or more processors, the multi-dimensional vector with possible macronutrient recommendations where the possible macronutrient recommendations exist in a space defined by possible vectors;
   determine, based on a matching of the multi-dimensional vector with a recommendation of the possible macronutrient recommendations and via the one or more processors, a matching macronutrient recommendation covering vector space identified by the multi-dimensional vector, the matching macronutrient recommendation comprising a respective diet type $D_j$ in the plurality of diet types D;
   determine, based on the second sub-plurality $X_2$ of the plurality of first features X and the second sub-plurality $Y_2$ of the plurality of second features Y, a micronutrient recommendation profile $R_j=\{r(z_i) \ldots, r(z_s)\}$ comprising a recommendation $r(z_i)$ for each respective micronutrient $z_i$ in a plurality of micronutrients $Z=\{z_1 \ldots, z_s\}$;
   rank, based on comparisons, to the nutrition profiles $P_N$ of foods N in the plurality of foods L, of the diet type $D_j$ assigned to the user, and of the micronutrient recommendation profile $R_j$ assigned to the user, a list of one or more foods in a plurality of foods $L=\{N_1 \ldots, N_t\}$, wherein each respective food $N_i$ in the plurality of foods has a corresponding nutrition profile $P_{Ni}=\{D_{ki}, P(z_{ki})\}$ comprising an assigned diet type $D_k$ in the plurality of diet types D and an assigned micronutrient profile $P(z_k)=\{v(z_i) \ldots, v(z_s)\}$, wherein the micronutrient profile $P(z_k)$ includes a respective value $v(z_i)$ for each micronutrient $z_i$ in the plurality of micronutrients Z; and
   based on the determination of the matching of the multi-dimensional vector with the macronutrient recommendation, the micronutrient recommendation profile, and the ranking of the one or more foods, output the matching macronutrient and/or micronutrient recommendation and the ranked list of one or more foods.

2. The system according to claim 1, wherein the instructions to determine the diet type $D_j$ further cause the system to:
   receive a third sub-plurality $X_3$ of the plurality of first features X and a third sub-plurality $Y_3$ of the plurality of second features Y;
   determine, based on the received third sub-plurality $X_3$ and the third sub-plurality $Y_3$ and via a classification model configured to identify a fat recommendation, a macronutrient fat intake recommendation $F_j$;

receive a fourth sub-plurality $X_4$ of the plurality of first features X and a fourth sub-plurality $Y_4$ of the plurality of second features Y;

determine, based on the received fourth sub-plurality $X_4$ and the fourth sub-plurality $Y_4$ and via a classification model configured to identify a carbohydrate recommendation, a macronutrient carbohydrate intake recommendation $C_j$;

receive a fifth sub-plurality $X_5$ of the plurality of first features X and a fifth sub-plurality $Y_5$ of the plurality of second features Y;

determine, based on the received fifth sub-plurality $X_5$ and the fifth sub-plurality $Y_5$ and via a classification model configured to identify a protein recommendation, a macronutrient protein intake recommendation $P_j$; and compare the assigned macronutrient fat intake recommendation $F_j$, macronutrient carbohydrate intake recommendation $C_j$, and macronutrient protein intake recommendation $P_j$ to the plurality of diet types $D=\{D_1 \ldots, D_q\}$; and assign a selected one of the diet types D.

3. The system according to claim 1, wherein the instructions to rank the list of the one or more foods in the plurality of foods further includes considering one or more of:
a fiber source recommendation,
(ii) a monounsaturated fatty acid source recommendation;
(iii) a caloric recommendation;
(iv) a food preference;
(v) a food allergy;
(vi) an anthropometric feature;
(vii) a goal;
(viii) a dietary pattern; or
(ix) an activity pattern.

4. The system according to claim 1, wherein the plurality of foods is selected from a larger plurality of foods using a machine-learning model based on one or more users' preferences for foods previous presented to them for selection.

5. The system according to claim 1, wherein the instructions to rank the list of the one or more foods is performed using a machine-learning model based on one or more users' preferences for foods previous presented to them for selection.

6. The system according to claim 1, wherein the plurality of foods is a plurality of meals.

7. The system according to claim 1,
wherein the one or more programs further comprise instructions that cause the system to obtain a user food preference, and
wherein the instructions for ranking the one or more foods further cause the system to
deprioritize a food in the plurality of foods L, that does not conform to the user food preference.

8. The system according to claim 1,
wherein the one or more programs further comprise instructions that cause the system to assign a caloric recommendation $C_j$ to the user based on at least one of a user daily activity level and a user exercise level, and
wherein the instructions to rank the list of the one or more foods further cause the system to deprioritize a food in the plurality of foods L, that does not conform to the caloric recommendation $C_j$.

9. The system according to claim 1, wherein the one or more programs further comprise instructions that cause the system to:

display, to the user, a sub-plurality of the one or more ranked foods for selection of a food to be prepared and/or delivered to the user.

10. The system according to claim 1, wherein the instructions to compare the diet type $D_j$ to the nutrition profiles $P_N$ of foods N in the plurality of foods L and to compare micronutrient recommendation profile to the nutrition profiles $P_N$ of foods N in the plurality of foods L include instructions to:

rank foods N assigned to the same diet type $D_k$ as the diet type assigned to the user $D_j$ higher than foods N assigned to a different diet type in the plurality of diet types D, and rank, between foods N assigned to the same diet type $D_i$, foods N having a micronutrient profile $P(z_{k1})$ that more closely match the user's micronutrient recommendation profile higher than foods N having a micronutrient profile $P(z_{k2})$ that less closely match the user's micronutrient recommendation profile $R_j$.

11. The system according to claim 1, further comprising:
a user health database associated with or accessible by the system, for storing information about the user's phenotypical data and the user's health data, genotypic data, goals and/or food preference;
a meal and recipe database associated with or accessible by the system, for storing information on meals, recipes, supplements and/or hero foods that are available for recommendation to the user;
a meal processing engine for receiving data associated with foods, meals and/or recipes in terms of number of calories, macronutrients and/or micronutrients, for converting the data into a format usable by the system and storing the data in the meal and recipe database, a decision tree engine, for producing macronutrient and micronutrient classifications for the user based on the user's health data;
a user specific filtering engine, for filtering meal data based on the user's macronutrient classifications, diet type, the user's goals and/or food preferences; and
a meal ranker engine, food selection classifier or food recommendation classifier for receiving available meals, the user's macronutrient classifications and/or diet type, the user's micronutrient classifications, and information from the user health database and meal and recipe database.

12. The system according to claim 1,
wherein the phenotypic data includes metabolic adaptability information determined through analysis of the user's blood following consumption of a multi-nutrient challenge beverage, and
wherein the multi-nutrient challenge beverage includes a) from 44 to 57 grams total fats; b) 75±15 grams total carbohydrates; and c) 20±3 grams total protein.

13. The system of claim 1,
wherein the machine-learning model comprises one or more of linear discriminant analysis, logistic discriminate analysis, logistic regression analysis, nearest neighbor classifier analysis, principal component analysis, quadratic discriminant analysis, regression classifier analysis, vector machine analysis, classification and regression tree analysis, multiple additive regression tree analysis, prediction analysis for microarrays, random forest analysis, generalized additive analysis, neural network analysis, or non-parametric algorithm analysis.

14. A computer-implemented method for recommending foods to a user, comprising:

receiving, via an interface data associated with a user, wherein the user's data comprises multiple fields and the fields comprise received values, wherein the received values comprise:
- A) genotypic data about the user comprising a plurality of first features $X=\{x_1 \ldots, x_m\}$, wherein each respective feature xi in the plurality of first features X is a status of a locus in a plurality of loci;
- B) phenotypic data about the user comprising a plurality of second features $Y=\{y_1 \ldots, y_n\}$, wherein each respective feature $y_i$ in the plurality of second features Y is a status of a phenotype in a plurality of phenotypes, the phenotypic data comprising metabolic adaptability information of a user;
- C) a first sub-plurality $X_1$ of the plurality of first features X and a first sub-plurality $Y_1$ of the plurality of second features Y; and
- D) a second sub-plurality $X_2$ of the plurality of first features X and a second sub-plurality $Y_2$ of the plurality of second features Y;

storing, in a database, information comprising
- E) a plurality of foods $L=\{N_1 \ldots, N_t\}$, wherein each respective food $N_i$ in the plurality of foods has a corresponding nutrition profile $P_{Ni}=\{D_{ki}, P(z_{ki})\}$ comprising an assigned diet type $D_k$ in a plurality of diet types $D=\{D_1 \ldots, D_q\}$ and an assigned micronutrient profile $P(z_k)=\{v(z_1) \ldots, v(z_s)\}$, wherein the micronutrient profile $P(z_k)$ includes a respective value $v(z_i)$ for each micronutrient $z_i$ in the plurality of micronutrients Z;

iteratively comparing, via the one or more processors executing a machine-learning model trained on users' genotypic data and phenotypic data to predict three or more scalar values representing macronutrient recommendations, the first sub-plurality $X_1$ and the first sub-plurality $Y_1$ to ranges associated with categories, with each category having one or more thresholds separating ranges, wherein iteratively comparing adjusts a comparison result across the iterative comparisons;

converting, based on the three or more determined scalar values and via the one or more processors, the three or more determined scalar values from scalars to a multi-dimensional vector representation of the three or more determined scalar values;

comparing, based on the conversion and via the one or more processors, the multi-dimensional vector with possible macronutrient recommendations where the possible macronutrient recommendations exist in a space defined by possible vectors;

determining, based on a matching of the multi-dimensional vector with a recommendation of the possible macronutrient recommendations and via the one or more processors, a matching macronutrient recommendation covering vector space identified by the multi-dimensional vector, the matching macronutrient recommendation comprising a respective diet type $D_j$ in the plurality of diet types D;

determining, based on the second sub-plurality $X_2$ of the plurality of first features X and the second sub-plurality $Y_2$ of the plurality of second features Y, a micronutrient recommendation profile $R_j=\{r(z_i) \ldots, r(z_s)\}$ comprising a recommendation $r(z_i)$ for each respective micronutrient $z_i$ in a plurality of micronutrients $Z=\{z_1 \ldots, z_s\}$;

ranking, based on comparisons, to the nutrition profiles $P_N$ of foods N in the plurality of foods L, of the diet type $D_j$, assigned to the user, and of the micronutrient recommendation profile $R_j$, assigned to the user, a list of one or more foods in a plurality of foods $L=\{N_1 \ldots, N_t\}$, wherein each respective food $N_i$ in the plurality of foods has a corresponding nutrition profile $P_{Ni}=\{D_{ki}, P(z_{ki})\}$ comprising an assigned diet type $D_k$ in the plurality of diet types D and an assigned micronutrient profile $P(z_k)=\{v(z_1) \ldots, v(z_s)\}$, wherein the micronutrient profile $P(z_k)$ includes a respective value $v(z_i)$ for each micronutrient $z_i$ in the plurality of micronutrients Z; and outputting, based on the matched multi-dimensional vector with the macronutrient recommendation, the micronutrient recommendation profile, and the ranking of the one or more foods, the matching macronutrient and/or micronutrient recommendation and the ranked list of one or more foods.

15. The computer-implemented method according to claim 14, wherein assigning respective diet type further comprises:
receiving a third sub-plurality $X_3$ of the plurality of first features X and a third sub-plurality $Y_3$ of the plurality of second features Y;

determining, based on the received third sub-plurality $X_3$ and the third sub-plurality $Y_3$ and via a classification model configured to identify a fat recommendation, a macronutrient fat intake recommendation $F_j$;

receiving a fourth sub-plurality $X_4$ of the plurality of first features X and a fourth sub-plurality $Y_4$ of the plurality of second features Y;

determining, based on the received fourth sub-plurality $X_4$ and the fourth sub-plurality $Y_4$ and via a classification model configured to identify a carbohydrate recommendation, a macronutrient carbohydrate intake recommendation $C_j$;

receiving a fifth sub-plurality $X_5$ of the plurality of first features X and a fifth sub-plurality $Y_5$ of the plurality of second features Y;

determining, based on the received fifth sub-plurality $X_5$ and the fifth sub-plurality $Y_5$ and via a classification model configured to identify a protein recommendation, a macronutrient protein intake recommendation $P_j$; and comparing the assigned macronutrient fat intake recommendation $F_j$, macronutrient carbohydrate intake recommendation $C_j$, and macronutrient protein intake recommendation $P_j$ to the plurality of diet types $D=\{D_1 \ldots, D_q\}$; and assigning a selected one of the diet types D.

16. The computer-implemented method according to claim 14, wherein ranking one or more foods in a plurality of foods further includes considering one or more of:
a fiber source recommendation,
(ii) a monounsaturated fatty acid source recommendation;
(iii) a caloric recommendation;
(iv) a food preference;
(v) a food allergy;
(vi) an anthropometric feature;
(vii) a goal;
(viii) a dietary pattern; or
(ix) an activity pattern.

17. The computer-implemented method according to claim 14, wherein the plurality of foods is selected from a larger plurality of foods using a machine-learning model based on one or more users' preferences for foods previous presented to them for selection.

18. The computer-implemented method according to claim 14, wherein the ranking one or more foods is performed using a machine-learning model based on one or more users' preferences for foods previous presented to them for selection.

19. The computer-implemented method according to claim 14, wherein the plurality of foods is a plurality of meals.

20. The computer-implemented method according to claim 14,
wherein the method further comprises obtaining a user food preference, and
wherein the ranking of the one or more foods includes deprioritizing a food in the plurality of foods L, that does not conform to the user food preference.

21. The computer-implemented method according to claim 14,
wherein the method further comprises assigning a caloric recommendation $C_j$ to the user based on at least one of a user daily activity level and a user exercise level, and
wherein the ranking of the one or more foods includes deprioritizing a food in the plurality of foods L, that does not conform to the caloric recommendation $C_j$.

22. The computer-implemented method according to claim 14, further comprising:
presenting, to the user, a sub-plurality of the one or more ranked foods for selection of a food to be prepared and/or delivered to the user.

23. The computer-implemented method according to claim 14, wherein comparing each of the diet type $D_j$ and micronutrient recommendation profile $R_j$ to the nutrition profiles $P_N$ of foods N in the plurality of foods L includes:
ranking foods N assigned to the same diet type $D_k$ as the diet type assigned to the user $D_j$ higher than foods N assigned to a different diet type in the plurality of diet types D, and ranking, between foods N assigned to the same diet type $D_i$, foods N having a micronutrient profile $P(z_{k1})$ that more closely match the user's micronutrient recommendation profile higher than foods N having a micronutrient profile $P(z_{k2})$ that less closely match the user's micronutrient recommendation profile $R_j$.

24. The computer-implemented method according to claim 14,
wherein the metabolic adaptability of a user is measured by obtaining data on, of the user, blood insulin levels, blood glucose levels, and blood triglyceride levels prior to consumption of a multi-nutrient challenge beverage, after a first period of time following consumption of the multi-nutrient challenge beverage, and after a second period of time following consumption of the multi-nutrient challenge beverage, and
wherein the method further comprises inputting the obtained data into a metabolic adaptability classifier.

25. The computer-implemented method according to claim 24,
wherein the first period of time and second period of time following consumption of the multi-nutrient challenge beverage are each no longer than 120 minutes.

26. The computer-implemented method according to claim 24, wherein the fat content of the multi-nutrient challenge beverage comprises from 10% to 20% of a total weight of the multi-nutrient challenge beverage, wherein a carbohydrate content of the multi-nutrient challenge beverage comprises from 10% to 30% of the total weight of the multi-nutrient challenge beverage, and wherein a protein content of the multi-nutrient challenge beverage comprises from 2.5% to 10% of the total weight of the multi-nutrient challenge beverage.

27. The computer implemented method according to claim 24, wherein the fat content of the multi-nutrient challenge beverage is primarily from palm oil.

28. The computer implemented method according to claim 24, wherein the carbohydrate content of the multi-nutrient challenge beverage is primarily from monosaccharide sugar, preferably dextrose.

29. The computer implemented method according to claim 24, wherein the protein content of the multi-nutrient challenge beverage is primarily from a milk protein isolate.

30. The computer implemented method according to claim 24, wherein the multi-nutrient challenge beverage further includes one or more of a tastant, an emulsifier, a thickening agent, and a preservative.

31. The computer implemented method according to claim 14, wherein the metabolic adaptability of the user is determined one or more times following adaption of a particular diet type to track changes in the user's metabolic adaptability following implementation of a particular diet.

32. The computer implemented method according to claim 14, further comprising:
measuring the metabolic adaptability information of the user through analysis of the user's blood following consumption of a multi-nutrient challenge beverage, wherein the multi-nutrient challenge beverage includes
a) from 44 to 57 grams total fats;
b) 75±15 grams total carbohydrates; and c) 20±3 grams total protein.

33. The computer implemented method according to claim 32,
wherein the metabolic adaptability information comprises the user's blood insulin level, blood glucose level, and/or blood triglyceride level, and
wherein said measuring the metabolic adaptability information comprises measuring prior to consumption of the multi-nutrient challenge beverage, after a first period of time following consumption of the multi-nutrient challenge beverage, and after a second period of time following consumption of the multi-nutrient challenge beverage.

34. The computer implemented method of claim 14, wherein the machine-learning model comprises one or more of linear discriminant analysis, logistic discriminate analysis, logistic regression analysis, nearest neighbor classifier analysis, principal component analysis, quadratic discriminant analysis, regression classifier analysis, vector machine analysis, classification and regression tree analysis, multiple additive regression tree analysis, prediction analysis for microarrays, random forest analysis, generalized additive analysis, neural network analysis, or non-parametric algorithm analysis.

35. A system comprising:
an interface configured to receive data associated with a user, wherein the user's data comprises multiple fields and each field comprises a received value, wherein the received values comprise phenotypical data, wherein the phenotypical data includes metabolic adaptability information determined through analysis of blood of the user following consumption of a multi-nutrient challenge beverage, and wherein the multi-nutrient challenge beverage includes a) from 44 to 57 grams total fats;
b) 75±15 grams total carbohydrates; and
c) 20±3 grams total protein;
one or more processors;
memory storing instructions that, when executed by the one or more processors, cause the system to:
retrieve, from the memory, the received values for the user's data;
iteratively compare, via the one or more processors executing a machine-learning model trained on users' phenotypic data to predict three or more scalar values representing macronutrient recommendations, the received values to ranges associated with categories, with each category having one or more thresholds separating ranges, wherein the iterative comparisons adjust a comparison result across the iterative comparisons;
convert, based on the three or more determined scalar values and via the one or more processors, the three or more determined scalar values from scalars to a multi-dimensional vector representation of the three or more determined scalar values;
compare, based on the conversion and via the one or more processors, the multi-dimensional vector with possible macronutrient and/or micronutrient recommendations where the possible recommendations exist in a space defined by possible vectors;
determine, based on a matching of the multi-dimensional vector with a recommendation of the possible macronutrient and/or micronutrient recommendations and via the one or more processors, a matching macronutrient and/or micronutrient recommendation covering vector space identified by the multi-dimensional vector; and
output, based on the determination of the matching of the multi-dimensional vector with the recommendation, the matching macronutrient and/or micronutrient recommendation.

36. The system of claim 35,
wherein the retrieved values further comprise genotypic data of the user,
wherein the genotypic data comprising a plurality of first features $X=\{x_1 \ldots, x_m\}$, wherein each respective feature xi in the plurality of first features X is a status of a locus in a plurality of loci,
wherein the phenotypic data comprising a plurality of second features $Y=\{y_1 \ldots, y_n\}$, wherein each respective feature $y_i$ in the plurality of second features Y is a status of a phenotype in a plurality of phenotypes, and
wherein the matching recommendation is a diet type $D_j$ in a plurality of diet types $D=\{D_i \ldots, D_q\}$, where the plurality of diet types are defined in the vector space.

37. The system of claim 35, wherein the instructions further cause the system to:
retrieve, from the memory, second values of the user's data;
compare the second values to additional ranges defined by one or more thresholds; and
determine, based on the comparison of the second values to the additional ranges, micronutrient recommendations,
wherein the matching recommendation is a diet type $D_j$ in a plurality of diet types $D=\{D_1 \ldots, D_q\}$, where the plurality of diet types are defined in the vector space, and
wherein the micronutrient recommendations comprise a micronutrient recommendation profile $R_j=\{r(z_i) \ldots, r(z_s)\}$ comprising a recommendation $r(z_i)$ for each respective micronutrient $z_i$ in a plurality of micronutrients $Z=\{z_1 \ldots, z_s\}$.

38. The system of claim 37, wherein the instructions further cause the system to:
retrieve, from a database of foods, a plurality of foods $L=\{N_1 \ldots, N_t\}$, wherein each respective food $N_i$, in the plurality of foods, has a corresponding nutrition profile $P_{Ni}=\{D_{ki}, P(z_{ki})\}$; and
order, in terms of recommendations, the plurality of foods L by comparing the diet type $D_j$ and micronutrient recommendation profile assigned to the user to the nutrition profiles $P_N$ of foods N in the plurality of foods L,
wherein the nutrition profile $P_{Ni}=\{D_{ki}, P(z_{ki})\}$ comprises an assigned diet type $D_k$ in the plurality of diet types D and an assigned micronutrient profile $P(z_k)=\{v(z_i) \ldots, v(z_s)\}$, and
wherein the assigned micronutrient profile $P(z_k)$ includes a respective value $v(z_i)$ for each micronutrient $z_i$ in the plurality of micronutrients Z.

39. The system of claim 35, further comprising:
a user's health database configured to store information, of the user, about one or more of phenotypical data, health data, genotypic data, goals, or food preference;
a meal and recipe database configured to store information on one or more of meals, recipes, supplements or hero foods that are available for recommendation to the user;
a meal processing engine for receiving data associated with foods, meals and/or recipes in terms of number of calories, macronutrients and/or micronutrients, for converting the data into a format usable by the system and storing the data in the meal and recipe database,
a decision tree engine, for producing macronutrient and micronutrient classifications for the user based on the user's health data;
a user specific filtering engine, for filtering meal data based on the user's macronutrient classifications, diet type, the user's goals and/or food preferences; and
a meal ranker engine, food selection classifier or food recommendation classifier for receiving available meals, the user's macronutrient classifications and/or diet type, the user's micronutrient classifications, and information from the user health database and meal and recipe database.

40. The system of claim 35,
wherein the machine-learning model comprises one or more of linear discriminant analysis, logistic discriminate analysis, logistic regression analysis, nearest neighbor classifier analysis, principal component analysis, quadratic discriminant analysis, regression classifier analysis, vector machine analysis, classification and regression tree analysis, multiple additive regression tree analysis, prediction analysis for microarrays, random forest analysis, generalized additive analysis, neural network analysis, or non-parametric algorithm analysis.

41. A computer-implemented method comprising:
retrieving, from memory, values in categories, the values representing a user's data in the categories, wherein the user's data comprise phenotypical data, wherein the phenotypical data includes metabolic adaptability information determined through analysis of blood of the user following consumption of a multi-nutrient challenge beverage, and wherein the multi-nutrient challenge beverage includes a) from 44 to 57 grams total fats;
b) 75±15 grams total carbohydrates; and
c) 20±3 grams total protein;

iteratively comparing, via a machine-learning model trained on users' phenotypic data to predict three or more scalar values representing macronutrient recommendations, the retrieved values to ranges associated with the categories, with each category having one or more thresholds separating ranges, wherein the iterative comparisons adjust a comparison result across the iterative comparisons;

converting, based on the three or more determined scalar values, the three or more determined scalar values from scalars to a multi-dimensional vector representation of the three or more determined scalar values;

comparing, based on the conversion, the multi-dimensional vector with possible macronutrient and/or micronutrient recommendations where the possible recommendations exist in a space defined by possible vectors;

determining, based on a matching of the multi-dimensional vector with a recommendation of the possible recommendations, a matching macronutrient and/or micronutrient recommendation covering vector space identified by the multi-dimensional vector; and outputting, based on the determination of the matching of the multi-dimensional vector with the recommendation, the matching macronutrient and/or micronutrient recommendation.

42. The computer-implemented method of claim 41,
wherein the retrieved values further comprise genotypic data of the user,
wherein the genotypic data comprises a plurality of first features $X=\{x_i \ldots, x_m\}$, wherein each respective feature xi in the plurality of first features X is a status of a locus in a plurality of loci,
wherein the phenotypic data comprises a plurality of second features $Y=\{y_1 \ldots, y_n\}$, wherein each respective feature $y_i$ in the plurality of second features Y is a status of a phenotype in a plurality of phenotypes,
wherein the matching recommendation is a diet type $D_j$ in a plurality of diet types $D=\{D_1 \ldots, D_q\}$, where the plurality of diet types are defined in the vector space.

43. The computer-implemented method of claim 41, further comprising:
retrieving, from the memory, second values of the user's data;
comparing the second values to additional ranges defined by one or more thresholds; and
determining, based on the comparison of the second values to the additional ranges, micronutrient recommendations,
wherein the matching recommendation is a diet type $D_j$ in a plurality of diet types $D=\{D_1 \ldots, D_q\}$, where the plurality of diet types are defined in the vector space, and
wherein the micronutrient recommendations comprise a micronutrient recommendation profile $R_j=\{r(z_i) \ldots, r(z_s)\}$ comprising a recommendation $r(z_i)$ for each respective micronutrient $z_i$ in a plurality of micronutrients $Z=\{z_1 \ldots, z_s\}$.

44. The method of claim 41,
wherein the machine-learning model comprises one or more of linear discriminant analysis, logistic discriminate analysis, logistic regression analysis, nearest neighbor classifier analysis, principal component analysis, quadratic discriminant analysis, regression classifier analysis, vector machine analysis, classification and regression tree analysis, multiple additive regression tree analysis, prediction analysis for microarrays, random forest analysis, generalized additive analysis, neural network analysis, or non-parametric algorithm analysis.

* * * * *